(12) United States Patent
Agur et al.

(10) Patent No.: US 8,504,303 B2
(45) Date of Patent: *Aug. 6, 2013

(54) SYSTEM AND METHODS FOR OPTIMIZED DRUG DELIVERY AND PROGRESSION OF DISEASED AND NORMAL CELLS

(75) Inventors: Zvia Agur, Tel Aviv (IL); Sarel Fleishmann, Nes-Ziona (IL); Kirill Skomorovski, Rehovot (IL); Moshe Vardi, Rehovot (IL)

(73) Assignee: Optimata, Ltd, Ramat Gan (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/531,698

(22) Filed: Jun. 25, 2012

(65) Prior Publication Data

US 2012/0284005 A1 Nov. 8, 2012

Related U.S. Application Data

(62) Division of application No. 11/390,250, filed on Mar. 28, 2006, which is a division of application No. 10/192,001, filed on Jul. 10, 2002, now Pat. No. 7,266,483, which is a division of application No. 09/691,053, filed on Oct. 19, 2000, now Pat. No. 6,871,171.

(51) Int. Cl.
 *G01N 33/48* (2006.01)
 *G01N 31/00* (2006.01)
 *G06G 7/48* (2006.01)
 *G06G 7/58* (2006.01)

(52) U.S. Cl.
 USPC .......... 702/19; 702/22; 703/11; 703/12

(58) Field of Classification Search
 None
 See application file for complete search history.

(56) References Cited

U.S. PATENT DOCUMENTS

| | | | |
|---|---|---|---|
| 5,808,918 | A | 9/1998 | Fink et al. |
| 5,879,673 | A | 3/1999 | Thomas |
| 5,930,154 | A | 7/1999 | Thalhammer-Reyero |
| 6,081,786 | A | 6/2000 | Barry et al. |

OTHER PUBLICATIONS

Zvia Agur et al., "Optimizing chemotherapy scheduling using local search heuristics", Operations Reserach, 2006, 54(5):829-846.

R. Stoffel et al., "Thrombopoietin in Thrombocytopenic Mice: Evidence Against Regulation at the mRNA Level and for a Direct Regulatory Role of Platelets," The American Society of Hematology, Blood, vol. 87, No. 2, pp. 567-573, Jan. 15, 1996.

J. Y. Mary, "Normal Human Granulopoiesis Revisited. I. Blood Data," Biomedicine & Pharmacotherapy, vol. 38, pp. 33-43, 1984.

J.Y. Mary, "Normal Human Granulopoiesis Revisited. II. Bone Marrow Data," Biomedicine & Pharmacotherapy, vol. 38, pp. 66-77, 1984.

(Continued)

*Primary Examiner* — Larry D Riggs, II
(74) *Attorney, Agent, or Firm* — Sughrue Mion, PLLC

(57) ABSTRACT

System for recommending an optimal treatment protocol for a specific individual are disclosed. The systems comprise generally a system model, a plurality of treatment protocols, a system model modifier, wherein said system model is modified by the system model modifier based on parameters specific to the individual; and a selector to select an optimal treatment protocol from said plurality of treatment protocols based on the modified system model. Systems embodying the above techniques but for a general patient are also disclosed. Systems for a general patient and an individual for various specific diseases are disclosed. Methods and computer program products embodying the above techniques are also disclosed.

28 Claims, 16 Drawing Sheets

OTHER PUBLICATIONS

C. Dresch, et al., "Growth fraction of myelocytes in normal human granulopoiesis," Cell Tissue Kinet. vol. 19, pp. 11-22, 1986.

S. Schmitz, et al., "The effect of continuous G-CSF application in human cyclic neutropenia: a model analysis," British Journal of Haematology, vol. 90, pp. 41-47, 1995.

S. Schmitz, et al., "Quantification of the cell kinetic effects of G-CSF using a model of human granulopoiesis," International Society for Experimental Hematology, Experimental Hematology, vol. 21, pp. 755-760, 1993.

L. A. Harker, et al., "Regulation of Platelet Production and Function by Megakaryocyte Growth and Development Factor in Nonhuman Primates," The American Society of Hematology, No. 5, pp. 1833-1844, Mar. 1996.

Warren S. Alexander, "Thrombopoietin," The Walter and Eliza Hall Inst. for Medical Research, Growth Factors, vol. 17, pp. 13-24, 1999.

Kenneth Kaushansky, "Thrombopoietin: The Primary Regulator of Platelet Production," The Journal of The American Society of Hematology, Blood, vol. 86, No. 2, pp. 419-431, Jul. 15, 1995.

Saroj Vadhan-Raj, "Recombinant Human Thrombopoietin: Clinical Experience and In Vivo Biology," Seminars in Hematology, vol. 35, No. 3, pp. 261-268, Jul. 1998.

Laurence A. Harker, "Physiology and clinical applications of platelet growth factors," Curr Opin Hematol, vol. 6, pp. 127-134, 1999.

Jack Levin, "Thrombopoietin—Clinically Realized?," The New England Journal of Medicine, vol. 336, No. 6, pp. 1-3, Feb. 6, 1997.

G. Somlo, et al., "Recombinant Human Thrombopoietin in Combination with Granulocyte Colony-Stimulating Factor . . . High-Dose Chemotherapy," The American Society of Hematology, Blood, vol. 93, No. 9, pp. 2798-2806, May 1, 1999.

K. J. Neelis, et al., "The Efficacy of Single-Dose Administration of Thrombopoietin with Coadministration . . . Myelosuppressed Rhesus Monkeys," The American Society of Hematology, Blood, vol. 90, No. 7, pp. 2565-2573, Oct. 1, 1997.

L. J. Murray, et al., "Thrombopoietin Mobilizes Cd34+ Cell Subsets Into Peripheral Blood and Expands Multilineage Progenitors in Bone Marrow of Cancer Patients With Normal Hematopoiesis," Experimental Hematology, vol. 26, pp. 207-216, 1998.

R. L. Basser, et al., "Randomized, Blinded, Placebo-Controlled Phase I Trial of Pegylated Recombinant Human Megakaryocyte Growth and Development Factor with Filgrastim after Dose-Intensive Chemotherapy in Patients with Advanced Cancer," The American Society of Hematology, Blood, vol. 89, No. 9, pp. 3118-3128, 1997.

D. Zucker-Franklin, "The Ultrastructure of Megakaryocytes and Platelets," Dept. of Medicine and Rheumatic Diseases Study Group, New York, The Platelets, Ch. 55, pp. 1553-1629.

L. A. Harker, et al., "Thrombokinetics in Man," The Journal of Clinical Investigation, vol. 48, pp. 963-974, 1969.

Laurence H. Harker, "Thrombokinetics in Idiopathic Thrombocytopenic Purpura," British Journal of Haematology, pp. 95-104, 1970.

R. Sungaran, et al., "Localization and Regulation of Thrombopoietin mRNA Expression in Human Kidney, Liver, Bone Marrow, and Spleen Using in Situ Hybridization," The American Society of Hematology, Blood, vol. 89, No. 1, pp. 101-107, 1997.

Y. Nagata, et al., "Serum Thrombopoietin Level is not Regulated by Transcription but by the Total Counts of both Megakaryocytes and Platelets during Thrombocytopenia and Thrombocytosis," Tsukuba Life Science Center, Thrombosis and Haemostasis, vol. 77, pp. 808-814, 1997.

H. Nagahisa, et al., "Bone Marrow Stromal Cells Produce Thrombopoietin and Stimulate Magakaryocyte Growth and Maturation but Suppress Proplatelet Formation," The American Society of Hematology, Blood, vol. 87, No. 4, pp. 1309-1316, Feb. 15, 1996.

I. Athanassios, et al., "Comparison Between Optimata's Claims and Contemporary, 'state of the art' in Optimizing of Anticancer Chemotherapy," Computers and Biomedical Research, vol. 33, pp. 211-226, 2000.

Hui-Chi Hsu, et al., "Circulating Levels of Thrombopoietic and Inflammatory Cytokines in Patients with Clonal and Reactive Thrombocytosis," J Lab Clin Med, vol. 134, No. 4, pp. 392-397, 1999.

Jain et al. (First International Symposium on 3D Radiation Treatment Planning and Conformal Therapy, 1993, 1-21).

Jain et al. (Proc. Annu. Symp. Comput. Appl. Med. Care, 1991, 1000-1004) referred to as (Jain II).

Warren S. Alexander, "Thrombopoietin and the c-Mpl receptor: insights from gene targeting," The International Journal of Biochemistry & Cell Biology, pp. 1027-1035, Jan. 28, 1999.

M. Miyazaki, et al., "The Relationship Between Carboplatin AUC and Serum Thrombopoietin Kinetics in Patients with Lung Cancer," 2nd Department of Internal Medicine, Hiroshima University School of Medicine, Anti Cancer Research, vol. 19, pp. 667-670 (1999).

S. Vadhan-Raj, et al., "Stimulation of Megakaryocyte and Platelet Production by a Single Dose of Recombinant Human Thrombopoietin in Patients with Cancer," Annals of Internal Medicine, vol. 126, No. 9, pp. 673-681, May 1997.

H.-E. Wichmann, et al., "A Mathematical Model of Thrombopoiesis in Rats," Cell Tissue Kinet, vol. 12, pp. 551-567, Jan. 1979.

L. A. Harker, et al., "Effects of megakaryocyte growth and development factor on platelet production, platelet life span, and platelet function in healthy human volunteers," The American Society of Hematology, Blood, vol. 95, No. 8, pp. 2514-2522, Apr. 15, 2000.

H. Mayani, et al., "Lineage Commitment in Human Hemopoiesis Involves Asymmetric Cell Division of Multipotent Progenitors and Does not Appeal to be Influenced by Cytokines," Journal of Cellular Physiology, vol. 157, pp. 579-586, 1993.

David W. Golde, "The Stem Cell," Scientific American, pp. 36-43, Dec. 1991.

S. J. Morrison, et al., "The Biology of Hematopoietic Stem Cells," Annu. Rev. Cell Dev. Biol., vol. 11, pp. 35-71, 1995.

J. Eller, et al., "Modelling Thrombopoiesis Regulation-I; Model Description and Simulation Results," Comput. Math. Applic., vol. 14, No. 9-12, pp. 841-848, 1987.

G. K. von Schulthess, et al., "Oscillating platelet counts in healthy individuals: Experimental investigation and quantitive evaluation of thrombocytopoietic feedback control," Scand J Haematol, vol. 36, pp. 473-479, Mar. 8, 1986.

L. A. Harker, et al., "Dose-Response Effects of Pegylated Human Megakaryocyte Growth and Development Factor on Platelet Production and Function in Nonhuman Primates," The American Society of Hematology, Blood, vol. 88, No. 2, pp. 511-521, Jul. 15, 1996.

P. A. Fielder, "Regulation of Thrombopoietin Levels by c-mpl-Mediated Binding to Platelets," The American Society of Hematology, Blood, vol. 87, No. 6, pp. 2154-2161, Mar. 15, 1996.

John E. J. Raski, et al., "Molecules in focus; The thrombopoietic factor, Mpl-ligand," The International Journal of Biochemistry & Cell Biology, vol. 30, pp. 657-660, 1998.

F. J. de Sauvage, et al., "Physiological Regulation of Early and Late Stages of Megakaryocytopoiesis by Thrombopoietin," Departments of Molecular Biology, Cell Genetics, vol. 183, pp. 651-656, Feb. 1996.

F. Tacke, et al., "Endogenous serum levels of thrombopoietic cytokines in healthy whole-blood and platelet donors: implications for plateletpheresis," British Journal of Haematology, vol. 105, pp. 511-513, 1999.

S. A. Burstein, et al., "Megakaryopoiesis and platelet formation," Williams Hematology, 5th ed., Ch. 118, McGraw-Hill, Inc., 1995.

R. Schofield, et al., "Self-Maintenance Capacity of CFU-S," Journal of Cellular Physiology, vol. 103, pp. 355-362, 1980.

M. Rosendaal, et al., "Organization of Haemopoietic Stem Cells: The Generation-Age Hypothesis," Cell Tissue Kinet., vol. 12, pp. 17-29, 1979.

A. Iliadis, et al., "Optimizing Drug Regimens in Cancer Chemotherapy by an Efficacy-Toxicity Mathematical Model," Computers and Biomedical Research, vol. 33, pp. 211-226, 2000.

F. L. Pereira, et al., "A new optimization based approach to experimental combination chemotherapy," Frontiers Med. Biol. Engng., vol. 6, No. 4, pp. 257-268, 1995.

Hassin Agur, "Optimizing Chemotherapy Scheduling Using Search Heuristics," pp. 2-36.

Kenji Terashi, et al., "Close Association between Clearance of Recombinant Human Granulocyte Colony-Stimulating Factor (G-CSF) and G-CSF Receptor on Neutrophils in Cancer Patients," Antimicrobial Agents and Chemotherapy, vol. 43, No. 1, pp. 21-24, Jan. 1999.

T. H. Price, et al., "Effect of Recombinant Granulocyte Colony-Stimulating Factor on Neutrophil Kenetics in Normal Young and Elderly Humans," The American Society of Hematology, vol. 88, No. 1, pp. 335-340, Jul. 1, 1996.

B. I. Lord, et al., "The kinetics of human granulopoiesis following treatment with granulocyte colony-stimulating factor in vivo," Proc. Natl. Acad. Sci. USA, vol. 86, pp. 9499-9503, Dec. 1989.

Hwitt et al. Pharmacokinetics and pharmacodynamics of granulocyte-macrophage colony-stimulating factor and zidovudine in patients with AIDS-related complex. Antimicrobial Agents and Chemotherapy. (Mar. 1993) vol. 37, No. 3, pp. 512-522.

Duhrsen et al. Effects of recombinant human granulocyte colony-stimulating factor on hematopoietic progenitor cells in cancer patients. Blood (1988) vol. 72, No. 6, pp. 2074-2081.

Merchant et al., Bronchoalveolar lavage cellularity and distribution in normal volunteers. American review of respiratory Disease. (1992) col. 146, No. 2, pp. 448-453.

Piotrovsky, V.K. Indirect pharmacodynamic response models do not require any parametric pharmacokinetics model to be fitted to effect-time data. Methods and Findings in Experimental and Clinical Pharmacology. (1997) vol. 19, No. 10, pp. 723-729.

Kliem et al. A mathematical model of thrombopoiesis in mice. Experimental Hematology. 1997 vol. 25(8), p. 899.

FIG. 4

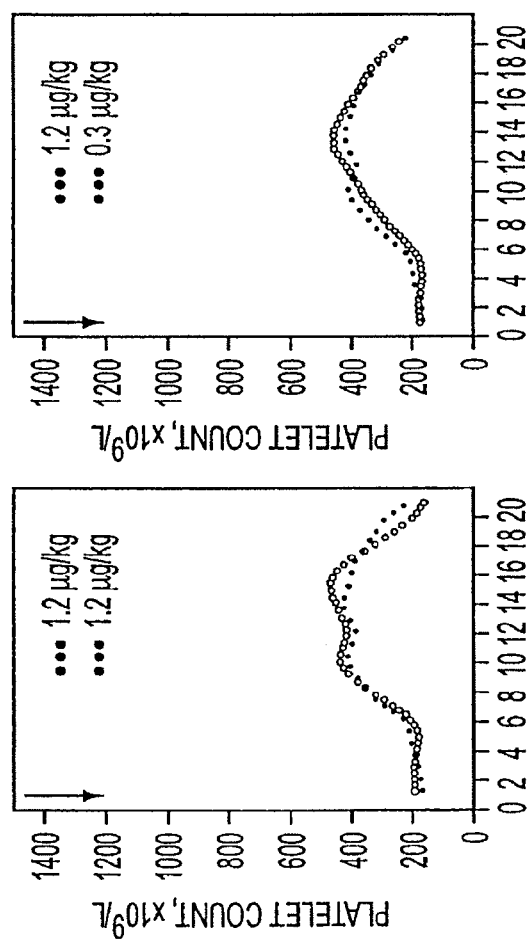

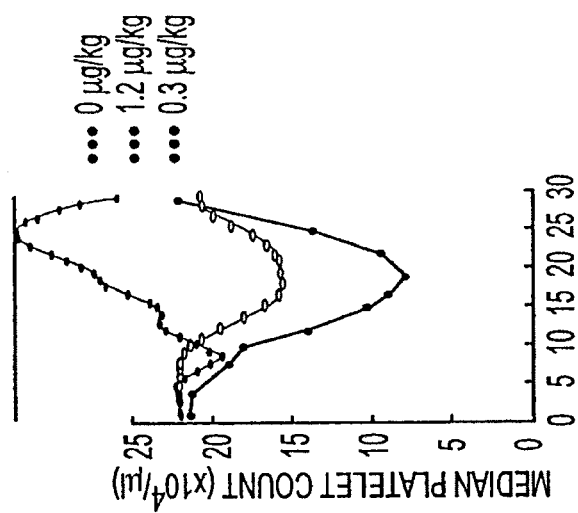
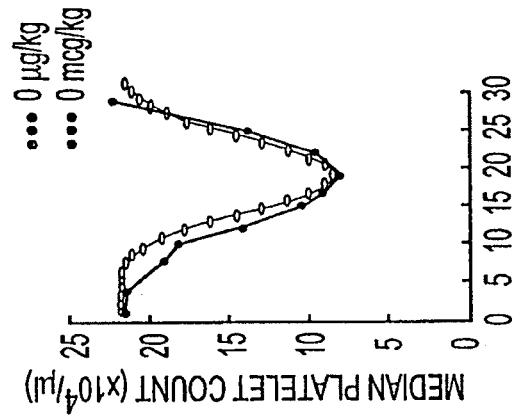
FIG. 9B
FIG. 9A

SYSTEM AND METHODS FOR OPTIMIZED DRUG DELIVERY AND PROGRESSION OF DISEASED AND NORMAL CELLS

CROSS-REFERENCE TO RELATED APPLICATIONS

This is a divisional of pending U.S. application Ser. No. 11/390,250 filed Mar. 28, 2006, which is a Divisional application of U.S. application Ser. No. 10/192,001 filed Jul. 10, 2002, which issued as U.S. Pat. No. 7,266,483, which is a Divisional application of U.S. application Ser. No. 09/691,053 filed Oct. 19, 2000, which issued as U.S. Pat. No. 6,871,171. The entire disclosures of the prior applications are hereby incorporated by reference.

I. DESCRIPTION OF THE INVENTION

I.A. Field of the Invention

The present invention relates generally to prediction of a progression of healthy and diseased cells in patients with/without treatment effect incorporated therein. The present invention is embodied in systems, methods and computer program products for predicting the progression of a biological system, and for prediction and optimization of treatment of disease. These systems, methods and computer program products can be used to simulate a general patient for the use in certain stages in drug development and trials as well as for an individual patient.

I.B. Background of the Invention

It is well known that when drugs are administered to combat diseases, they do not differentiate between healthy and diseased cells. The drugs are often toxic to healthy cells as well, Therefore, in prescribing a specific treatment protocol, it is necessary to consider the effect of the treatment protocol on both healthy cells as well as diseased cells.

Mathematical models that model biological systems are well known in the art. A wide variety of models are known including those that use ordinary differential equations, partial differential equations and the like, More specifically, these mathematical models can simulate cell lines, tumor growth, etc. Conventionally, these models have been used for prediction of treatment results. However, such conventional predictive models generally employ an analytical approach, in which generalizations about the effect of the treatment protocols on a disease must be made. This approach, while providing useful general information, cannot be used to predict results of treatment in realistic circumstances. Thus, techniques that include more complex and detailed scenarios are needed.

II. SUMMARY OF THE INVENTION

It is an objective of the present invention to provide techniques for recommending optimal treatments for a general patient and a specific individual patient.

It is another objective of the invention to provide techniques for predicting the progress of biological processes in a general patient and a specific individual patient under a variety of treatment protocols as well as under no treatment.

It is yet another objective of the present invention to provide techniques for modelling various specific biological processes for a general patient and a specific individual patient under a plurality of treatment protocols including no treatment.

To meet the objectives of the present invention, there is provided a system for recommending an optimal treatment protocol for an individual comprising a system model, a plurality of treatment protocols, a system model modifier. The system model is modified by the system model modifier based on parameters specific to the individual. The system further comprises a selector to select an optimal treatment protocol from the plurality of treatment protocols based on the modified system model.

Preferably the system model further comprises a realistic biological process model and a realistic treatment model that models the effects of a treatment on the biological process.

Still preferably, the biological process model comprises mathematical models for biological processes affecting healthy cell populations and biological processes affecting cell populations with at least one disease.

Still preferably the healthy cell populations include bone-marrow cells and host tissue cells that are affected by the treatment model.

Still preferably the cell populations with at least one disease is one of cancer cells, and diseased bone-marrow cells including diseased Neutrophil cells and diseased Thrompocyte cells.

Preferably, the treatment models comprise treatment specific processes that affect cell population.

Still preferably the treatment specific process is interactions involving one of a group comprising pharmacokinetic, pharmacodynamic, cytostatic, cytotoxic, and methods of affecting cell biology and causing cell death, with associated biological processes.

Preferably the parameters specific to the individual include one or more selected from a group consisting of parameters related to the biological process' dynamics, patient specific drug PK, PD and dynamics of dose-limiting host tissues.

Still preferably the parameters related to biological process' dynamics comprise age, weight, gender, blood picture, desired length of treatment protocol, previous reaction to treatment, molecular markers, genetic markers, pathologic specifics and cytologic specifics.

Preferably the selector incorporates user-specific parameters in performing selection.

Still preferably the incorporation is done by using a fitness function.

Still preferably the fitness function incorporates at least one parameter selected from a group comprising patient survival, time to death, time to reach a specified disease stage (including cure), tumor load, pathogen load, cytotoxicity, side effects, quality of life, cost of treatment, and pain.

Still preferably a user can input specific coefficients for said at least one parameter to adjust the fitness function to satisfy the user's goals.

Still preferably the user-specific parameters are based on a user, said user being a medical doctor.

Still preferably the user-specific parameters are based on a user, said user being a scientist.

Still preferably the user-specific parameters are based on a user, said user being a drug developer.

Preferably the selection of treatment protocols incorporate cytotoxic effects.

Preferably the selection of treatment protocols incorporate drug efficacy.

Preferably the selector performs the selection using operation research methods.

Preferably the selector further comprises heuristics, said heuristics being used to perform searching and selection.

Still preferably said heuristics comprise computational feasibility.

Preferably, the recommendation is a combination of disease and treatment strategy, including types of treatment, e.g.

chemotherapy, radiotherapy, surgery, immunotherapy, etc, device, drug or drug combination and treatment schedule and dosage.

Preferably the system is implemented over a distributed computing system.

Still preferably the distributed computing system is the Internet.

Still preferably a user uses the system remotely.

Another aspect of the present invention is a system for recommending an optimal treatment protocol for a general patient comprising a system model, a plurality of treatment protocols and a selector to select an optimal treatment protocol from said plurality of treatment protocols based on the system model.

Preferably the system model further comprises a realistic biological process model and a realistic treatment model that models the effects of a treatment on said biological process.

Still preferably, the biological process model comprises mathematical models for biological processes affecting healthy cell populations and biological processes affecting cell populations with at least one disease.

Still preferably, the healthy cell populations include bone-marrow cells and host tissue cells that are affected by said treatment model.

Still preferably, the cell populations with at least one disease is one of cancer cells, and diseased bone-marrow cells including diseased Neutrophil cells and diseased Thrompocyte cells.

Still preferably, the treatment models comprise treatment specific processes that affect cell populations.

Still preferably, the treatment specific process is interactions involving one of a group comprising pharmacokinetic, pharmacodynamic, cytostatic, cytotoxic, and methods of affecting cell biology and causing cell death, with associated biological processes.

Preferably the selector incorporates user-specific parameters in performing selection.

Still preferably, the incorporation is done by using a fitness function.

Still preferably, the fitness function incorporates at least one parameter selected from a group comprising patient survival, time to death, time to reach a specified disease stage and cure, tumor load, pathogen load, cytotoxicity, side effects, quality of life, cost of treatment and pain.

Still preferably, a user can input specific coefficients for said at least one parameter to adjust the fitness function to satisfy the user's goals.

Still preferably, the user-specific parameters are based on a user, said user being a medical doctor.

Still preferably, the user-specific parameters are based on a user, said user being a scientist.

Still preferably, the user-specific parameters are based on a user, said user being a drug developer.

Preferably, the selection of treatment protocols incorporate cytotoxic effects.

Preferably, the selection of treatment protocols incorporate drug efficacy.

Preferably, the selector performs the selection using operation research methods.

Preferably, the selector further comprises heuristics, said heuristics being used to perform searching and selection.

Still preferably, the heuristics comprise computational feasibility.

Preferably, the recommendation is a combination of disease and treatment strategy, including types of treatment, e.g.

chemotherapy, radiotherapy, surgery, immunotherapy, etc, device, drug or drug combination and treatment schedule and dosage.

Preferably, the system is implemented over a distributed computing system.

Still preferably, the distributed computing system is the Internet.

Still preferably, a user uses the system remotely.

Still preferably, the remote system is a telephone.

Yet another aspect of the present invention is a system for predicting progression of a biological process in an individual patient under a plurality of treatment protocols, wherein said biological process could be related to healthy or diseased processes, said plurality of protocols including no treatment. The system comprises a system model, a plurality of treatment protocols and a system model modifier. The system model is modified by the system model modifier based on parameters specific to the individual. The system further comprises a predictor to predict the progression of at least one of the disease and the natural biological process under said plurality of treatment protocols based on the modified system model.

Preferably, the system model further comprises a realistic biological process model and a realistic treatment model that models the effects of a treatment on said biological process.

Still preferably, the biological process model comprises mathematical models for biological processes affecting healthy cell populations and biological processes affecting cell populations with at least one disease.

Still preferably, the healthy cell populations include bone-marrow cells and host tissue cells that are affected by said treatment model.

Still preferably, the cell populations with at least one disease is one of cancer cells, and diseased bone-marrow cells including diseased at least one of Neutrophil cells and diseased Thrombocyte cells.

Still preferably, the treatment models comprise treatment specific processes that affect cell population.

Still preferably the treatment specific process is interactions involving one of a group comprising PK, PD, cytostatic, cytotoxic, and methods of affecting cell biology and causing cell death, with associated biological processes.

Preferably the parameters specific to the individual include one or more selected from a group consisting of parameters related to the biological process' dynamics, patient specific drug PK, PD and dynamics of dose-limiting host tissues.

Still preferably, the parameters related to biological process' dynamics comprise age, weight, gender, blood picture, desired length of treatment protocol, previous reaction to treatment, molecular markers, genetic markers, pathologic specifics and cytologic specifics.

Yet another aspect of the present invention is a system for predicting progression of a biological process in a general patient under a plurality of treatment protocols, wherein said biological process could be healthy or diseased processes, said plurality of protocols including no treatment. The system comprises a system model, a plurality of treatment protocols and a predictor to predict the progression of the disease or the natural biological process under said plurality of treatment protocols.

Preferably, the system model further comprises a realistic biological process model and a realistic treatment model that models the effects of a treatment on said biological process.

Still preferably, the biological process model comprises mathematical models for biological processes affecting healthy cell populations and biological processes affecting cell populations with at least one disease.

Still preferably, the healthy cell populations include bone-marrow cells as well as other host tissue cells that are affected by said treatment model.

Still preferably, the cell populations with at least one disease is one of cancer cells, and diseased bone-marrow cells including diseased Neutrophil cells and diseased Thrombocyte cells.

Still preferably, the treatment models comprise treatment specific processes that affect cell population.

Still preferably, the treatment specific process is interactions involving one of a group comprising PK, PD, drug cytostatics, drug cytotoxics, and methods of affecting cell biology and causing cell death, with associated biological processes.

Yet another aspect of the present invention is a system for modelling Thrombopietic lineage in an individual, said system comprising a Thrombopoiesis system model including a realistic process progression model, for cells involved in Thrombopoiesis, said progression model including multiplication and differentiation and a system model modifier, wherein said Thrombopoiesis system model is modified by the system model modifier based on parameters specific to the individual.

Preferably, the system model incorporates a realistic progression of cells involved in diseased Thrombopoiesis.

Still preferably, the diseased Thrombopoiesis includes Thrombocytopenia.

Still preferably, the system model incorporates effects of at least one drug in the realistic progression of cells involved in Thrombopoiesis.

Still preferably, said at least one drug is Thrombopoietin (TPO).

Still preferably, the process model imitates a course of the individual's bone marrow progression, peripheral platelet counts and TPO concentration changes.

Still preferably, said process model incorporates cell-suppressive treatment effects and administration of TPO to the patient.

Still preferably, said cell-suppressive treatment can be chemotherapy.

Still preferably, the process model further comprises a plurality of compartments.

Still preferably, the compartments include:

a stem cell (SC) compartment that comprises bone marrow haemopoietic progenitors that have an ability to differentiate into more than one cell line wherein cells in the stem cell compartment proliferate and differentiate into one of megakaryocyte;

a colony forming units-megakaryocytes (CFU-Meg) compartment, wherein the megakaryocyte progenitors get committed as a megakaryocyte line and spend some time multiplying and maturing;

a megakaryoblast (MKB) compartment, which receives the cells from CFU-Meg, wherein the cells in the MKB compartment have lost their ability to proliferate but are not mature to release platelets;

a MK16 compartment, which receives cell from the MKB compartment, wherein a subset of cells in the MK16 compartment release platelets at a constant rate until they exhaust their capacity and are disintegrated and a second subset of cells do not release platelets but continue with endomitosis;

a MK32 compartment that receives cells from the MK16 compartment, wherein a subset of cells in this compartment release platelets and a second subset of cells do not release platelets but continue with endomitosis;

a MK64 compartment that receives cells from the MK32 compartment wherein a subset of cells in this compartment release platelets and a second subset of cells do not release platelets but continue with endomitosis;

a MK128 compartment that receives cells from the MK64 compartment wherein a subset of cells in this compartment release platelets; and a platelets (PL) compartment.

Still preferably, an effect of apoptosis is included with an overall effect of cell proliferation in giving rise to an amplification of cell numbers in a corresponding compartment.

Still preferably, the process model further incorporates the effects of TPO on the SC, CFU-Meg and MKB compartments.

Still preferably, the effects are expressed in terms of effects of TPO concentration on amplification rate, rate of cell maturation and a fraction of cells that undergo endomitosis.

Still preferably, when the TPO concentration is above a predetermined threshold level, the amplification rate of cells in the SC compartment are affected and below the threshold the amplification rate is dependent only on a current number of cells.

Still preferably, in the CFU-Meg compartment the cells are sensitive to TPO concentration regardless of the concentration of TPO.

Still preferably the transit time is same in all platelet releasing compartments and the transit time of the SC, CFU-Meg and MKB compartments are functions of micro-environmental conditions.

Still preferably, the SC compartment when the TPO concentration is above the threshold, the transit time is shortened based the dose.

Still preferably, in the CFU-Meg and MKB, the transit time is solely based on TPO concentration.

Still preferably, a fraction of cells in the SC compartment that commits to megakaryocytic lineage is constant and dependent on TPO.

Still preferably in the CFU-Meg and MKB compartments, every mature cell passes on to the next compartment.

Still preferably, in the MK16, MK32 and MK64 compartments, a fraction of cells pass on to the next compartment, said fraction being dependent on the TPO concentration.

Still preferably, cells from MK128 compartment do not flow into any other compartment.

Still preferably, each of said compartments is further divided into sub-compartments, each of said sub-compartments containing cells of a specific age in hours.

Still preferably, cells that spend all their corresponding transit time in a given compartment pass on to the next compartment, wherein cells that have left a corresponding compartment each hour fill the first sub-compartment of the next compartment.

Still preferably, the platelet releasing cells contribute platelets to the first sub-compartment of the PL compartment.

Preferably the model is used for recommending an optimal treatment protocol, wherein said system further comprises a plurality of treatment protocols and a selector to select an optimal treatment protocol from said plurality of treatment protocols based on the modified system model.

Yet another aspect of the present invention is a system for modelling Thrombopietic lineage in a general patient, said system comprising a Thrombopoiesis system model including a realistic process model for cells involved in Thrombopoiesis.

Preferably, the system model incorporates a realistic progression of cells involved in diseased Thrombopoiesis.

Still preferably, the diseased Thrombopoiesis includes Thrombocytopenia.

Still preferably, the system model incorporates effects of at least one drug in the realistic progression of cells involved in Thrombopoiesis.

Still preferably, said at least one drug is Thrombopoietin (TPO).

Still preferably, the process model imitates a course of the patient's bone marrow progression, peripheral platelet counts and TPO concentration changes.

Still preferably, the process model incorporates cell-suppressive treatment effects and administration of TPO to the patient.

Still preferably, the cell-suppressive treatment is chemotherapy.

Still preferably, the process model further comprises a plurality of compartments.

Still preferably, the compartments include:

a stem cell (SC) compartment that comprises bone marrow haemopoietic progenitors that have an ability to differentiate into more than one cell line wherein cells in the stem cell compartment proliferate and differentiate into one of megakaryocyte;

a colony forming units-megakaryocytes (CFU-Meg) compartment, wherein the megakaryocyte progenitors get committed as a megakaryocyte line and spend some time multiplying and maturing;

a megakaryoblast (MKB) compartment, which receives the cells from CFU-Meg, wherein the cells in the MKB compartment have lost their ability to proliferate but are not mature to release platelets;

a MK16 compartment, which receives cell from the MKB compartment, wherein a subset of cells in the MK16 compartment release platelets at a constant rate until they exhaust their capacity and are disintegrated and a second subset of cells do not release platelets but continue with endomitosis;

a MK32 compartment that receives cells from the MK16 compartment, wherein a subset of cells in this compartment release platelets and a second subset of cells do not release platelets but continue with endomitosis;

a MK64 compartment that receives cells from the MK32 compartment wherein a subset of cells in this compartment release platelets and a second subset of cells do not release platelets but continue with endomitosis;

a MK128 compartment that receives cells from the MK64 compartment wherein a subset of cells in this compartment release platelets; and a platelets (PL) compartment.

Still preferably, an effect of apoptosis are included with an overall effect of cell proliferation in giving rise to an amplification of cell numbers in a corresponding compartment.

Still preferably, the process model further incorporates the effects of TPO on the SC, CFU-Meg and MKB compartments.

Still preferably, the effects are expressed in terms of effects of TPO concentration on amplification rate, rate of cell maturation and a fraction of cells that undergo endomitosis.

Still preferably, when the TPO concentration is above a predetermined threshold level, the amplification rate of cells in the SC compartment are affected and below the threshold the amplification rate is dependent only on a current number of cells.

Still preferably, the CFU-Meg compartment the cells are sensitive to TPO concentration regardless of the concentration of TPO.

Still preferably, the transit time is same in all platelet releasing compartments and the transit time of the SC, CFU-Meg and MKB compartments are functions of micro-environmental conditions.

Still preferably, in the SC compartment when the TPO concentration is above the threshold, the transit time is shortened based the dose.

Still preferably, in the CFU-Meg and MKB, the transit time is solely based on TPO concentration.

Still preferably, a fraction of cells in the SC compartment that commits to megakaryocytic lineage is constant and dependent on TPO.

Still preferably, in the CFU-Meg and MKB compartments, every mature cell passes on to the next compartment.

Still preferably, in the MK16, MK32 and MK64 compartments, a fraction of cells pass on to the next compartment, said fraction being dependent on the TPO concentration.

Still preferably, cells from MK128 compartment do not flow into any other compartment.

Still preferably, each of said compartments is further divided into sub-compartments, each of said sub-compartments containing cells of a specific age in hours.

Still preferably, cells that spend all their corresponding transit time in a given compartment pass on to the next compartment, wherein cells that have left a corresponding compartment each hour fill the first sub-compartment of the next compartment.

Still preferably, the platelet releasing cells contribute platelets to the first sub-compartment of the PL compartment.

Preferably, said model is used for recommending an optimal treatment protocol, wherein said system further comprises a plurality of treatment protocols; and a selector to select an optimal treatment protocol from said plurality of treatment protocols based on the modified system model.

Yet another aspect of the present invention is a system for predicting progression of Thrombopoiesis and a model of Thrombocytopenia for an individual under a plurality of treatment protocols, said plurality of protocols including no treatment, said system comprising a Thrombopoiesis and a Thrombocytopenia system model, a plurality of treatment protocols for affecting Thrombopoiesis and treating Thrombocytopenia using at least one drug, a system model modifier. The Thrombopoiesis and Thrombocytopenia system models are modified by the system model modifier based on parameters specific to the individual. The system further comprises a predictor to predict the progression of the disease or the natural biological process under said plurality of treatment protocols based on the modified system model.

Preferably, the system model incorporates a realistic progression of cells involved in diseased Thrombopoisis.

Still preferably, diseased Thrombopoiesis includes Thrombocytopenia.

Still preferably, the system model incorporates effects of at least one drug on the realistic progression of cells involved in Thrombocytopenia.

Still preferably, said at least one drug is Thrombopoietin (TPO).

Still preferably, said process model imitates a course of the individual's bone marrow progression, peripheral platelet counts and TPO concentration changes.

Still preferably, said process model incorporates cell-suppressive treatment effects and administration of TPO to the patient.

Still preferably, said cell-suppressive treatment is chemotherapy.

Still preferably, said process model further comprises a plurality of compartments.

Still preferably, said compartments include:

a stem cell (SC) compartment that comprises bone marrow haemopoietic progenitors that have an ability to differentiate into more than one cell line wherein cells in the stem cell compartment proliferate and differentiate into one of megakaryocyte;

a colony forming units-megakaryocytes (CFU-Meg) compartment, wherein the megakaryocyte progenitors get committed as a megakaryocyte line and spend some time multiplying and maturing;

a megakaryoblast (MKB) compartment, which receives the cells from CFU-Meg, wherein the cells in the MKB compartment have lost their ability to proliferate but are not mature to release platelets;

a MK16 compartment, which receives cell from the MKB compartment, wherein a subset of cells in the MK16 compartment release platelets at a constant rate until they exhaust their capacity and are disintegrated and a second subset of cells do not release platelets but continue with endomitosis;

a MK32 compartment that receives cells from the MK16 compartment, wherein a subset of cells in this compartment release platelets and a second subset of cells do not release platelets but continue with endomitosis;

a MK64 compartment that receives cells from the MK32 compartment wherein a subset of cells in this compartment release platelets and a second subset of cells do not release platelets but continue with endomitosis;

a MK128 compartment that receives cells from the MK64 compartment wherein a subset of cells in this compartment release platelets; and a platelets (PL) compartment.

Still preferably, an effect of apoptosis are included with an overall effect of cell proliferation in giving rise to an amplification of cell numbers in a corresponding compartment.

Still preferably, the process model further incorporates the effects of TPO on the SC, CFU-Meg and MKB compartments.

Still preferably, the effects are expressed in terms of effects of TPO concentration on amplification rate, rate of cell maturation and a fraction of cells that undergo endomotisis.

Still preferably, the TPO concentration is above a predetermined threshold level, the amplification rate of cells in the SC compartment are affected and below the threshold the amplification rate is dependent only on a current number of cells.

Still preferably, in the CFU-Meg compartment the cells are sensitive to TPO concentration regardless of the concentration of TPO.

Still preferably, the transit time is same in all platelet releasing compartments and the transit time of the SC, CFU-Meg and MKB compartments are functions of micro-environmental conditions.

Still preferably, in the SC compartment when the TPO concentration is above the threshold, the transit time is shortened based the dose.

Still preferably, in the CFU-Meg and MKB, the transit time is solely based on TPO concentration.

Still preferably, a fraction of cells in the SC compartment that commits to megakaryocytic lineage is constant and dependent on TPO.

Still preferably, in the CFU-Meg and MKB compartments, every mature cell passes on to the next compartment.

Still preferably, in the MK16, MK32 and MK64 compartments, a fraction of cells pass on to the next compartment, said fraction being dependent on the TPO concentration.

Still preferably, cells from MK128 compartment do not flow into any other compartment.

Still preferably, each of said compartments is further divided into sub-compartments, each of said sub-compartments containing cells of a specific age in hours.

Still preferably, cells that spend all their corresponding transit time in a given compartment pass on to the next compartment, wherein cells that have left a corresponding compartment each hour fill the first sub-compartment of the next compartment.

Still preferably, the platelet releasing cells contribute platelets to the first sub-compartment of the PL compartment.

Yet another aspect of the present invention is a system for predicting progression of Thrombopoiesis and a model of Thrombocytopenia for a general patient under a plurality of treatment protocols, said plurality of protocols including no treatment. The system comprises a Thrombopoiesis and a Thrombocytopenia system model, a plurality of treatment protocols for affecting Thrombopoiesis and treating Thrombocytopenia using at least one drug; and a predictor to predict the progression of the disease or the natural biological process under said plurality of treatment protocols based on the modified system model.

Preferably the system model incorporates a realistic progression of cells involved in diseased Thrombopoiesis Still preferably, diseased Thrombopoiesis includes Thrombocytopenia.

Still preferably, the system model incorporates effects of at least one drug in the realistic progression of cells involved in Thrombocytopenia.

Still preferably, said at least one drug is Thrombopoietin (TPO).

Still preferably, said process model imitates a course of the individual's bone marrow progression, peripheral platelet counts and TPO concentration changes.

Still preferably, said process model incorporates cell-suppressive treatment effects and administration of TPO to the patient.

Still preferably, said cell-suppressive treatment is chemotherapy.

Still preferably, said process model further comprises a plurality of compartments.

Still preferably, said compartments include:

a stem cell (SC) compartment that comprises bone marrow haemopoietic progenitors that have an ability to differentiate into more than one cell line wherein cells in the stem cell compartment proliferate and differentiate into one of megakaryocyte;

a colony forming units-megakaryocytes (CFU-Meg) compartment, wherein the megakaryocyte progenitors get committed as a megakaryocyte line and spend some time multiplying and maturing;

a megakaryoblast (MKB) compartment, which receives the cells from CFU-Meg, wherein the cells in the MKB compartment have lost their ability to proliferate but are not mature to release platelets;

a MK16 compartment, which receives cell from the MKB compartment, wherein a subset of cells in the MK16 compartment release platelets at a constant rate until they exhaust their capacity and are disintegrated and a second subset of cells do not release platelets but continue with endomitosis;

a MK32 compartment that receives cells from the MK16 compartment, wherein a subset of cells in this compartment release platelets and a second subset of cells do not release platelets but continue with endomitosis;

a MK64 compartment that receives cells from the MK32 compartment wherein a subset of cells in this compartment release platelets and a second subset of cells do not release platelets but continue with endomitosis;

a MK128 compartment that receives cells from the MK64 compartment wherein a subset of cells in this compartment release platelets; and a platelets (PL) compartment.

Still preferably, an effect of apoptosis are included with an overall effect of cell proliferation in giving rise to an amplification of cell numbers in a corresponding compartment.

Still preferably, the process model further incorporates the effects of TPO on the SC, CFU-Meg and MKB compartments.

Still preferably, the effects are expressed in terms of effects of TPO concentration on amplification rate, rate of cell maturation and a fraction of cells that undergo endomotisis.

Still preferably, when the TPO concentration is above a predetermined threshold level, the amplification rate of cells in the SC compartment are affected and below the threshold the amplification rate is dependent only on a current number of cells.

Still preferably, in the CFU-Meg compartment the cells are sensitive to TPO concentration regardless of the concentration of TPO.

Still preferably, the transit time is same in all platelet releasing compartments and the transit time of the SC, CFU-Meg and MKB compartments are functions of micro-environmental conditions.

Still preferably, in the SC compartment when the TPO concentration is above the threshold, the transit time is shortened based the dose.

Still preferably, in the CFU-Meg and MKB, the transit time is solely based on TPO concentration.

Still preferably, a fraction of cells in the SC compartment that commits to megakaryocytic lineage is constant and dependent on TPO.

Still preferably, in the CFU-Meg and MKB compartments, every mature cell passes on to the next compartment.

Still preferably, in the MK16, MK32 and MK64 compartments, a fraction of cells pass on to the next compartment, said fraction being dependent on the TPO concentration.

Still preferably, cells from MK128 compartment do not flow into any other compartment.

Still preferably, each of said compartments is further divided into sub-compartments, each of said sub-compartments containing cells of a specific age in hours.

Still preferably, cells that spend all their corresponding transit time in a given compartment pass on to the next compartment, wherein cells that have left a corresponding compartment each hour fill the first sub-compartment of the next compartment.

Still preferably, wherein the platelet releasing cells contribute platelets to the first sub-compartment of the PL compartment.

Another aspect of the present invention is a system for modelling Neutrophil lineage for an individual, said system comprising a Neutrophil system model including a realistic process model for cells involved in Granulopoiesis and a system model modifier. The Neutrophil system model is modified by the system model modifier based on parameters specific to the individual.

Preferably, the system model incorporates a realistic progression of cells involved in Granulopoietic disorders, including Neutropenia.

Still preferably, the system incorporates effects of at least one drug in the realistic progression of cells involved in Granulopoiesis and Neutropenia.

Still preferably, said at least one drug is Granulocyte Colony Stimulating Factor (G-CSF);

Still preferably, said model comprises at least three stages, a first stage related to an administered amount of cytokine; a second stage representing a pharmacokinetic behavior of G-CSF; and a third stage representing a pharmacodynamic effect of G-CSF on kinetic parameters of the system.

Still preferably, said model comprises a mitotic compartment, and a post mitotic compartment, said mitotic compartment being divided into subcompartments wherein a kth sub-compartment contains cells of age between k−1 and k hours relative to a time of entry into the mitotic compartment.

Still preferably, effects of toxic drugs, including chemotherapy are incorporated by mapping various cell-cycle phases to the sub-compartments and formulating a function of cytotoxic effects of toxic drugs, including chemotherapy on the cell-cycle phases.

Still preferably, the effects of G-CSF on the mitotic compartment are modeled as an increase in a rate of cells entering the myeloblasts compartment from an uncommitted stem cell pool.

Still preferably, the post-mitotic compartment is modeled as a single pool of cells wherein cells in a last sub-compartment of the mitotic compartment enters the post-mitotic compartment and a proportion of cells within the post-mitotic compartment enters the mature Neutrophil pool every hour.

Still preferably, effects of G-CSF on the Neutrophil lineage are modeled as a decrease in the cells in the post-mitotic compartment which is subsequently compensated by an increased production in the mitotic compartment, said compensation sustaining an increase in Neutrophil count.

Still preferably, an elimination of Neutrophils in the post-mitotic compartment is represented by a Poisson distribution.

Still preferably, the cytotoxic effects of toxic drugs, including chemotherapy in the post-mitotic compartment is modeled as an effect on a single pool of cells.

Still preferably, kinetic of G-CSF is modeled as an exponential distribution.

Still preferably, a selection of an optimal treatment uses an objective function that aims at minimizing G-CSF administration and returning Neutrophil lineage to normal levels.

Still preferably, said selection is performed using linear programming.

Still preferably, pharmacokinetics and pharmacodynamics of G-CSF are defined using piecewise linear functions.

Preferably, said model is used for recommending an optimal treatment protocol, wherein said system further comprises a plurality of treatment protocols; and a selector to select an optimal treatment protocol from said plurality of treatment protocols based on the modified system model.

Yet another aspect of the present invention is system for modelling Neutrophil lineage for a general patient, said system comprising a Granulopoiesis system model including a realistic process model for cells involved in Neutrophil production.

Preferably, the system model incorporates a realistic progression of cells involved in Granulopoiesis disorders including Neutropenia.

Still preferably, the system incorporates effects of at least one drug in the realistic progression of cells involved in Granulopoiesis disorders including Neutropenia.

Still preferably, said at least one drug is Granulocyte Colony Stimulating Factor (G-CSF);

Still preferably, said model comprises at least three stages, a first stage related to an administered amount of cytokine; a second stage representing a pharmacokinetic behavior of G-CSF; and a third stage representing a pharmacodynamic effect of G-CSF on kinetic parameters.

Preferably, said model comprises a mitotic compartment, and a post mitotic compartment, said mitotic compartment being divided into subcompartments wherein a kth sub-compartment contains cells of age between k−1 and k hours relative to a time of entry into the mitotic compartment.

Still preferably, effects of toxic drugs, including chemotherapy are incorporated by mapping various cell-cycle phases to the sub-compartments and formulating a function of cytotoxic effects of toxic drugs, including chemotherapy on the cell-cycle phases.

Still preferably, the effects of G-CSF on the mitotic compartment are modeled as an increase in a rate of cells entering the myeloblasts compartment from an uncommitted stem cell pool.

Still preferably, the post-mitotic compartment is modeled as a single pool of cells wherein cells in a last sub-compartment of the mitotic compartment enters the post-mitotic compartment and a proportion of cells within the post-mitotic compartment enters the mature Neutrophil pool every hour.

Still preferably, effects of G-CSF on the Neutrophil lineage are modeled as a decrease in the cells in the post-mitotic compartment which is subsequently compensated by an increased production in the mitotic compartment, said compensation sustaining an increase in Neutrophil count.

Still preferably, an elimination of Neutrophils in the post-mitotic compartment is represented by a Poisson distribution.

Still preferably, the cytotoxic effects of toxic drugs, including chemotherapy in the post-mitotic compartment is modeled as an effect on a single pool of cells.

Still preferably, kinetic of G-CSF is modeled as an exponential distribution.

Preferably, a selection of an optimal treatment uses an objective function that aims at minimizing G-CSF administration and returning Neutrophil lineage to normal levels.

Still preferably, said selection is performed using linear programming.

Still preferably, pharmacokinetics and pharmacodynamics of G-CSF are defined using piecewise linear functions.

Preferably, said model is used for recommending an optimal treatment protocol, wherein said system further comprises: a plurality of treatment protocols; and a selector to select an optimal treatment protocol from said plurality of treatment protocols based on the modified system model.

Yet another aspect of the present invention is a system for predicting progression of Granulopoiesis for an individual under a plurality of treatment protocols, said plurality of protocols including no treatment, said system comprising a Granulopoiesis system model including a realistic process model for cells involved in Neutrophil production; a plurality of treatment protocols; and a system model modifier. The Neutrophil production system model is modified by the system model modifier based on parameters specific to the individual. The system further comprises a predictor that predicts the progression under the plurality of treatment protocols based on the modified system model.

Preferably, the system model incorporates a realistic progression of cells involved in Granulopoietic disorders, including Neutropenia.

Still preferably, the system incorporates effects of at least one drug in the realistic progression of cells involved in Granulopoiesis and Neutropenia.

Still preferably, said at least one drug is Granulocyte Colony Stimulating Factor (G-CSF).

Still preferably, said model comprises at least three stages, a first stage related to an administered amount of cytokine; a second stage representing a pharmacokinetic behavior of G-CSF; and
a third stage representing a pharmacodynamic effect of G-CSF on kinetic parameters.

Still preferably, said model comprises a mitotic compartment, and a post mitotic compartment, said mitotic compartment being divided into subcompartments wherein a kth sub-compartment contains cells of age between k−1 and k hours relative to a time of entry into the mitotic compartment.

Still preferably, effects of toxic drugs, including chemotherapy are incorporated by mapping various cell-cycle phases to the sub-compartments and formulating a function of cytotoxic effects of toxic drugs, including chemotherapy on the cell-cycle phases.

Still preferably, the effects of G-CSF on the mitotic compartment are modeled as an increase in a rate of cells entering the myeloblasts compartment from an uncommitted stem cell pool.

Still preferably, the post-mitotic compartment is modeled as a single pool of cells wherein cells in a last sub-compartment of the mitotic compartment enters the post-mitotic compartment and a proportion of cells within the post-mitotic compartment enters the mature Neutrophil pool every hour.

Still preferably, effects of G-CSF on the Neutrophil lineage are modeled as a decrease in the cells in the post-mitotic compartment which is subsequently compensated by an increased production in the mitotic compartment, said compensation sustaining an increase in Neutrophil count.

Still preferably, an elimination of Neutrophils in the post-mitotic compartment is represented by a Poisson distribution.

Still preferably, the cytotoxic effects of toxic drugs, including chemotherapy in the post-mitotic compartment is modeled as an effect on a single pool of cells.

Still preferably, kinetic of G-CSF is modeled as an exponential distribution.

Still preferably, a selection of an optimal treatment-uses an objective function that aims at minimizing G-CSF administration and returning Neutrophil lineage to normal levels.

Still preferably, said selection is performed using linear programming.

Still preferably, pharmacokinetics and pharmacodynamics of G-CSF are defined using piecewise linear functions.

Yet another aspect of the present invention is a system for predicting progression of Granulopoiesis for a general patient under a plurality of treatment protocols, said plurality of protocols including no treatment, said system comprising a Neutrophil system model including a realistic process model for cells involved in Neutrophil production a plurality of treatment protocols; and a predictor to that predicts the progression under the plurality of treatment protocols based on the modified system model.

Still preferably, the system model incorporates a realistic progression of cells involved in Granulopoietic disorders, including Neutropenia.

Still preferably, the system incorporates effects of at least one drug in the realistic progression of cells involved in Granulopoiesis and Neutropenia.

Still preferably, said at least one drug is Granulocyte Colony Stimulating Factor (G-CSF).

Still preferably, said model comprises at least three stages, a first stage related to an administered amount of cytokine; a second stage representing a pharmacokinetic behavior of G-CSF; and
a third stage representing a pharmacodynamic effect of G-CSF on kinetic parameters.

Still preferably, said model comprises a mitotic compartment, and a post mitotic compartment, said mitotic compartment being divided into subcompartments wherein a kth subcompartment contains cells of age between k−1 and k hours relative to a time of entry into the mitotic compartment.

Still preferably, effects of toxic drugs, including chemotherapy are incorporated by mapping various cell-cycle phases to the sub-compartments and formulating a function of cytotoxic effects of toxic drugs, including chemotherapy on the cell-cycle phases.

Still preferably, the effects of G-CSF on the mitotic compartment are modeled as an increase in a rate of cells entering the myeloblasts compartment from an uncommitted stem cell pool.

Still preferably, the post-mitotic compartment is modeled as a single pool of cells wherein cells in a last sub-compartment of the mitotic compartment enters the post-mitotic compartment and a proportion of cells within the post-mitotic compartment enters the mature Neutrophil pool every hour.

Still preferably, effects of G-CSF on the Neutrophil lineage are modeled as a decrease in the cells in the post-mitotic compartment which is subsequently compensated by an increased production in the mitotic compartment, said compensation sustaining an increase in Neutrophil count.

Still preferably, an elimination of Neutrophils in the post-mitotic compartment is represented by a Poisson distribution.

Still preferably, the cytotoxic effects of toxic drugs, including chemotherapy in the post-mitotic compartment is modeled as an effect on a single pool of cells.

Still preferably, kinetic of G-CSF is modeled as an exponential distribution.

Still preferably, a selection of an optimal treatment uses an objective function that aims at minimizing G-CSF administration and returning Neutrophil lineage to normal levels.

Still preferably, said selection is performed using linear programming.

Still preferably, pharmacokinetics and pharmacodynamics of G-CSF are defined using piecewise linear functions.

Yet another aspect of the present invention is a system for recommending an optimal treatment protocol for treating cancer using drugs, including chemotherapy, for an individual, said system comprising a cancer system model a plurality of treatment protocols for treating cancer using chemotherapy, a system model modifier. The cancer system model is modified by the system model modifier based on parameters specific to the individual. The system further comprises a selector to select an optimal treatment protocol from said plurality of treatment protocols based on the modified system model.

Preferably, the system model further comprises a realistic process model of cancer development; and a realistic treatment model that models the effects of treating cancer with drugs, including chemotherapy.

Still preferably, said process model incorporates a distribution of cycling cells and quiescent cells.

Still preferably, a tumor cell cycle is divided into at least four compartments G1, S, G2 and M and a quiescent stage is denoted by G0, wherein each of said four compartments is further subdivided into sub-compartments and an ith sub-compartment representing cells of age I in the corresponding compartment, wherein cells entering a compartment always enter a first sub-compartment of the compartment.

Still preferably, the model traces development of cancer cells using a predetermined set of parameters by calculating a number of cells in each subcompartment using stepwise equations.

Still preferably, a probability vector is used to determine a fraction of cells that leaves any subcompartment in a compartment to move to a first subcompartment of the next compartment.

Still preferably, a set control functions uniquely determine an outcome of every single step, wherein said control functions depend on age of cells, state of a current population and associated environment.

Still preferably, a tumor is modelled as a combination of a plurality of homogeneous group of cells, each of said homogeneous group of cells representing a similarly behaving group of cells distributed between all the cell-cycle compartments.

Still preferably, in each step, a number of cells in each sub-compartment of each compartment of each group is calculated according to factors including a previous state, parameters of tumor, tumor current microenvironment and drug concentration.

Still preferably, spatial structure of the tumor is included in the model.

Still preferably, PK and PD, cytostatic effects, cytotoxic effects, and other effects on cell disintegration of anticancer drugs are incorporated into the model.

Still preferably, a dose-limiting toxicity is incorporated into the model.

Still preferably, said parameters specific to the individual comprise parameters related to tumor dynamics, patient specific drug PK, and dynamics of dose-limiting host tissues.

Still preferably, said parameters related to tumor dynamics comprise age, weight, gender, percentage of limiting healthy cells, desired length of treatment protocol, previous reaction to treatment, molecular markers, genetic markers, pathologic specifics and cytologic specifics.

Yet another aspect of the present invention is a system for predicting the a progression of cancer in individual patients comprising a cancer system model, a plurality of treatment protocols for treating cancer using drugs, including chemotherapy a system model modifier. The cancer system model is modified by the system model modifier based on parameters specific to the individual. The system further comprises a predictor to predict the progression of cancer under the plurality of treatment protocols based on the modified system model.

Still preferably, the system model further comprises:
a realistic process model of cancer development; and
a realistic treatment model that models the effects of treating cancer with drugs, including chemotherapy.

Still preferably, said process model incorporates a distribution of cycling cells and quiescent cells.

Still preferably, a tumor cell cycle is divided into at least four compartments G1, S, G2 and M and a quiescent stage is denoted by G0, wherein each of said four compartments is further subdivided into sub-compartments and an ith sub-compartment representing cells of age i in the corresponding compartment, wherein cells entering a compartment always enter a first sub-compartment of the compartment.

Still preferably, the model traces development of cancer cells using a predetermined set of parameters by calculating a number of cells in each subcompartment using stepwise equations.

Still preferably, a probability vector is used to determine a fraction of cells that leaves any subcompartment in a compartment to move to a first subcompartment of the next compartment.

Still preferably, where a set control functions uniquely determine an outcome of every single step, wherein said control functions depend on age of cells, state of a current population and associated environment.

Still preferably, a tumor is modelled as a combination of a plurality of homogeneous group of cells, each of said homogeneous group of cells representing a similarly behaving group of cells distributed between all the cell-cycle compartments.

Still preferably, in each step, a number of cells in each sub-compartment of each compartment of each group is calculated according to factors including a previous state, parameters of tumor, tumor current microenvironment and drug concentration.

Still preferably, spatial structure of the tumor is included in the model.

Still preferably, PK and PD, cytotoxic effects and cytostatic effects of anticancer drugs are incorporated into the model.

Still preferably, a dose-limiting toxicity is incorporated into the model.

Still preferably, said parameters specific to the individual comprise parameters related to tumor dynamics, patient specific drug PK, and dynamics of dose-limiting host tissues.

Still preferably, said parameters related to tumor dynamics comprise age, weight, gender, percentage of limiting healthy cells, desired length of treatment protocol, previous reaction to treatment, molecular markers, genetic markers, pathologic specifics and cytologic specifics.

Yet another aspect of the present invention is a system for predicting the a progression of cancer in a general patients comprising a cancer system model, a plurality of treatment protocols for treating cancer using drugs, including chemotherapy; and a predictor to predict the progression of cancer under the plurality of treatment protocols based on the modified system model.

Preferably, the system model further comprises a realistic process model of cancer development; and a realistic treatment model that models the effects of treating cancer with drugs, including chemotherapy.

Still preferably, said process model incorporates a distribution of cycling cells and quiescent cells.

Still preferably, where a tumor cell cycle is divided into at least four compartments G1, S, G2 and M and a quiescent stage is denoted by G0, wherein each of said four compartments is further subdivided into sub-compartments and an ith sub-compartment representing cells of age I in the corresponding compartment, wherein cells entering a compartment always enter a first sub-compartment of the compartment.

Still preferably, the model traces development of cancer cells using a predetermined set of parameters by calculating a number of cells in each subcompartment using stepwise equations.

Still preferably, a probability vector is used to determine a fraction of cells that leaves any subcompartment in a compartment to move to a first subcompartment of the next compartment.

Still preferably, a set control functions uniquely determine an outcome of every single step, wherein said control functions depend on age of cells, state of a current population and associated environment.

Still preferably, a tumor is modelled as a combination of a plurality of homogeneous group of cells, each of said homogeneous group of cells representing a similarly behaving group of cells distributed between all the cell-cycle compartments.

Still preferably, in each step, a number of cells in each sub-compartment of each compartment of each group is calculated according to factors including a previous state, parameters of tumor, tumor current microenvironment and drug concentration.

Still preferably, spatial structure of the tumor is included in the model.

Still preferably, PK and PD, cytotoxic effects and cytostatic effects of anticancer drugs are incorporated into the model.

Still preferably, a dose-limiting toxicity is incorporated into the model.

Yet another aspect of the present invention is a method of recommending an optimal treatment protocol for an individual comprising: creating a system model; enumerating a plurality of treatment protocols; modifying the system model based on parameters specific to the individual; and selecting an optimal treatment protocol from said plurality of treatment protocols based on the modified system model.

Preferably, the step of creating the system model further comprises: modelling a biological process; and realistically modelling effects of a treatment on said biological process.

Still preferably, said modelling of biological processes is done by to mathematical modelling biological processes affecting healthy cell populations and mathematically modelling biological processes affecting cell populations with at least one disease.

Still preferably, said healthy cell populations include bone-marrow cells and host tissue cells that are affected by said treatment model.

Still preferably, said cell populations with at least one disease is one of cancer cells, and diseased bone-marrow cells including diseased Neutrophil cells and diseased Thrompocyte cells.

Still preferably, said treatment models comprise treatment specific processes that affect cell population.

Still preferably, said treatment specific process is interactions involving at least one of a group comprising pharmacokinetic (PK), pharmacodynamic (PD), cytostatic, cytotoxic, and methods of affecting cell biology and causing cell death, with associated biological processes.

Still preferably, said parameters specific to the individual include one or more selected from a group consisting of parameters related to the biological process' dynamics, patient specific drug PK, PD and dynamics of dose-limiting host tissues Still preferably, said parameters related to biological process' dynamics comprise age, weight, gender, blood picture, desired length of treatment protocol, previous reaction to treatment, molecular markers, genetic markers, pathologic specifics and cytologic specifics.

Still preferably, user-specific parameters are used in selecting the optimal treatment.

Still preferably, a fitness function is used to perform the selection.

Still preferably, said fitness function incorporates at least one parameter selected from a group consisting patient survival, time to death, time to reach a specified disease stage and cure, tumor load, pathogen load, cytotoxicity, side effects, quality of life, cost of treatment and pain.

Still preferably, a user can input specific coefficients for said at least one parameter to adjust the fitness function to satisfy the user's goals.

Still preferably, the user-specific parameters are based on a user, said user being a medical doctor.

Still preferably, the user-specific parameters are based on a user, said user being a scientist.

Still preferably, the user-specific parameters are based on a user, said user being a drug developer.

Preferably, said selection of treatment protocols incorporate cytotoxic effects.

Still preferably, said selection of treatment protocols incorporate drug efficacy.

Still preferably, operation research techniques are used in performing the selection.

Still preferably, heuristics are used to perform searching and selection.

Still preferably, said heuristics comprise computational feasibility.

Still preferably, said recommendation is a combination of disease and treatment strategy, including type of treatment, device, drug or drug combination, radiotherapy, surgery and treatment schedule and dosage.

Yet another aspect of the present invention is a method of recommending an optimal treatment protocol for a general patient comprising: creating a system model; enumerating a plurality of treatment protocols; and selecting an optimal treatment protocol from said plurality of treatment protocols based on the modified system model.

Still preferably, the step of creating the system model further comprises: modelling a biological process; and realistically modelling effects of a treatment on said biological process;

Still preferably, said modelling of biological processes is done by mathematical modelling biological processes affecting healthy cell populations and mathematically modelling biological processes affecting cell populations with at least one disease.

Still preferably, said healthy cell populations include bone-marrow cells and host tissue cells that are affected by said treatment model.

Still preferably, said cell populations with at least one disease is one of cancer cells, and diseased bone-marrow cells including diseased Neutrophil cells and diseased Thrompocyte cells.

Still preferably, said treatment models comprise treatment specific processes that affect cell population.

Still preferably, said treatment specific process is interactions involving one of a group comprising pharmacokinetic, pharmacodynamic, cytostatic, cytotoxic, or any other method of affecting cell biology and causing cell death, with associated biological processes.

Still preferably, user-specific parameters are used in selecting the optimal treatment.

Still preferably, a fitness function is used to perform the selection.

Still preferably, said fitness function incorporates at least one parameter selected from a group comprising patient survival, time to death, time to reach a specified disease stage (including cure)e, tumor load, pathogen load, cytotoxicity, side effects, quality of life, cost of treatment and pain.

Still preferably, a user can input specific coefficients for said at least one parameter to adjust the fitness function to satisfy the user's goals.

Still preferably, the user-specific parameters are based on a user, said user being a medical doctor.

Still preferably, the user-specific parameters are based on a user, said user being a scientist.

Still preferably, the user-specific parameters are based on a user, said user being a drug developer.

Still preferably, said selection of treatment protocols incorporate cytotoxic effects.

Still preferably, said selection of treatment protocols incorporate drug efficacy.

Still preferably, operation research techniques are used in performing the selection.

Still preferably, heuristics are used to perform searching and selection.

Still preferably, said heuristics comprise computational feasibility.

Still preferably, said recommendation is a combination of disease and treatment strategy, including type of treatment, device, drug, drug combination, radiotherapy, surgery and treatment schedule and dosage.

Yet another aspect of the present invention is a method of predicting progression of a biological process in an individual patient under a plurality of treatment protocols, wherein said biological process could be related to healthy or diseased processes, said plurality of protocols including no treatment, said method comprising creating a system model, enumerating a plurality of treatment protocols; modifying the system model based on parameters specific to the individual, and selecting an optimal treatment protocol from said plurality of treatment protocols based on the modified system model.

Preferably, the step of creating a system model further comprises: realistically modelling a biological process; and realistically modelling the effects of the treatment on said biological process.

Still preferably, said step of modelling a biological process comprises creating a mathematical model for biological processes affecting healthy cell populations and creating a biological processes affecting cell populations with at least one disease.

Still preferably, said healthy cell populations include bone-marrow cells and host tissue cells that are affected by said treatment model.

Still preferably, said cell populations with at least one disease is one of cancer cells, and diseased bone-marrow cells including diseased Neutrophil cells and diseased Thrombocyte cells.

Still preferably, said treatment models comprise treatment specific processes that affect cell population.

Still preferably, said treatment specific process is interactions involving one of a group comprising PK, PD, cytostatic, cytotoxic, or any other method of affecting cell biology and causing cell death, with associated biological processes.

Still preferably, said parameters specific to the individual include one or more selected from a group consisting of parameters related to the biological process' dynamics, patient specific drug PK, PD and dynamics of dose-limiting host tissues.

Still preferably, said parameters related to biological process' dynamics comprise age, weight, gender, blood picture, desired length of treatment protocol, previous reaction to treatment, molecular markers, genetic markers, pathologic specifics and cytologic specifics.

Yet another aspect of the present invention is a method of predicting progression of a biological process in a general patient under a plurality of treatment protocols, wherein said biological process could be related to healthy or diseased, said plurality of protocols including no treatment, said method comprising creating a system model; enumerating a plurality of treatment protocols; and selecting an optimal treatment protocol from said plurality of treatment protocols based on the modified system model.

Preferably, the step of creating a system model further comprises realistically modelling a biological process; and realistically modelling the and the effects of the treatment on said biological process.

Still preferably, said step of modelling a biological process comprises creating a mathematical model for biological processes affecting healthy cell populations and creating a biological processes affecting cell populations with at least one disease.

Still preferably, said healthy cell populations include bone-marrow cells and host tissue cells that are affected by said treatment model.

Still preferably, said cell populations with at least one disease is one of cancer cells, and diseased bone-marrow cells including at least one of diseased Neutrophil cells and diseased Thrombocyte cells.

Still preferably, said treatment models comprise treatment specific processes that affect cell population.

Still preferably, said treatment specific process is interactions involving one of a group comprising PK, PD, drug cytostatics, drug cytotoxics, and methods of affecting cell biology and causing cell death, with associated biological processes.

Yet another aspect of the present invention is a method for modelling Thrombopietic lineage in an individual, said method comprising: realistically modelling a process to create a process model for cells involved in Thrombopoiesis; and modifying the process model based on parameters specific to the individual.

Preferably, a realistic progression of cells involved in diseased Thrombopoiesis is incorporated in the process model.

Still preferably, diseased Thrombopoiesis includes Thrombocytopenia.

Still preferably, effects of at least one drug in the realistic progression of cells involved in Thrombopoiesis is incorporated.

Still preferably, said at least one drug is Thrombopoietin (TPO).

Still preferably, said process model imitates a course of the individual's bone marrow progression, peripheral platelet counts and TPO concentration changes.

Still preferably, said process model incorporates cell-suppressive treatment effects and administration of TPO to the patient.

Still preferably, said cell-suppressive treatment is chemotherapy.

Preferably, said method is used for recommending an optimum treatment protocol, and wherein said method further comprises: enumerating a plurality of treatment protocols; and selecting an optimal treatment protocol from said plurality of treatment protocols based on the modified system model.

Yet another aspect of the present invention is a method for modelling Thrombopietic lineage in a general patient, said method comprising: realistically modelling a process to create a process model for cells involved in Thrombopoiesis.

Preferably, a realistic progression of cells involved in diseased thrombopoiesis is incorporated in the process model.

Still preferably, diseased Thrombopoiesis includes Thrombocytopenia.

Still preferably, effects of at least one drug in the realistic progression of cells involved in Thrombopoiesis is incorporated.

Still preferably, said at least one drug is Thrombopoietin (TPO).

Still preferably, said process model imitates a course of the individual's bone marrow progression, peripheral platelet counts and TPO concentration changes.

Still preferably, said process model incorporates cell-suppressive treatment effects and administration of TPO to the patient.

Still preferably, said cell-suppressive treatment is chemotherapy.

Preferably, said method is used for recommending an optimum treatment protocol, and wherein said method further comprises: enumerating a plurality of treatment protocols; and selecting an optimal treatment protocol from said plurality of treatment protocols based on the modified system model.

Yet another aspect of the present invention is a method for predicting progression of Thrombopoiesis and Thrombocytopenia for an individual under a plurality of treatment protocols, said plurality of protocols including no treatment, said method comprising: creating a realistic model of Thrombopoiesis and Thrombocytopenia; generating a plurality of treatment protocols for affecting Thrombopoiesis and treating Thrombocytopenia using at least one drug;

modifying the model based on parameters specific to the individual; and predicting the progression of the disease or the natural biological process under said plurality of treatment protocols based on the modified system model.

Preferably, the model incorporates a realistic progression of cells involved in diseased Thrombopoiesis.

Still preferably, diseased Thrombopoiesis includes Thrombocytopenia.

Still preferably, the model incorporates effects of at least one drug in the realistic progression of cells involved in Thrombocytopenia.

Still preferably, said at least one drug is Thrombopoietin (TPO).

Still preferably, the model imitates a course of the individual's bone marrow progression, peripheral platelet counts and TPO concentration changes.

Still preferably, the model incorporates cell-suppressive treatment effects and administration of TPO to the patient.

Still preferably, said cell-suppressive treatment is chemotherapy.

Still preferably, said process model further comprises a plurality of compartments.

Still preferably, said compartments include:

a stem cell (SC) compartment that comprises bone marrow haemopoietic progenitors that have an ability to differentiate into more than one cell line wherein cells in the stem cell compartment proliferate and differentiate into one of megakaryocyte;

a colony forming units-megakaryocytes (CFU-Meg) compartment, wherein the megakaryocyte progenitors get committed as a megakaryocyte line and spend some time multiplying and maturing;

a megakaryoblast (MKB) compartment, which receives the cells from CFU-Meg, wherein the cells in the MKB compartment have lost their ability to proliferate but are not mature to release platelets;

a MK16 compartment, which receives cell from the MKB compartment, wherein a subset of cells in the MK16 compartment release platelets at a constant rate until they exhaust their capacity and are disintegrated and a second subset of cells do not release platelets but continue with endomitosis;

a MK32 compartment that receives cells from the MK16 compartment, wherein a subset of cells in this compartment release platelets and a second subset of cells do not release platelets but continue with endomitosis;

a MK64 compartment that receives cells from the MK32 compartment wherein a subset of cells in this compartment release platelets and a second subset of cells do not release platelets but continue with endomitosis;

a MK128 compartment that receives cells from the MK64 compartment wherein a subset of cells in this compartment release platelets; and a platelets (PL) compartment.

Still preferably, an effect of apoptosis are included with an overall effect of cell proliferation in giving rise to an amplification of cell numbers in a corresponding compartment.

Still preferably, the model further incorporates the effects of TPO on the SC, CFU-Meg and MKB compartments.

Still preferably, the effects are expressed in terms of effects of TPO concentration on amplification rate, rate of cell maturation and a fraction of cells that undergo endomotisis.

Still preferably, when the TPO concentration is above a predetermined threshold level, the amplification rate of cells in the SC compartment are affected and below the threshold the amplification rate is dependent only on a current number of cells.

Still preferably, in the CFU-Meg compartment the cells are sensitive to TPO concentration regardless of the concentration of TPO.

Still preferably, the transit time is same in all platelet releasing compartments and the transit time of the SC, CFU-Meg and MKB compartments are functions of micro-environmental conditions.

Still preferably, in the SC compartment when the TPO concentration is above the threshold, the transit time is shortened based the dose.

Still preferably, in the CFU-Meg and MKB, the transit time is solely based on TPO concentration.

Still preferably, a fraction of cells in the SC compartment that commits to megakaryocytic lineage is constant and dependent on TPO.

Still preferably, in the CFU-Meg and MKB compartments, every mature cell passes on to the next compartment.

Still preferably, in the MK16, MK32 and MK64 compartments, a fraction of cells pass on to the next compartment, said fraction being dependent on the TPO concentration.

Still preferably, cells from MK128 compartment do not flow into any other compartment.

Still preferably, each of said compartments is further divided into sub-compartments, each of said sub-compartments containing cells of a specific age in hours.

Still preferably, cells that spend all their corresponding transit time in a given compartment pass on to the next compartment, wherein cells that have left a corresponding compartment each hour fill the first sub-compartment of the next compartment.

Still preferably, the platelet releasing cells contribute platelets to the first sub-compartment of the PL compartment.

Yet another aspect of the present invention is a method for predicting progression of Thrombopoiesis and Thrombocytopenia for a general patient under a plurality of treatment protocols, said plurality of protocols including no treatment, said method comprising: creating a realistic model Thrombopoiesis and Thrombocytopenia; generating a plurality of treatment protocols for affecting Thrombopoiesis and treating Thrombocytopenia using at least one drug; and predicting the progression of the disease or the natural biological process under said plurality of treatment protocols based on the modified system model.

Preferably, the model incorporates a realistic progression of cells involved in diseased Thrombopoiesis.

Still preferably, diseased Thrombopoiesis includes Thrombocytopenia.

Still preferably, the model incorporates effects of at least one drug in the realistic progression of cells involved in Thrombocytopenia.

Still preferably, said at least one drug is Thrombopoietin (TPO).

Still preferably, the model imitates a course of the individual's bone marrow progression, peripheral platelet counts and TPO concentration changes.

Still preferably, the model incorporates cell-suppressive treatment effects and administration of TPO to the patient.

Still preferably, said cell-suppressive treatment is chemotherapy.

Still preferably, said process model further comprises a plurality of compartments.

Still preferably, said compartments include:

a stem cell (SC) compartment that comprises bone marrow haemopoietic progenitors that have an ability to differentiate into more than one cell line wherein cells in the stem cell compartment proliferate and differentiate into one of megakaryocyte;

a colony forming units-megakaryocytes (CFU-Meg) compartment, wherein the megakaryocyte progenitors get committed as a megakaryocyte line and spend some time multiplying and maturing;

a megakaryoblast (MKB) compartment, which receives the cells from CFU-Meg, wherein the cells in the MKB compartment have lost their ability to proliferate but are not mature to release platelets;

a MK16 compartment, which receives cell from the MKB compartment, wherein a subset of cells in the MK16 compartment release platelets at a constant rate until they exhaust their capacity and are disintegrated and a second subset of cells do not release platelets but continue with endomitosis;

a MK32 compartment that receives cells from the MK16 compartment, wherein a subset of cells in this compartment release platelets and a second subset of cells do not release platelets but continue with endomitosis;

a MK64 compartment that receives cells from the MK32 compartment wherein a subset of cells in this compartment release platelets and a second subset of cells do not release platelets but continue with endomitosis;

a MK128 compartment that receives cells from the MK64 compartment wherein a subset of cells in this compartment release platelets; and a platelets (PL) compartment.

Still preferably, an effect of apoptosis are included with an overall effect of cell proliferation in giving rise to an amplification of cell numbers in a corresponding compartment.

Still preferably, the model further incorporates the effects of TPO on the SC, CFU-Meg and MKB compartments.

Still preferably, the effects are expressed in terms of effects of TPO concentration on amplification rate, rate of cell maturation and a fraction of cells that undergo endomotisis.

Still preferably, when the TPO concentration is above a predetermined threshold level, the amplification rate of cells in the SC compartment are affected and below the threshold the amplification rate is dependent only on a current number of cells.

Still preferably, in the CFU-Meg compartment the cells are sensitive to TPO concentration regardless of the concentration of TPO.

Still preferably, the transit time is same in all platelet releasing compartments and the transit time of the SC, CFU-Meg and MKB compartments are functions of micro-environmental conditions.

Still preferably, in the SC compartment when the TPO concentration is above the threshold, the transit time is shortened based the dose.

Still preferably, in the CFU-Meg and MKB, the transit time is solely based on TPO concentration.

Still preferably, a fraction of cells in the SC compartment that commits to megakaryocytic lineage is constant and dependent on TPO.

Still preferably, in the CFU-Meg and MKB compartments, every mature cell passes on to the next compartment.

Still preferably, in the MK16, MK32 and MK64 compartments, a fraction of cells pass on to the next compartment, said fraction being dependent on the TPO concentration.

Still preferably, cells from MK128 compartment do not flow into any other compartment.

Still preferably, each of said compartments is further divided into sub-compartments, each of said sub-compartments containing cells of a specific age in hours.

Still preferably, cells that spend all their corresponding transit time in a given compartment pass on to the next compartment, wherein cells that have left a corresponding compartment each hour fill the first sub-compartment of the next compartment.

Still preferably, the platelet releasing cells contribute platelets to the first sub-compartment of the PL compartment.

Yet another aspect of the present invention is a method for modelling Neutrophil lineage for an individual, said method comprising: creating a realistic a Neutrophil system model including a realistic process model for cells involved in Neutrophil lineage; and modifying the system model based on parameters specific to the individual.

Preferably, the system model incorporates a realistic progression of cells involved in Granulopoietic disorders, including Neutropenia.

Still preferably, the system model incorporates effects of at least one drug in the realistic progression of cells involved in Granulopoiesis and Neutropenia.

Still preferably, said at least one drug is Granulocyte Colony Stimulating Factor (G-CSF).

Still preferably, said system model comprises at least three stages,
a first stage related to an administered amount of cytokine;
a second stage representing a pharmacokinetic behavior of G-CSF; and
a third stage representing a pharmacodynamic effect of G-CSF on kinetic parameters of the system.

Still preferably, said model comprises a mitotic compartment, and a post mitotic compartment, said mitotic compartment being divided into is subcompartments wherein a kth sub-compartment contains cells of age between k−1 and k hours relative to a time of entry into the mitotic compartment.

Still preferably, effects of toxic drugs, including chemotherapy are incorporated by mapping various cell-cycle phases to the sub-compartments and formulating a function of cytotoxic effects of toxic drugs, including chemotherapy on the cell-cycle phases.

Still preferably, the effects of G-CSF on the mitotic compartment are modeled as an increase in a rate of cells entering the myeloblasts compartment from an uncommitted stem cell pool.

Still preferably, the post-mitotic compartment is modeled as a single pool of cells wherein cells in a last sub-compartment of the mitotic compartment enters the post-mitotic compartment and a proportion of cells within the post-mitotic compartment enters the mature Neutrophil pool every hour.

Still preferably, effects of G-CSF on the Neutrophil lineage are modeled as a decrease in the cells in the post-mitotic compartment which is subsequently compensated by an increased production in the mitotic compartment, said compensation sustaining an increase in Neutrophil count.

Still preferably, an elimination of Neutrophils in the post-mitotic compartment is represented by a Poisson distribution.

Still preferably, the cytotoxic effects of toxic drugs, including chemotherapy in the post-mitotic compartment is modeled as an effect on a single pool of cells.

Still preferably, kinetic of G-CSF is modeled as an exponential distribution.

Still preferably, a selection of an optimal treatment uses an objective function that aims at minimizing G-CSF administration and returning Neutrophil lineage to normal levels.

Still preferably, selection is performed using linear programming.

Still preferably, pharmacokinetics and pharmacodynamics of G-CSF are defined using piecewise linear functions.

Preferably, said method is used for recommending an optimum treatment protocol, and wherein said method further comprises: enumerating a plurality of treatment protocols; and selecting an optimal treatment protocol from said plurality of treatment protocols based on the modified system model.

Yet another aspect of the present invention is a method for modelling Neutrophil lineage for a general patient, said method comprising: creating a realistic a Granulopoiesis system model including a realistic process model for cells involved in Granulopoiesis lineage.

Preferably the system model incorporates a realistic progression of cells involved in Granulopoietic disorders, including Neutropenia.

Still preferably, the system model incorporates effects of at least one drug in the realistic progression of cells involved Granulopoiesis and in Neutropenia.

Still preferably, said at least one drug is Granulocyte Colony Stimulating Factor (G-CSF).

Still preferably, said system model comprises at least three stages,
a first stage related to an administered amount of cytokine;
a second stage representing a pharmacokinetic behavior of G-CSF; and
a third stage representing a pharmacodynamic effect of G-CSF on kinetic parameters.

Preferably, wherein said model comprises a mitotic compartment, and a post mitotic compartment, said mitotic compartment being divided into subcompartments wherein a kth sub-compartment contains cells of age between k−1 and k hours relative to a time of entry into the mitotic compartment.

Still preferably, effects of toxic drugs, including chemotherapy are incorporated by mapping various cell-cycle phases to the sub-compartments and formulating a function of cytotoxic effects of toxic drugs, including chemotherapy on the cell-cycle phases.

Still preferably, the effects of G-CSF on the mitotic compartment are modeled as an increase in a rate of cells entering the myeloblasts compartment from an uncommitted stem cell pool.

Still preferably, the post-mitotic compartment is modeled as a single pool of cells wherein cells in a last sub-compartment of the mitotic compartment enters the post-mitotic compartment and a proportion of cells within the post-mitotic compartment enters the mature Neutrophil pool every hour.

Still preferably, effects of G-CSF on the Neutrophil lineage are modeled as a decrease in the cells in the post-mitotic compartment which is subsequently compensated by an increased production in the mitotic compartment, said compensation sustaining an increase in Neutrophil count.

Still preferably, an elimination of Neutrophils in the post-mitotic compartment is represented by a Poisson distribution.

Still preferably, the cytotoxic effects of toxic drugs, including chemotherapy in the post-mitotic compartment is modeled as an effect on a single pool of cells.

Still preferably, kinetic of G-CSF is modeled as an exponential distribution.

Still preferably, a selection of an optimal treatment uses an objective function that aims at minimizing G-CSF administration and returning Neutrophil lineage to normal levels.

Still preferably, said selection is performed using linear programming.

Still preferably, pharmacokinetics and pharmacodynamics of G-CSF are defined using piecewise linear functions.

Still preferably, said method is used for recommending an optimum treatment protocol, and wherein said method further comprises: enumerating a plurality of treatment protocols; and selecting an optimal treatment protocol from said plurality of treatment protocols based on the modified system model.

Yet another aspect of the present invention is a method for predicting progression of Granulopoiesis for an individual under a plurality of treatment protocols, said plurality of protocols including no treatment, said system comprising: creating a Neutrophil system model including a realistic process model for cells involved in Neutrophil production; generating a plurality of treatment protocols; modifying the system model modifier, wherein said Neutrophil system model is modified by the system model modifier based on parameters specific to the individual; and predicting the progression under the plurality of treatment protocols based on the modified system model.

Preferably, the system model incorporates a realistic progression of cells involved in Granulopoietic disorders, including Neutropenia.

Still preferably, the system incorporates effects of at least one drug in the realistic progression of cells involved in Granulopoiesis and Neutropenia.

Still preferably, said at least one drug is Granulocyte Colony Stimulating Factor (G-CSF).

Still preferably, said model comprises at least three stages,
a first stage related to an administered amount of cytokine;
a second stage representing a pharmacokinetic behavior of G-CSF; and
a third stage representing a pharmacodynamic effect of G-CSF on kinetic parameters.

Still preferably, said model comprises a mitotic compartment, and a post mitotic compartment, said mitotic compartment being divided into subcompartments wherein a kth sub-compartment contains cells of age between k–1 and k hours relative to a time of entry into the mitotic compartment.

Still preferably, effects of toxic drugs, including chemotherapy are incorporated by mapping various cell-cycle phases to the sub-compartments and formulating a function of cytotoxic effects of toxic drugs, including chemotherapy on the cell-cycle phases.

Still preferably, the effects of G-CSF on the mitotic compartment are to modeled as an increase in a rate of cells entering the myeloblasts compartment from an uncommitted stem cell pool.

Still preferably, the post-mitotic compartment is modeled as a single pool of cells wherein cells in a last sub-compartment of the mitotic compartment enters the post-mitotic compartment and a proportion of cells within the post-mitotic compartment enters the mature Neutrophil pool every hour.

Still preferably, effects of G-CSF on the Neutrophil lineage are modeled as a decrease in the cells in the post-mitotic compartment which is subsequently compensated by an increased production in the mitotic compartment, said compensation sustaining an increase in Neutrophil count.

Still preferably, an elimination of Neutrophils in the post-mitotic compartment is represented by a Poisson distribution.

Still preferably, the cytotoxic effects of toxic drugs, including chemotherapy in the post-mitotic compartment is modeled as an effect on a single pool of cells.

Still preferably, kinetic of G-CSF is modeled as an exponential distribution.

Preferably, a selection of an optimal treatment uses an objective function that aims at minimizing G-CSF administration and returning Neutrophil lineage to normal levels.

Still preferably, said selection is performed using linear programming.

Still preferably, pharmacokinetics and pharmacodynamics of G-CSF are defined using piecewise linear functions.

Yet another aspect of the present invention is a method for predicting progression of Granulopoiesis for a general patient under a plurality of treatment protocols, said plurality of protocols including no treatment, said system comprising: creating a Neutrophil system model including a realistic process model for cells involved in Neutrophil production; generating a plurality of treatment protocols; and predicting the progression under the plurality of treatment protocols based on the modified system model.

Still preferably, the system model incorporates a realistic progression of cells involved in Granulopoietic disorders, including Neutropenia.

Still preferably, the system incorporates effects of at least one drug in the realistic progression of cells involved in Granulopoiesis and Neutropenia.

Still preferably, said at least one drug is Granulocyte Colony Stimulating Factor (G-CSF).

Still preferably, said model comprises at least three stages,
a first stage related to an administered amount of cytokine;
a second stage representing a pharmacokinetic behavior of G-CSF; and
a third stage representing a pharmacodynamic effect of G-CSF on kinetic parameters.

Still preferably, said model comprises a mitotic compartment, and a post mitotic compartment, said mitotic compartment being divided into subcompartments wherein a kth sub-compartment contains cells of age between k–1 and k hours relative to a time of entry into the mitotic compartment.

Still preferably, effects of toxic drugs, including chemotherapy are incorporated by mapping various cell-cycle phases to the sub-compartments and formulating a function of cytotoxic effects of toxic drugs, including chemotherapy on the cell-cycle phases.

Still preferably, the effects of G-CSF on the mitotic compartment are modeled as an increase in a rate of cells entering the myeloblasts compartment from an uncommitted stem cell pool.

Still preferably, the post-mitotic compartment is modeled as a single pool of cells wherein cells in a last sub-compartment of the mitotic compartment enters the post-mitotic compartment and a proportion of cells within the post-mitotic compartment enters the mature Neutrophil pool every hour.

Still preferably, effects of G-CSF on the Neutrophil lineage are modeled as a decrease in the cells in the post-mitotic compartment which is subsequently compensated by an increased production in the mitotic compartment, said compensation sustaining an increase in Neutrophil count.

Still preferably, an elimination of Neutrophils in the post-mitotic compartment is represented by a Poisson distribution.

Still preferably, the cytotoxic effects of toxic drugs, including chemotherapy in the post-mitotic compartment is modeled as an effect on a single pool of cells.

Still preferably, kinetic of G-CSF is modeled as an exponential distribution.

Still preferably, a selection of an optimal treatment uses an objective function that aims at minimizing G-CSF administration and returning Neutrophil lineage to normal levels.

Still preferably, said selection is performed using linear programming.

Still preferably, pharmacokinetics and pharmacodynamics of G-CSF are defined using piecewise linear functions.

Yet another aspect of the present invention a method for recommending an optimal treatment protocol for treating cancer using drugs, including chemotherapy, for an individual, said method comprising: creating a cancer system model; enumerating a plurality of treatment protocols for treating cancer using drugs, including chemotherapy; modifying the system model based on parameters specific to the individual; and selecting an optimal treatment protocol from said plurality of treatment protocols based on the modified system model.

Preferably, the system model further comprises: a realistic process model of cancer development; and a realistic treatment model that models the effects of treating cancer with drugs, including chemotherapy.

Still preferably, said process model incorporates a distribution of cycling cells and quiescent cells.

Still preferably, where a tumor cell cycle is divided into at least four compartments G1, S, G2 and M and a quiescent stage is denoted by G0, wherein each of said four compartments is further subdivided into sub-compartments and an ith sub-compartment representing cells of age I in the corresponding compartment, wherein cells entering a compartment always enter a first sub-compartment of the compartment.

Still preferably, the model traces development of cancer cells using a predetermined set of parameters by calculating a number of cells in each subcompartment using stepwise equations.

Still preferably, a probability vector is used to determine a fraction of cells that leaves any subcompartment in a compartment to move to a first subcompartment of the next compartment.

Still preferably, a set of control functions uniquely determine an outcome of every single step, wherein said control functions depend on age of cells, state of a current population and associated environment.

Still preferably, a tumor is modelled as a combination of a plurality of homogeneous group of cells, each of said homogeneous group of cells representing a similarly behaving group of cells distributed between all the cell-cycle compartments.

Still preferably, in each step, a number of cells in each sub-compartment of each compartment of each group is calculated according to factors including a previous state, parameters of tumor, tumor current microenvironment and drug concentration.

Still preferably, spatial structure of the tumor is included in the model.

Still preferably, PK and PD, cytotoxic effects, cytostatic effects and other effects on cell disintegration of anticancer drugs are incorporated into the model.

Still preferably, a dose-limiting toxicity is incorporated into the model.

Still preferably, said parameters specific to the individual comprise parameters related to tumor dynamics, patient specific drug PK, and dynamics of dose-limiting host tissues.

Still preferably, said parameters related to tumor dynamics comprise age, weight, gender, percentage of limiting healthy cells, desired length of treatment protocol, previous reaction to treatment, molecular markers, genetic markers, pathologic specifics and cytologic specifics.

Yet another aspect of the present invention is a method of predicting a progression of cancer in an individual, said method comprising: creating a cancer system model; enumerating a plurality of treatment protocols for treating cancer using drugs, including chemotherapy; modifying the system model based on parameters specific to the individual; and selecting an optimal treatment protocol from said plurality of treatment protocols based on the modified system model.

Preferably, the system model further comprises: a realistic process model of cancer development; and a realistic treatment model that models the effects of treating cancer with drugs, including chemotherapy.

Still preferably, said process model incorporates a distribution of cycling cells and quiescent cells.

Still preferably, a tumor cell cycle is divided into at least four compartments G1, S, G2 and M and a quiescent stage is denoted by G0, wherein each of said four compartments is further subdivided into sub-compartments and an ith sub-compartment representing cells of age I in the corresponding compartment, wherein cells entering a compartment always enter a first sub-compartment of the compartment.

Still preferably, the model traces development of cancer cells using a predetermined set of parameters by calculating a number of cells in each subcompartment using stepwise equations.

Still preferably, a probability vector is used to determine a fraction of cells that leaves any subcompartment in a compartment to move to a first subcompartment of the next compartment.

Still preferably, a set control functions uniquely determine an outcome of every single step, wherein said control functions depend on age of cells, state of a current population and associated environment.

Still preferably, a tumor is modelled as a combination of a plurality of homogeneous group of cells, each of said homogeneous group of cells representing a similarly behaving group of cells distributed between all the cell-cycle compartments.

Still preferably, in each step, a number of cells in each sub-compartment of each compartment of each group is calculated according to factors including a previous state, parameters of tumor, tumor current microenvironment and drug concentration.

Still preferably, spatial structure of the tumor is included in the model.

Still preferably, PK and PD, cytotoxic and other cell disintegration effects, and cytostatic effects of anticancer drugs are incorporated into the model.

Still preferably, a dose-limiting toxicity is incorporated into the model.

Still preferably, said parameters specific to the individual comprise parameters related to tumor dynamics, patient specific drug PK, and dynamics of dose-limiting host tissues.

Still preferably, said parameters related to tumor dynamics comprise age, weight, gender, percentage of limiting healthy cells, desired length of treatment protocol, previous reaction to treatment, molecular markers, genetic markers, pathologic specifics and cytologic specifics.

Yet another aspect of the present invention is a method of predicting a progression of cancer in a general patient, said method comprising: creating a cancer system model; enumerating a plurality of treatment protocols for treating cancer using drugs, including chemotherapy; and selecting an optimal treatment protocol from said plurality of treatment protocols based on the modified system model.

Still preferably, the system model further comprises: a realistic process model of cancer development; and a realistic treatment model that models the effects of treating cancer with drugs, including chemotherapy.

Still preferably, said process model incorporates a distribution of cycling cells and quiescent cells.

Still preferably, a tumor cell cycle is divided into at least four compartments G1, S, G2 and M and a quiescent stage is denoted by G0, wherein each of said four compartments is further subdivided into sub-compartments and an ith sub-compartment representing cells of age I in the corresponding compartment, wherein cells entering a compartment always enter a first sub-compartment of the compartment.

Still preferably, the model traces development of cancer cells using a predetermined set of parameters by calculating a number of cells in each subcompartment using stepwise equations.

Still preferably, a probability vector is used to determine a fraction of cells that leaves any subcompartment in a compartment to move to a first subcompartment of the next compartment.

Still preferably, a set control functions uniquely determine an outcome of every single step, wherein said control functions depend on age of cells, state of a current population and associated environment.

Still preferably, a tumor is modelled as a combination of a plurality of homogeneous group of cells, each of said homogeneous group of cells representing a similarly behaving group of cells distributed between all the cell-cycle compartments.

Still preferably, in each step, a number of cells in each sub-compartment of each compartment of each group is calculated according to factors including a previous state, parameters of tumor, tumor current microenvironment and drug concentration.

Still preferably, spatial structure of the tumor is included in the model.

Still preferably, PK and PD, cytotoxic effects and cytostatic effects of anticancer drugs are incorporated into the model.

Still preferably, a dose-limiting toxicity is incorporated into the model.

Yet another aspect of the present invention is a computer program product, including a computer readable medium, said program product comprising a set of instruction to enable a computer system to aid in recommending an optimal treatment protocol for an individual comprising:

a system model code; treatment protocol code for a plurality of treatment protocols;

a system model modifier code, wherein said system model is modified by the system model modifier based on parameters specific to the individual; and a selector code to select an optimal treatment protocol from said plurality of treatment protocols based on the modified system model.

Preferably, the system model code further comprises: a realistic biological process model code; and a realistic treatment model code that enables a computer to model the effects of a treatment on the biological process.

Yet another aspect of the present invention is a computer program product, including a computer readable medium, said program product comprising a set of instructions to enable a computer system to aid in recommending an optimal treatment protocol for a general patient comprising: a system model code; treatment protocol code for a plurality of treatment protocols; and a selector code to select an optimal treatment protocol from said plurality of treatment protocols based on the modified system model.

Preferably, the system model code further comprises: a realistic biological process model code; and a realistic treatment model code that enables a computer to model the effects of a treatment on the biological process.

III. BRIEF DESCRIPTION OF THE DRAWINGS

The present invention will be understood and appreciated more fully from the following detailed description taken in conjunction with the appended drawings in which:

FIG. 1 is a schematic illustration of the basis of the present invention;

FIGS. 2A and B are diagram charts illustrating steps of the invention, useful in understanding FIG. 1; FIG. 2A further illustrates a protocol space;

FIG. 4 is a chart illustration of the biological model of FIG. 3;

FIGS. 8A and 8B are graphical illustrations of the output of the model of FIG. 3;

FIGS. 9A and 9B are graphical illustrations of experimental data as compared to the output shown in FIGS. 8A and 8B;

IV. DETAILED DESCRIPTION OF THE PRESENT INVENTION

Systems and methods have been disclosed for identifying optimal treatment strategies for a general patient and a specific individual patient, and for predicting progression of a biological process and treatment, using selected parameters. The techniques are based on biological and clinical knowledge, mathematical models, computer simulations, and optimization methods. The optimization techniques could be any available mathematical techniques including, but not limited to, linear programming and heuristic search. The disclosed heuristic search techniques use heuristic (or rules of thumb) determinations.

Such a use of heuristics search enables the user to find near optimal solutions even for complex mathematical descriptions of a combination of relevant biological, clinical, pharmacological scenarios. These complex mathematical descriptions are contemplated to be realistic simulations of actual scenarios. It is contemplated that this holds both for the general case ("optimal generic treatment"), as well as at the level of an individual patient.

The general case is intended for several purposes including use by pharmaceutical companies and by researches who are more concerned with designing systems and recommending treatment for a general patient as opposed to recommending treatment for a specific patient in a clinical setting. It is also contemplated that the general case can be used for a better understanding of the underlying processes for any other use. Likewise, the individual case is intended for several purposes including, for example, the use by a doctor to understand the progress of a treatment protocol or the progression of a disease, and to optimize the treatment for a specific individual patient. These indicated uses are not intended to be restrictive. It should be clear to the skilled practitioner that the techniques disclosed can be put to several other uses.

Figure 1:
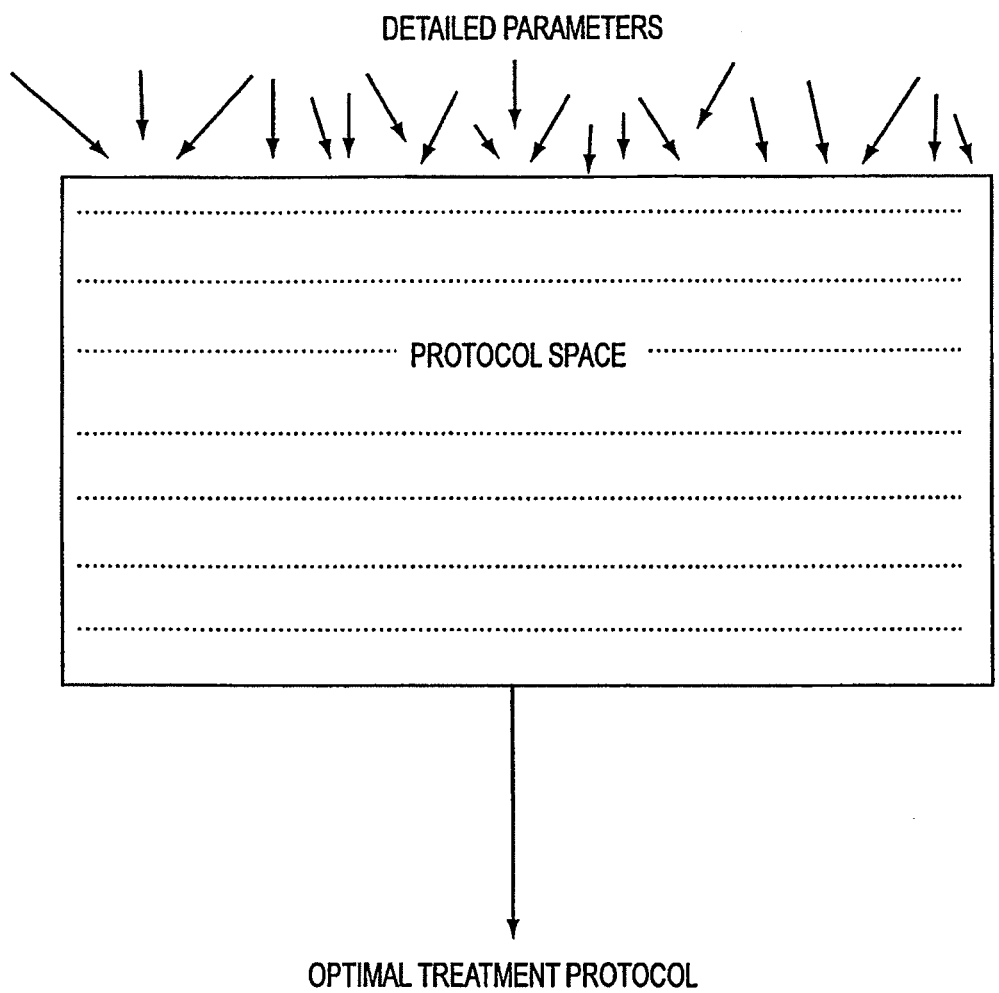

FIG. 1 illustrates the general concept behind the disclosed technique. Detailed parameters are input to a protocol space. The protocol space comprises a plurality of treatment protocols. From this protocol space an optimal treatment protocol is selected by performing a heuristic search.

Figure 2A:
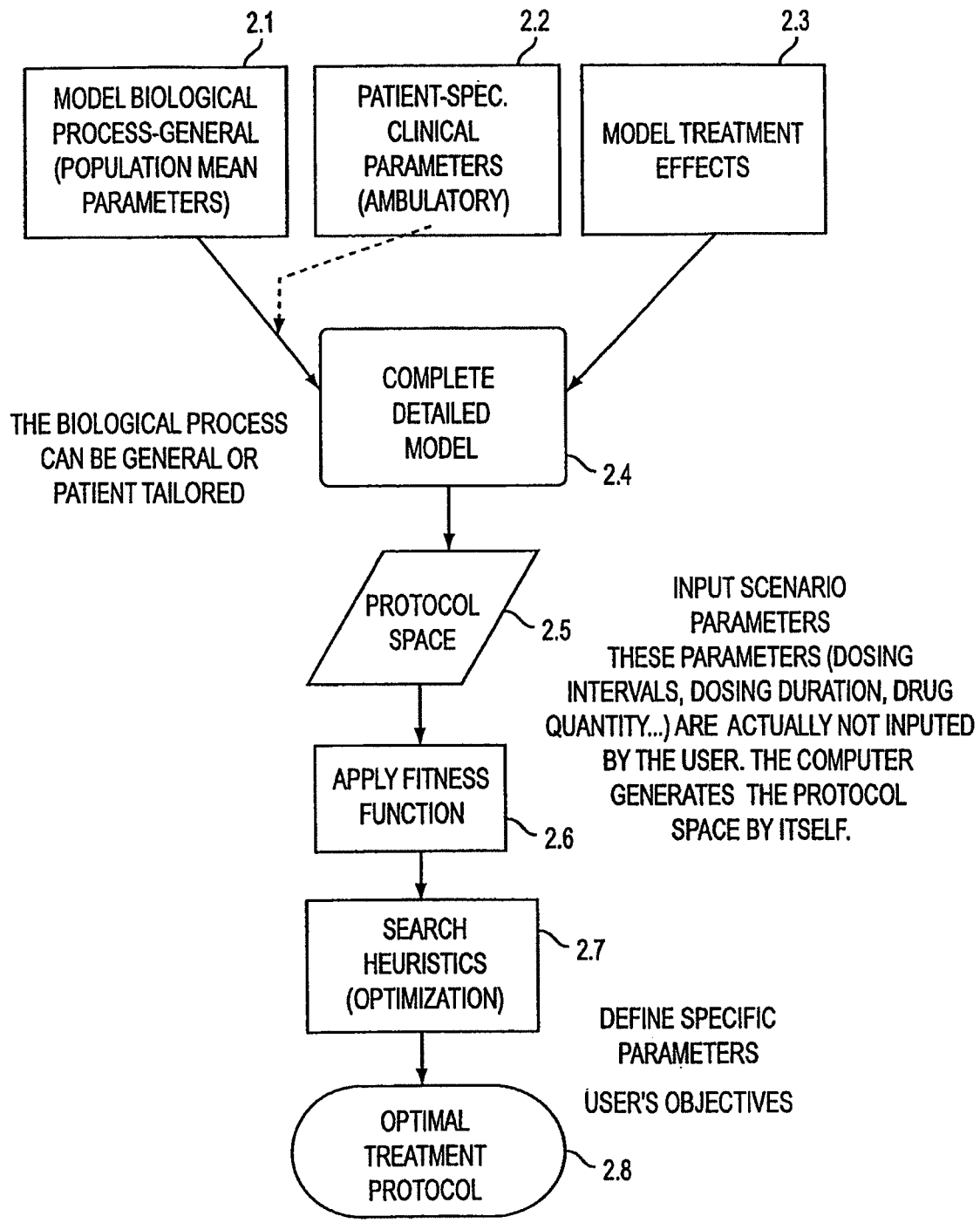
Figure 2B:
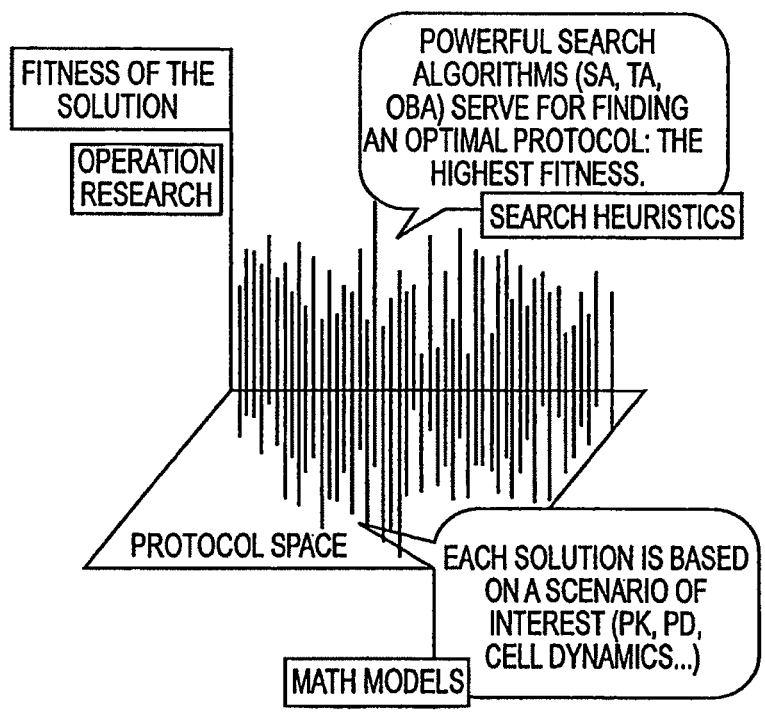

FIG. 2 shows a diagram chart that depicts an illustration of an embodiment of the disclosed techniques for optimization. The Figure generally depicts the basic concept. The disclosed techniques are used to optimize a drug delivery protocol after consideration of a plurality of possible protocols. The plurality of protocols together form a protocol space 2.5. Determination of an optimal protocol is partially based on specific parameters input by a user. The user may be a physician, a drug developer, a scientist, or anyone else who may need to determine a treatment strategy, needs of a specific user and other particulars such as patient survival, efficacy, time to death, time to reach a specified disease stage (including cure), tumor load, pathogen load, cytotoxicity, side effects, quality of life, cost of treatment, and pain. maximum length of treatment, confidence level, etc. In case of the disclosed techniques for the individual patient, general characteristic parameters which determine the system's behaviour, are altered according to individual patient characteristics and/or medical history of the patient.

Initially, system models are created. These included models to simulate all the relevant biological, clinical and pharmaceutical process 2.1. These models include mathematical models for processes that affect healthy cells as well as mathematical models for processes that affect cell populations with one or more diseases. In addition, a model of treatment effects 2.3 on each of these processes is created. The treatment effects include processes that are specific to individual treatment. Such a treatment may be based on the effects of a drug's process that affects the relevant cell population. Examples of these effects include interactions involving pharmacokinetic (PK), pharmacodynamics (PD), cytotoxic and cytostatics, or any other method of affecting cell biology and causing cell death, with associated biological processes.

The combination of these models provides a detailed mathematical model of the overall bio-clinical scenario in a general sense or for a specific patient, together with the specific effects of a particular treatment. Once the comprehensive model is constructed, the characteristic parameters are incorporated in it. The characteristic parameters could be either population averaged or patient specific. In case of the parameters could be either population averaged or patient specific. In case of the general case, average patient parameters are incorporated. The average patient parameters include parameters related to biological process dynamics, average drug PK, average drug PD and dynamics of does-limiting host tissues. In this way a "virtual general patient" in the form of a complete detailed model 2.4 is generated.

In case of the individual case, patient specific parameters 2.2 are incorporated. The patient specific parameters include parameters related to biological process dynamics, patient specific drug PK, patient specific drug PD and dynamics of does-limiting host tissues. The parameters related to biological process dynamics include, age, gender, weight, blood picture, desired length of the treatment protocol, previous reactions to treatment, molecular markers, genetic markers, pathologic specifics and cytologic specifics or clinical indications. In this way a "virtual individual patient" in the form of a complete detailed model 2.4 is generated.

Then a protocol space 2.5 is generated. To do this, possible permutations of certain parameters such as drug doses, dosing intervals, etc. are considered. Thus, a number of possible treatment protocols is generated. This number could be very large because of the number of permutations possible. The amount of possibilities depends on the number and ranges of parameters considered.

A fitness function 2.6 is then constructed by mathematically considering different possible factors which may be influenced by the treatment. These may include patient survival, time to death, time to reach a specified disease stage (including cure), tumor load, pathogen load, cytotoxicity to normal or diseased tissues, other side effects, quality of life, cost of treatment, pain, etc.

The user can alter certain specific parameters in the fitness function so as to adjust this function to the user's specific goals. The user can be anybody, including a medical doctor, a scientist or a drug developer. Based on the selected parameters, the fitness function is applied. This results in the calculation of a fitness score for each and every protocol in the protocol space. Finally, the optimization step is carried out 2.7, either by search heuristics or by analytical methods, in order to select the optimal treatment protocol 2.8 from all the scored possibilities. The analytical methods include the use of Operations Research techniques. In selecting the optimal treatment protocol cytotoxic effects as well as treatment efficacy are incorporated, as well as other objectives of the said fitness function. The heuristics, or rules of thumb employed include computational facility. The optimal treatment protocol is a combination of disease and treatment strategy, including type of treatment, device, drug or drug combination, radiotherapy, surgery and treatment schedule.

In this way, a disease specific, patient specific, situation specific, treatment type specific (e.g. drug therapy, operation, radiotherapy), drug specific, or an objective specific treatment protocol may be obtained. The actual time it takes once the parameters are entered may be negligibly short or up to hours, depending on the length of the simulated treatment period and the power of the specific search heuristics and the computational tools, making this a very feasible tool.

Systems and methods embodying the above disclosed technique for a general patient as well as for an individual patient are within the scope of the present invention.

The system can be implemented remotely over a distributed computing system with the user remotely dialing in. It can also be implemented over the internet. The computer could be a PC, mainframe, a workstation or a remote computer on a network.

Another aspect of the disclosed technique is a computer program code. The computer program product includes a computer readable medium. It should be noted that the computer readable medium includes any fixed media including, but not limited to, floppy disk, hard disk, CD, chips, tapes, cartridges with Ics, etc. The computer readable media also includes instructions transmitted through a network or downloaded from the Internet. The computer program product includes instructions for enabling a computer to aid in selecting a treatment protocol. The instructions include a system model code. A treatment protocol code is provided for a plurality of treatment protocols. In case of the disclosed technique for an individual patient, a system model modifier code is provided that enables the computer to modify the system model based on parameters specific to the individual. A selector code enables a computer to select an optimal treatment protocol from the plurality of treatment protocols based on the modified system model.

Construction of detailed mathematical models for biological processes and treatments are discussed herein in relation to various other embodiments of the disclosed technique. Techniques involving a model of platelets production and related diseases, including Thrombocytopenia, with treatment by TPO, a model of Neutrophil production and related diseases, including Neutropenia, and treatment by G-CSF, and a model of cancer growth and cancer treatment, including chemotherapy, are disclosed herein. An embodiment for specific optimization (by linear programming) is implemented for the system involving the Neutrophil model. An embodiment that uses a general heuristic optimization method is disclosed as well.

IV.A. Thrombopoiesis and Thrombopoietin (TPO)

An embodiment of the present invention involves the disclosed techniques for modeling the Thrombopietic lineage, diseased Thrombopoiesis such as Thrombocytopenia and treatment with Thrombopoietin. Thrombocytopenia is a common hazardous blood condition, which may appear in different clinical situations, including cancer chemotherapy. Recently, a Thrombopoiesis-controlling cytokine, Thrombopoietin (TPO), was isolated and its human recombinant analog became available. A mathematical model is disclosed herein that simulated dynamics of a Thrombopoietic lineage in the bone marrow, of platelet counts in the periphery, and effects of TPO administration on the lineage and platelet counts.

TPO is a cytokine, glycoprotein of about 350 amino acids, that resembles erythropoiesis-stimulating hormone, erythropoietin. Its synthetic analogs, recombinant human Thrombopoietin (rHuTPO) and recombinant human megakaryocyte growth and development factor (rHuMGDF), are available as well and are undergoing clinical trials.

For further details see Alexander W S: Thrombopoietin. *Growth Factors.* 1999; 17(1); pp. 13-24; Kaushansky K: Thrombopoietin: the primary regulator of platelet production. *Blood.* July 1995; Vol. 86(2); pp. 419-431; Vadhan_Raj-Raj S: Recombinant human Thrombopoietin: clinical experience and in vivo biology. *Seminars Hem.* July 1998; Vol. 35(3); pp. 261-268; Harker L A: Physiology and clinical applications of platelet growth factors. *Current Opinion Haematol.* 1999; Vol. 6; pp. 127-134; and Neelis K J, Hartong S C, Egeland T, Thomas G R, Eaton D L, Wagemaker G: The efficacy of single-dose administration of Thrombopoietin with coadministration of either Granulocyte/macrophage or Granulocyte colony-stimulating factor in myelosuppressed rhesus monkeys. *Blood.* October 1997; Vol. 90(7); pp. 2565-2573.

These compounds have been shown to have the same biological activity as TPO has, so the term TPO will be used without distinguishing between its different forms and analogs.

TPO is a primary growth factor of the Thrombopoietic cell line both in vivo and in vitro. Aside from this, TPO may be potent in stimulation and co-stimulation of other haemopoietic lineages (e.g., Granulopoietic or erythropoietic).

IV.A.1. Model of the Biological System a) Background of Thrombopoiesis

Like all other haemopoietic lines, the Thrombopoietic line originates from poorly differentiated, multipotential cells, that are capable of some division and self-reconstitution. For more background details, see Swinburne J L, Mackey M C: Cyclical Thrombocytopenia: characterization by spectral analysis and a review. *J Theor Medicine.* 2000; Vol. 2; pp. 81-91; and Beutler E, Lichtman M A, Coller B S, Kipps T J: Williams HAEMATOLOGY. 5$^{th}$ edition McGraw-Hill, Inc. 1995; Chapter 118; pp. 1149-1161. Such bone marrow cell compartments as pluripotential haemopoietic stem cells and common myeloid progenitor cells (CFU-GEMM) have more or less these characteristics. For more background details, see Beutler E, Lichtman M A, Coller B S, Kipps T J: Williams HAEMATOLOGY. 5$^{th}$ edition McGraw-Hill, Inc. 1995; Chapter 118; pp. 1149-1161.

Gradually, the cells become more and more differentiated and thus committed to the Thrombopoietic line. At this stage they proliferate extensively. Colony-forming Units-megakaryocytes (CFU-Meg) is an example of such compartment. Sometimes burst-forming units-megakaryocyte (BFU-Meg), promegakaryoblasts or megakaryoblasts are considered as having the similar properties. For more background details, see Swinburne J L, Mackey M C: Cyclical Thrombocytopenia: characterization by spectral analysis and a review. *J Theor Medicine.* 2000; Vol. 2; pp. 81-91; and Beutler E, Lichtman M A, Coller B S, Kipps T J: Williams HAEMATOLOGY. 5$^{th}$ edition McGraw-Hill, Inc. 1995; Chapter 118; pp. 1149-1161.

The committed megakaryocytopoietic cells, megakaryocyte precursors, go through several stages of maturation. However, megakaryocyte maturation is somewhat different from that of other haemopoietic lines. Here, along with cytoplasmic maturation, cell nuclei undergo mitotic events. However, although the DNA material of these cells doubles, cell division does not happen. Such incomplete mitosis is termed endomitosis or endoreduplication. Consequently, the cell becomes poliploid with 2N, 4N, 8N, etc., amount of DNA. Some authors call the cells with 2N to 4N chromosome number promegakaryoblasts, others call them megakaryoblasts or immature megakaryocytes. For more background details, see Swinburne J L, Mackey M C: Cyclical Thrombocytopenia: characterization by spectral analysis and a review. *J Theor Medicine.* 2000; Vol. 2; pp. 81-91; and Beutler E, Lichtman M A, Coller B S, Kipps T J: Williams HAEMATOLOGY. 5$^{th}$ edition McGraw-Hill, Inc. 1995; Chapter 118; pp. 1149-1161.

Usually, megakaryocytes do not start to release platelets until they reach 8N to 16N state. For more background details, see Gordon A S: Regulation of haematopoiesis. N.Y. 1970 Vol. 2, Section IX (textbook); and Beutler E, Lichtman M A, Coller B S, Kipps T J: Williams HAEMATOLOGY. 5$^{th}$ edition McGraw-Hill, Inc. 1995; Chapter 118; pp. 1149-1161.

Then they begin to create demarcation membranes that envelop cytoplasm fragments generating platelets. The platelets are released into the blood stream. A small fraction of the megakaryocytes do not cease their endoreduplication at the 16N-stage, but rather continue with one or more additional endomitoses and get thus a ploidy of 32N or more. For background details, see Swinburne J L, Mackey M C: Cyclical Thrombocytopenia: characterization by spectral analysis and a review. *J Theor Medicine.* 2000; Vol. 2; pp. 81-91.

The amounts of cytoplasm, cell volume and the ability to release platelets increase proportionally to the cell ploidy. For background details, see Harker L A, Finch C A: Thrombokinetics in man. *J Clin Invest.* 1969; Vol. 48; pp. 963-974; and Harker L A: Thrombokinetics in idiopathic Thrombocytopenic purpura. *Br J Haematol.* 1970; Vol. 19; pp. 95-104.

b) B. Mathematical Model

Figure 3:
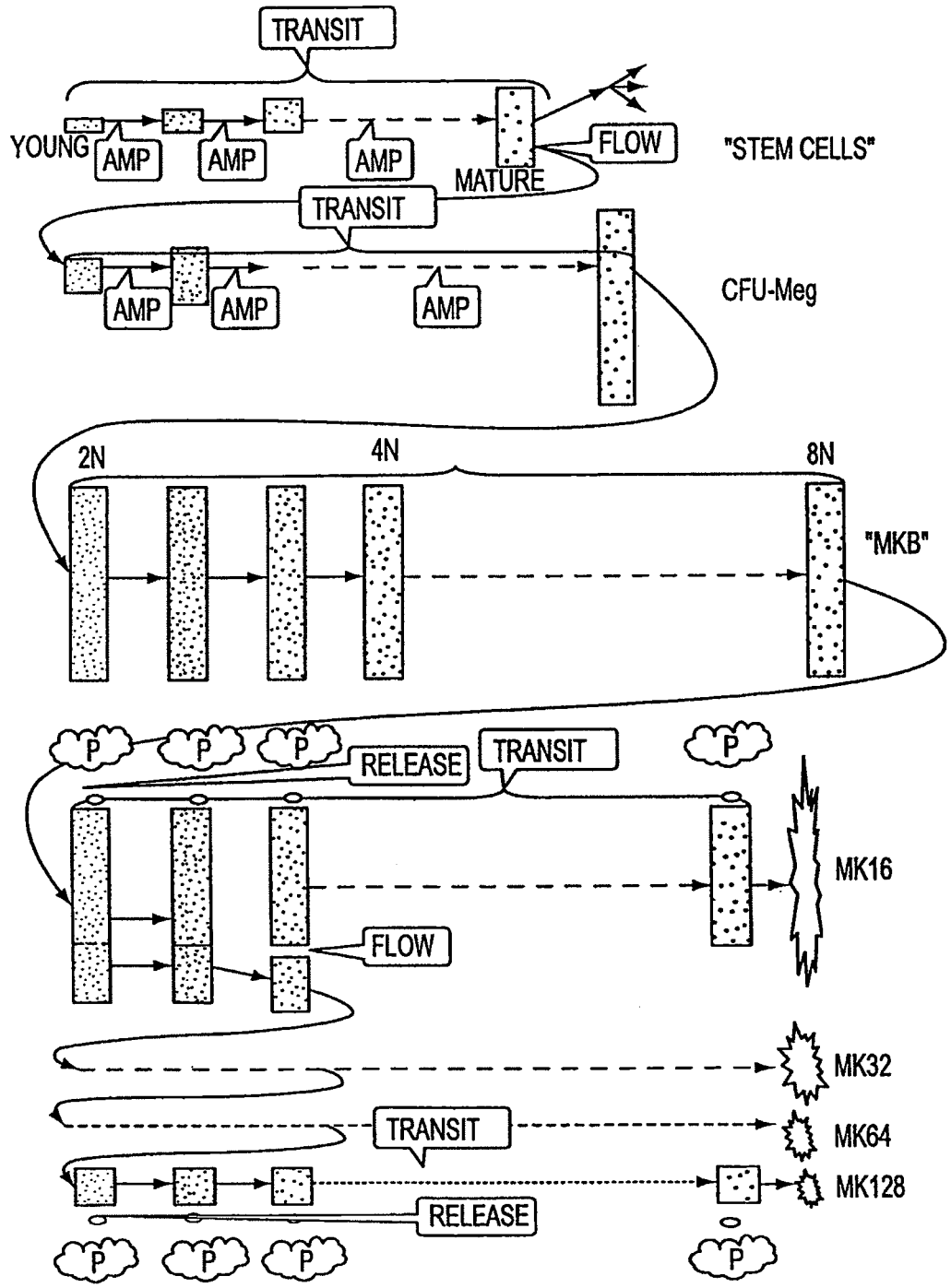
FIG. 3 is a schematic illustration of a biological model, in accordance with one embodiment of the present invention.

Reference is now made to FIG. 3, which is a detailed illustration of a model predicting Thrombopoiesis. As shown in FIG. 3, the Thrombopoietic lineage is divided into eight compartments. The first compartment, called Stem Cells (SC) and labeled 30, refers to all bone marrow haemopoietic progenitors that have an ability to differentiate into more than one line (e.g., pluripotential stem cells, CFU-GEMM, and others). Cells of SC compartment 30 proliferate, giving rise to "new" stem cells, or mature, and subsequently differentiate into megakaryocytes or other precursors. Although the consideration of the former process, i.e. the renewal of the stem cells by "new" ones, is not completely understood biologically, our simple description may serve as an acceptable assumption since the characteristics of this population are not elaborated in details. For background details, see Schofield R, Lord B I et al: Self-maintenance capacity of CFU-S. *J Cellular Phisiol.* 1980; Vol. 103: 355-362; and Rosendaal M, Hodgson G S, Bradley T R: Organization of haemopoietic stem cells: the generation-age hypothesis. *Cell Tissue Kinetics.* 1979; Vol. 12: 17-29.

Cell death through apoptosis may have a significant effect on cell number within proliferating compartments. For background details, see Swinburne J L, Mackey M C: Cyclical Thrombocytopenia: characterization by spectral analysis and a review. *J Theor Medicine.* 2000; Vol. 2; pp. 81-91.

However, the effect of apoptosis is combined, with the effect of cell proliferation into a total amplification of cell number in a given compartment (for example $\alpha_{SC}$). An assumption is made that no apoptosis occurs in non-proliferating megakaryocytic compartments, due to lack of evidence to the contrary. However, an assumption of apoptotic non-proliferating megakaryocytes can be incorporated in the mathematical model.

Biologically, rates of proliferation and maturation, the ability to reconstitute, and other characteristics differ between particular cell types within a primitive progenitor population. However, in this model there is no distinction between them; all progenitor cells are considered to be one population with common properties.

It has been shown conventionally that probabilities of stem cell differentiation into one or another haemopoietic lineage are constant in time. Thus, it is assumed here that a flow of stem cells into the megakaryocyte lineage is fixed (for example $\Phi_{SC}$). For background details, see Mayani H, Dragowska W, Lansdorp P M: Lineage commitment in human hemopoiesis involves asymmetric cell division of multipotent progenitors and does not appear to be influenced by cytokines. *J Cellular Physiol.* 1993; Vol. 157; pp. 579-580; Golde D W: The Stem Cell. *Medicine.* December 1991; Morrison 53, Uchida N, Weissman I L: The biology of haematopoietic stem cells. *Annu Rev Cell Dev Biol.* 1995; Vol. 11; pp. 35-71; and von Schulthess G K, Gessner U: Oscillating platelet counts in healthy individuals: experimental investigation and quantitative evaluation of Thrombopoietic feedback control. *Scand J Haematol.* 1986; Vol. 36; pp. 473-479.

The same was assumed about the stem cell self-renewal. Thus, after the cells spend a defined transit time, for example $\tau_{SC}$, in SC compartment 30, a certain constant fraction of the cells return to their "young state", i.e. start their passage through SC compartment 30 again, as shown in line 31.

Another constant fraction ($\Phi_{SC}$, for example) of cells pass into the next compartment named Colony-Forming Units (CFU-Meg), labeled 40. It is presumed that remaining stem cells differentiate into haematopoietic lineages other than megakaryocytic.

CFU-Meg refers to all cells that are already committed to the megakaryocyte line but are still capable of proliferation. Cells of CFU-Meg compartment 40, like those of SC compartment 30, spend some time multiplying at an amplification rate of about $\alpha_{SFU}$, for example, and maturing before losing their proliferative abilities and passing on to the next compartment 50, called megakaryoblasts (MKB). For background details see, Eller J, Gyori I et al: Modelling Thrombopoiesis regulation—I: model description and simulation results. *Comput Math Applic.* 1987; Vol. 14 (9-12); pp. 841-848.

The time they spent in CFU-Meg compartment is $\tau_{CFU}$.

MKB compartment 50 includes all the cells that have lost the ability to proliferate, but are not yet sufficiently mature to release platelets. For the purposes of the model, the assumption is made that megakaryocytes do not start to release platelets until they reach the 16N-ploidy phase. For background details, see Gordon A S: Regulation of haematopoiesis. N.Y. 1970 Vol. 2, Section IX (textbook).

Hence, MKB refers to 2N, 4N and 8N cells of megakaryocyte lineage that cannot divide, at all stages of cytoplasmic maturity. After these cells spend the designated transit time $\tau_{MKB}$, for example, in MKB compartment 50, they move to the next compartment 60, which is a MK16 bone marrow compartment.

The cells of MK16 compartment 60 are megakaryocytes of 16N-ploidy class that release platelets at a constant uniform rate ($\gamma_{MK16}$) until they exhaust their capacity ($C_{MK16}$, for example), and then are disintegrated. For background details, see, Harker L A, Finch C A: Thrombokinetics in man. *J Clin Invest.* 1969; Vol. 48; pp. 963-974; and Eller J, Gyori I et al: Modelling Thrombopoiesis regulation—I: model description and simulation results. *Comput Math Applic.* 1987; Vol. 14 (9-12); pp. 841-848.

Cell volume has a linear relationship with megakaryocyte ploidy. Hence, it is assumed that all 16N-megakaryocytes have the same volume and, thus, the same platelet-releasing capacity. For background details, see, Harker L A, Finch C A: Thrombokinetics in man. *J Clin Invest.* 1969; Vol. 48; pp. 963-974.

Therefore all platelet-releasing 16N-megakaryocytes are in transit for the same amount of time ($\tau_{MK16}$, for example) until they are exhausted and disintegrated.

However, some 16N-megakaryocytes do not participate in platelet release, but rather continue with another endomitosis over a 48-hour time period, and become 32N-megakaryocytes. These constitute a new and distinct MK32 compartment 70. Thus, after time $\mu$ in MK16 compartment 60, a certain fraction of the cells leave MK16 compartment 60 and go on to MK32 compartment 70.

32N-megakaryocytes release platelets as well. The rate of platelet release is constant for every compartment and proportional to the ploidy state of megakaryocytes in it. For background details, see, Harker L A, Finch C A: Thrombokinetics in man. *J Clin Invest.* 1969; Vol. 48; pp. 963-974; and Harker L A: Thrombokinetics in idiopathic Thrombocytopenic purpura. *Br J Haematol.* 1970; Vol. 19; pp. 95-104.

Thus, every 16N-megakaryocyte releases, for example, $\gamma_{MK16}$ platelets per hour and every 32N-megakaryocyte, for example, releases $\gamma_{MK32}$ platelets per hour (twice as much). However, 32N-megakaryocytes are not exhausted more quickly than 16N-megakaryocytes, since they have 2 times greater volume and platelet-releasing capacity. Consequently, all platelet-releasing megakaryocyte compartments have the same transit time.

Once again, some fraction of cells, for example $\Phi_{MK32}$, are not engaged in platelet formation, and continue to the 64N-stage. Additional endomitosis in MK32 compartment 70 takes the same amount of time μ as in MK16 compartment 60. The 64N-megakaryocytes continue the process in a new MK64 compartment 80, and $\Phi_{MK64}$ of them become 128N-cells in yet another MK128 compartment 90. Additional endomitosis in MK64 compartment 80 takes the same amount of time μ as before. Megakaryocytes of greater ploidy classes have not been known to be encountered in humans.

Finally, there is a platelet (PL) compartment 100. This is not a bone marrow compartment, but rather the platelet pool in the peripheral blood Platelets released from megakaryocytes of 16N-, 32N-, 64N-, and 128N-ploidy classes enter platelet compartment 100. There are two mechanisms of platelet elimination from circulation: By age-dependent destruction and by the normal utilization in order to maintain the integrity of blood vessels. For background details, see, Harker L A, Roskos L K, Marzec U M, Carter R A, Cherry J K, Sundell B, Cheung E N, Terry D, Sheridan W: Effects of megakaryocyte growth and development factor on platelet production, platelet life span, and platelet function in healthy human volunteers. *Blood*. 2000 April; Vol. 95(8); pp. 2514-2522; and von Schulthess G K, Gessner U: Oscillating platelet counts in healthy individuals: experimental investigation and quantitative evaluation of Thrombopoietic feedback control. *Scand J Haematol*. 1986; Vol. 36; pp. 473-479.

The first mechanism is reflected as platelet disappearance after they spend their designated transit time, for example, in the PL compartment. The second one is rather age-independent and it is reflected as constant platelet efflux (d) throughout all platelet age-stages.

IV.A.2. Model of Treatment Effects a) A. Background of TPO

The major sites of TPO production are the liver and kidney. TPO is also produced in the spleen and bone marrow, but the production rate in these organs is 5 times lower than in the liver and kidney For background details, see, Alexander W S: Thrombopoietin. *Growth Factors*. 1999; 17(1); pp. 13-24; Sungaran R, Markovic B, Chong B H: Localization and regulation of Thrombopoietin mRNA expression in human kidney, liver, bone marrow, and spleen using in situ hybridization. *Blood*. January 1997; Vol. 89(1); pp. 101-107; Nagata Y, Shozaki Y, Nagahisa H, Nagasawa T, Abe T, Todokoro K: Serum Thrombopoietin level is not regulated by transcription but by the total counts of both megakaryocytes and platelets during Thrombocytopenia and Thrombocytosis. *Thromb Haemost*. 1997; Vol. 77; pp. 808-814; Nagahisa H, Nagata Y, Ohnuki T, Osada M, Nagasawa T, Abe T, Todokoro K: Bone marrow stromal cells produce Thrombopoietin and stimulate megakaryocyte growth and maturation but suppress proplatelet formation. *Blood*. February 1996; Vol. 87(4); pp. 1309-1316; and Rasko J E J, Begley C G: Molecules in focus: The Thrombopoietic factor, Mpl-ligand. *Int J Bioch Cell Biol*. 1998; Vol. 30: 657-660.

Some low TPO production has also been found in many other sites in the body. For background details, see Nagata Y, Shozaki Y, Nagahisa H, Nagasawa T, Abe T, Todokoro K: Serum Thrombopoietin level is not regulated by transcription but by the total counts of both megakaryocytes and platelets during Thrombocytopenia and Thrombocytosis. *Thromb Haemost*. 1997; Vol. 77; pp. 808-814; and Wichmann H E, Gerhardts M D, Spechtmeyer H, Gross R: A mathematical model of Thrombopoiesis in rats. *Cell Tissue Kinet*. 1979; Vol. 12; pp. 551-567.

Rates of liver and kidney TPO production are constant under Thrombocytopenia and Thrombocytosis of varying degrees of severity. For background details, see, Alexander W S: Thrombopoietin. *Growth Factors*. 1999; 17(1); pp. 13-24; Sungaran R, Markovic B, Chong B H: Localization and regulation of Thrombopoietin mRNA expression in human kidney, liver, bone marrow, and spleen using in situ hybridization. *Blood*. January 1997; Vol. 89(1); pp. 101-107; and Nagahisa H, Nagata Y, Ohnuki T, Osada M, Nagasawa T, Abe T, Todokoro K: Bone marrow stromal cells produce Thrombopoietin and stimulate megakaryocyte growth and maturation but suppress proplatelet formation. *Blood*. February 1996; Vol. 87(4); pp. 1309-1316.

TPO production in the spleen and bone marrow is inversely related to the megakaryocyte mass, but the actual contribution is negligible with regard to total TPO production. For background details, see, Alexander W S: Thrombopoietin. *Growth Factors*. 1999; 17(1); pp. 13-24; and Sungaran R, Markovic B, Chong B H: Localization and regulation of Thrombopoietin mRNA expression in human kidney, liver, bone marrow, and spleen using in situ hybridization. *Blood*. January 1997; Vol. 89(1); pp. 101-107.

Another mechanism of TPO concentration regulation is receptor-mediated TPO uptake, since TPO-receptors on the platelet and megakaryocyte surfaces are the main TPO-clearance mechanism. Thus, TPO concentration is inversely related to the total platelet and megakaryocyte mass. For background details, see, Alexander W S: Thrombopoietin. *Growth Factors*. 1999; 17(1); pp. 13-24; Harker L A: Physiology and clinical applications of platelet growth factors. *Current Opinion Haematol*. 1999; Vol. 6; pp. 127-134; Hsu H C, Tsai W H, Jiang M L, Ho C H, Hsu M L, Ho C K, Wang S Y: Circulating levels of Thrombopoietic and inflammatory cytokines in patients with clonal and reactive Thrombocytosis. *J Lab Clin Med*. 1999; Vol. 134(4); pp. 392-397; Stoffel R, Wiestner A, Skoda R C: Thrombopoietin in Thrombocytopenic mice: evidence against regulation at the mRNA level and for a direct regulation role of platelets. *Blood*. January 1996; Vol. 87(2); pp. 567-573; Alexander W S: Thrombopoietin and the c-Mpl receptor: insights from gene targeting. *Int J Biochem Cell Biol*. 1999 October; Vol. 31(10); pp. 1027-1035. [ABSTRACT]; Miyazaki M, Fujiwara Y, Isobe T, Yamakido M, Kato T, Miyazaki H: The relationship between carboplatin AUC and serum Thrombopoietin kinetics in patients with lung cancer. *Anticancer Research*. 1999; Vol. 19; pp. 667-670; and Rasko J E J, Begley C G: Molecules in focus: The Thrombopoietic factor, Mpl-ligand. *Int J Bioch Cell Biol*. 1998; Vol. 30: 657-660.

The effects of TPO on the Thrombopoietic line may be divided into three types: (i) stimulation of proliferation of megakaryocyte progenitors that have an ability to proliferate; (ii) stimulation of maturation of all megakaryocyte progenitors; (iii) induction of additional endomitosis of already mature megakaryocytes, which leads to an increase in the modal megakaryocyte ploidy. For background details, see, Kaushansky K: Thrombopoietin: the primary regulator of platelet production. *Blood*. July 1995; Vol. 86(2), pp. 419-431; Somlo G, Sniecinski I, ter Veer A, Longmate J, Knutson G, Vuk-Pavlovic S, Bhatia R, Chow W, Leong L, Morgan R, Margolin K, Raschko J, Shibata S, Tetef M, Yen Y, Forman S, Jones D, Ashby M, Fyfe G, Hellmann S, Doroshow J H: Recombinant Human Thrombopoietin in combination with Granulocyte colony-stimulating factor enhances mobilization of peripheral blood progenitor cells, increases peripheral blood platelet concentration, and accelerates haematopoietic recovery following high-dose chemotherapy. *Blood.* May 1999; Vol. 93(9); pp. 2798-2806; Murray L J, Luens K M, Estrada M F, Bruno E, Hoffman R, Cohen R L, Ashby M A, Vadhan-Raj S: Thrombopoietin mobilizes CD34+ cell subsets into peripheral blood and expand multilineage progenitors in bone marrow of cancer patients with normal haematopoiesis. *Exp Hem.* 1998; Vol. 26; pp. 207-216; Vadhan-Raj S, Murray U, Bueso-Ramos C, Patel S, Reddy S P, Hoots W K, Johnston T, Papadopolous N E, Hittelman W N, Johnston D A, Yang T A, Paton V E, Cohen R L, Hellmann S D, Benjamin R S, Broxmeyer H E: Stimulation of megakaryocyte and platelet production by a single dose of recombinant human Thrombopoietin in patients with cancer. *Ann Intern Med.* May 1997; Vol. 126(9); pp. 673-681; Wichmann H E, Gerhardts M D, Spechtmeyer H, Gross R: A mathematical model of Thrombopoiesis in rats. *Cell Tissue Kinet.* 1979; Vol. 12; pp. 551-567; Harker L A, Roskos L K, Marzec U M, Carter R A, Cherry J K, Sundell B, Cheung E N, Terry D, Sheridan W: Effects of megakaryocyte growth and development factor on platelet production, platelet life span, and platelet function in healthy human volunteers. *Blood.* 2000 April; Vol. 95(8); pp. 2514-2522; Swinburne J L, Mackey M C: Cyclical Thrombocytopenia: characterization by spectral analysis and a review. *J Theor Medicine.* 2000; Vol. 2; pp. 81-91; Rasko J E J, Begley C G: Molecules in focus: The Thrombopoietic factor, Mpl-ligand. *Int J Bioch Cell Biol.* 1998; Vol. 30: 657-660; and De Sauvage F J, Carver-Moore K, Luoh S-M, Ryan A, Dowd M, Eaton D L, Moore M W: Physiological regulation of early and late stages of megakaryocytopoiesis by Thrombopoietin. *J Esp Med.* 1996 February; Vol. 183: 651-656.

b) Mathematical Model of TPO Effects

TPO concentration effects on the Thrombopoiesis line is now considered. As discussed above, three things depend on TPO concentration: (i) amplification rate (amp), (ii) the rate of cell maturation or, alternatively, transit time through a given compartment (transit), and (iii) the fraction of megakaryocytes of given ploidy that undergo additional endomitosis and pass on to the next ploidy class.

(1) TPO Concentration

Recombinant human full-length TPO and its truncated form rHuMGDF are fully active biologically. Therefore, in our model we add exogenously administered recombinant protein to endogenously produced TPO in order to calculate actual TPO concentration (c).

As mentioned above, the rate of TPO production in the main TPO production sites, i.e. liver and kidney, is constant under Thrombocytopenia or Thrombocytosis. For background details, see, Alexander W S: Thrombopoietin. *Growth Factors.* 1999; 17(1); pp. 13-24; Sungaran R, Markovic B, Chong B H: Localization and regulation of Thrombopoietin mRNA expression in human kidney, liver, bone marrow, and spleen using in situ hybridization. *Blood.* January 1997; Vol. 89(1); pp. 101-107; and Nagata Y, Shozaki Y, Nagahisa H, Nagasawa T, Abe T, Todokoro K: Serum Thrombopoietin level is not regulated by transcription but by the total counts of both megakaryocytes and platelets during Thrombocytopenia and Thrombocytosis. *Thromb Haemost.* 1997; Vol. 77; pp. 808-814.

The level of TPO mRNA in sites like the bone marrow and spleen, where it is produced in a 5-fold lower rate than in the liver and kidney, is not significantly different from the TPO level in peripheral blood. For background details, see Hsu H C, Tsai W H, Jiang M L, Ho C H, Hsu M L, Ho C K, Wang S Y: Circulating levels of Thrombopoietic and inflammatory cytokines in patients with clonal and reactive Thrombocytosis. *J Lab Clin Med.* 1999; Vol. 134(4); pp. 392-397.

Therefore, the assumption is made that the bone marrow and spleen contributions to the total TPO concentration are insignificant. Endogenously produced TPO is assumed to have a constant rate of production p. However, this number can change.

The main mechanism that controls TPO concentration in the blood is receptor-mediated TPO uptake (u). For background details, see, Alexander W S: Thrombopoietin. *Growth Factors.* 1999; 17(1); pp. 13-24; Harker L A: Physiology and clinical applications of platelet growth factors. *Current Opinion Haematol.* 1999; Vol. 6; pp. 127-134; Hsu H C, Tsai W H, Jiang M L, Ho C H, Hsu M L, Ho C K, Wang S Y: Circulating levels of Thrombopoietic and inflammatory cytokines in patients with clonal and reactive Thrombocytosis. *J Lab Clin Med.* 1999; Vol. 134(4); pp. 392-397; Stoffel R, Wiestner A, Skoda R C: Thrombopoietin in Thrombocytopenic mice: evidence against regulation at the mRNA level and for a direct regulation role of platelets. *Blood.* January 1996; Vol. 87(2); pp. 567-573; Alexander W S: Thrombopoietin and the c-Mpl receptor: insights from gene targeting. *Int J Biochem Cell Biol.* 1999 October; Vol. 31(10); pp. 1027-1035. [ABSTRACT].

Another mechanism of TPO removal from the blood is non-specific TPO-receptor-independent clearance (l). This mechanism is rather insignificant in the normal state, when receptor-mediated TPO binding, endocytosis, and degradation remove most of the TPO. Thus, the formula that calculates TPO concentration hourly is given in Equation 1 as follows:

$$C^*_{i+1} = C_i + p + x_i - u_i - l_i \, p, x_i, u_i, l_i \geq 0 \; C_i > 0 \quad (1)$$

where Ci is TPO concentration at the current hour (i); $C^*_{i+1}$ is approximation of the TPO concentration at the next hour (detailed below); p is TPO concentration produced per hour endogenously; xi is the addition to TPO concentration due to exogenous TPO administration; ui is TPO concentration removed from the blood by receptor-mediated binding; li is TPO concentration cleared from circulation by non-specific mechanisms.

It is assume that receptor-mediated TPO clearance depends on the total number of TPO receptors (n) and on the ability of each receptor to uptake TPO (a):

$$u_i = n_i \cdot a \; n_i, a \geq 0 \quad (2)$$

where $n_i$ represents the receptor pool and a is TPO-clearing ability of the receptors, i.e. amount of TPO that each receptor removes per hour.

Both, megakaryocyte and platelet mass contribute to the total receptor number (n) and, thus, to the rate of TPO clearance (u). 15 We assume that every platelet bears the same number of TPO receptors (mPL). The receptor number on megakaryocytes, however, changes. Thus, the receptor pool (n) is:

$$n_i = \sum_{comp=1}^{4} \left( \sum_{j=1}^{[\tau_{comp}]} (q_{comp,j,i} \cdot m_{comp,j}) \right) + q_{PL,i} \cdot m_{PL} \quad (3)$$

$$q_{comp,j,i}, q_{PL,i}, m_{comp,j}, m_{PL} \geq 0$$

where comp (1 to 4) is one of the platelet releasing megakaryocyte compartments (MK16, MK32, MK64, MK128, respectively); j is the period (in hours) that a given megakaryocyte already spent in the specific compartment; [τ] denotes τ rounded to an integer; $q_{comp,j,i}$ is the quantity of the megakaryocytes of the specific compartment (comp), which spent a given period (j) in it; $m_{comp,j}$, is the receptor number on given megakaryocyte; $q_{PL}$ i is the platelet number; $m_{PL}$ is the receptor number per platelet.

It is assumed that the number of TPO receptors on each megakaryocyte ($m_{comp,j}$) equals the number of platelets that the megakaryocyte is capable of releasing ($c_{comp}$) times the average number of receptors per every potential platelet (b).

$$m_{comp,j} = (c_{comp} - r_{comp} \cdot j) \cdot b \quad c_{comp}, r_{comp}, j, b \geq 0 \quad (4)$$

where ccomp is the number of platelets that the megakaryocyte of the specific compartment comp can release during its entire life-span ($\tau_{comp}$); rcomp is the rate of platelet release by the megakaryocyte; j is the period that this megakaryocyte already spent in this compartment; b is the number of receptor on the megakaryocyte per potential platelet.

It is also assumed that the non-specific TPO clearance ($l_i$) is exponential, i.e. every hour some fraction (f) of a current amount of TPO ($c_i$) is removed from circulation:

$$l_i = f \cdot C_i, f \geq 0 \quad (5)$$

where f is the coefficient of non-specific TPO clearance and $c_i$ is the current TPO concentration. Other modes of non-specific TPO removal can be assumed as well. Exogenous TPO is included in the model as a linear relation of the initial maximum TPO blood concentration ($x_i$) to the administered intravenous (IV) dose(s) (the relation coefficient is 0.0167) 21:

$$x_i = 0.0167 \cdot s_i, s_i \geq 0 \quad (6)$$

The state when TPO completely disappears from the blood seems very unlikely based on biological logic, so we restricted the lower limit of possible TPO concentration to certain minimum $\epsilon$ (positive). Thus, the equation (1) is modified to receive the full TPO concentration equation:

$$C_{i+1} = \max((C_i + p + x_i - a \cdot n_i - f \cdot C_i), \epsilon) \, \epsilon > 0 \quad (7)$$

In steady state, the TPO concentration (C) is constant.

(2) TPO Effects on Amplification Rate

In the disclosed model, there are only two compartments, SC compartment 30 and CFU-Meg compartment 40, whose cells are capable of dividing. These compartments differ significantly from each other, thus, we shall discuss them separately. Cells of other model compartments do not proliferate, and so their amplification rate equals 1 under all circumstances.

SC compartment 30:

Since TPO is primarily a Thrombopoiesis-stimulating cytokine, we assume that the cells, which are not committed to Thrombopoietic line yet (the SC compartment in our model), are relatively insensitive to TPO, compared to committed megakaryocytic cells. In the disclosed model this is considered as a threshold ($\theta$) in TPO concentration. Only above this threshold ($\theta$) TPO affects stem cells. As long as TPO remains below the threshold ($\theta$), stem cells in the model are regulated by intrinsic TPO-independent mechanism that keeps the size of their population almost constant.

Thus, below the threshold ($\theta$), SC amplification rate ($\alpha_{SC}$) is determined hourly depending on the current number of cells in the SC compartment. It is biologically reasonable that the dependence equation is a sigmoidal function where $\alpha_{SC}$ changes from 1 (i.e., no amplification, the cell number remains the same) when the cell number approaches infinity, up to the maximal value $\alpha_{SCw}$ when the cell number approaches zero. The increase in amplification rate ($\alpha_{SC}$) is relatively gradual as long as the cell number ($q_{SC,i}$) exceeds certain critical value (we assumed it to be a fraction (v) of the normal cell number ($q_{SCnorm}$)). However, when the cell number falls bellow this threshold, $\alpha_{SC}$ begins to increase rapidly in order to restore the SC compartment as soon as possible. It is assumed that at normal cell numbers ($q_{SCnorm}$), $\alpha_{SCi}$ should be a fraction ($\gamma$) of its maximal value $\alpha_{SCw}$. Following is an example of such equation:

$$\alpha^*_{SC,i+1}(q_{SC,i}, C_i) = \atop{C_i \leq \theta} \quad (8)$$

$$\begin{cases} (\alpha_{SCw} - 1) \cdot \dfrac{1}{\left(\dfrac{1}{y} - 1\right) \cdot \left(\dfrac{q_{SC,i}}{q_{SC\,norm}}\right)^{S_1} + 1} + 1, & q_{SC,i} \geq v \cdot q_{SC\,norm} \\ \alpha_{SCw} - (\alpha_{SCw} - \tilde{\alpha_{SC}}) \cdot \left(\dfrac{q_{SC,i}}{v \cdot q_{SC\,norm}}\right)^{S_2}, & q_{SC,i} < v \cdot q_{SC\,norm} \end{cases}$$

$$\tilde{\alpha_{SC}} = (\alpha_{SCw} - 1) \cdot \dfrac{1}{\left(\dfrac{1}{y} - 1\right) \cdot v^{S_1} + 1} + 1 \quad \begin{vmatrix} q_{SC}, S_{1,2}, \theta \geq 0 \\ \alpha_{SCw} \geq 1 \\ 0 < y, v \leq 1 \end{vmatrix}$$

where $\alpha^*_{SC,i+1}$ is the amplification rate calculated based solely on the cell number; $\alpha_{SCw}$ is the maximal possible rate of cell amplification in the SC compartment when TPO concentration (Ci) is below the threshold; $q_{SC,i}$ is a quantity of cells in the SC compartment; $q_{SC}$ norm is the normal quantity of cells there. S1 and S2 are the sensitivity coefficients in the regions of $q_{SC,i}$ higher or lower than the critical value ($vq_{SCnorm}$), respectively. These values determine the sensitivity of the mechanism that links the amplification rate ($\alpha_{SC}$) with the cell number ($q_{SC,i}$). In other words, they determine the steepness of the dependence curve in the corresponding regions. High S1 or S2 mean that $\alpha_{SC}$ changes significantly due to slight changes of $q_{SC}$, and low S1 or S2 mean that $\alpha_{SC}$ remains relatively constant whatever the changes of $q_{SC}$ are. Distinguishing between S1 and S2 allows us to force the amplification rate ($\alpha_{SC}$) to grow rapidly as the cell number ($q_{SC,i}$) falls below the critical value, thereby increasing the resistance of the system to further cell number ($q_{SC,i}$) decay. Although the symbols S1 and S2 appear in several equations, their values are specific for every equation.

It is suggested that TPO concentration (C) increase above the threshold should occur in severe platelet and/or megakaryocyte deficiency, or when TPO is administered exogenously. It is assumed that at these circumstances, TPO further increases the rate of cell amplification in the "Stem Cell" compartment ($\alpha_{SC}$). It is also assumed that the increase is proportional to the difference between actual TPO concentration (Ci) and the threshold. Thus, TPO effects appear gradually from the zero increase, when TPO concentration (Ci) equals the threshold. Saturation of the mechanisms of TPO effect is reflected in the concavity of the effect function.

The following is an example of such a function:

$$\alpha_{SC,i+1}(q_{SC,i}, C_i) = \alpha^*_{SC,i+1}(q_{SC,i}, C_i) + t \cdot \ln(C_i - \theta + 1) \quad (9)$$
$$\atop{C_i > \theta}$$

$$t, \theta \geq 0$$

where $\alpha^*_{SC,i+1}$ is the same expression as in equation (8), i.e. amplification calculated based on a TPO-independent mechanism, and the second operand is the TPO-related contribution to the amplification rate ($\alpha_{SC,i+1}$). t determines the steepness of the dependence curve (t is non-negative).

Although the symbol t appears in several equations, its value is specific for every equation. One is added to the ln argument in order to ensure positivity of the ln result.

CFU-Meg Compartment 40:

In contrast to the cells of the SC compartment, we assume that cells of this compartment are fully sensitive to TPO and respond to the absolute TPO concentration (Ci), not to its difference with a threshold (Ci−θ). In the disclosed model, there is no TPO-independent proliferative mechanism, and CFU-Meg cease to proliferate when deprived of TPO. On the other hand, when TPO concentration (Ci) in the system increases, $\alpha_{CFU}$ does not rise to infinity, but rather gradually reaches saturation, which also seems reasonable biologically. At normal TPO concentrations ($C_{norm}$), we assume $\alpha_{CFU}$ to be a fraction (h) of its maximal value ($\alpha_{CFUmax}$). Thus an equation that describes the relation of the amplification rate of CFU-Meg cells ($\alpha_{CFU}$) to TPO concentration (Ci) represents a sigmoidal function with $\alpha_{CFU}$ equaling 1 when TPO concentration (Ci) is zero, passing through h times $\alpha_{CFUmax}$ when TPO concentration is normal (Ci), and approaching an asymptote in $\alpha_{CFUmax}$ when TPO concentration (Ci) approaches infinity. In addition, in order to enable the system to be sensitive both to the regulation by endogenously produced TPO and to the effect of the exogenously administered drug, it was assumed that the function changes relatively rapidly in the region of normal TPO concentration ($C_{norm}$) and with a much smaller rate when a TPO concentration (Ci) is somewhat higher than normal ($C_{norm}$). The following is an example of such a function:

$$\alpha_{CFU,i+1}(C_i) = \qquad (10)$$

$$(\alpha_{CFU\,max}-1)\cdot\left(1-\frac{1}{\frac{1}{\frac{1}{h}-1}\cdot\left(\frac{C_i}{C_{norm}}\right)^t+1}\right)+1 \quad \begin{vmatrix} C_{norm} > 0 \\ t \geq 0 \\ 0 < h \leq 1 \end{vmatrix}$$

where $\alpha_{CFU,i+1}$ is an amplification rate of the CFU compartment; $\alpha_{CFUmax}$ is a maximal value of amplification rate there; $C_{norm}$ is normal TPO concentration; t is the parameter that determines the steepness of the dependence curve.

(3) TPO Effects on Transit Time

For the reason noted earlier, it is assumed that all platelet-releasing megakaryocyte compartments have the same transit time ($\tau_{MK}$). It is also assumed that neither the relation of megakaryocyte volume (and thus, its platelet releasing capacity $c_{comp}$) nor of its rate of platelet release rcomp to megakaryocyte ploidy, is affected by TPO. Therefore, the transit time ($\tau_{MK}$) through the noted compartments is constant. Platelets also spend in average a constant time in the circulation ($\tau_{PL}$), which is not affected by TPO concentration (Ci).

In contrast, the transit times of the SC, CFU-Meg, and MKB compartments ($\tau_{SC}, \tau_{CFU}, \tau_{MKB}$, respectively) are functions of the micro-environmental conditions. Since cells that are far from maturation are not expected biologically to undergo a sudden shift to maturation, it seems that these functions determine the value the transit time should approach, rather than the actual transit time. The actual transit time changes gradually: every hour it changes by 1-2 hours towards the function-determined value. Thus, the mean of the value is determined, that transit time approaches rather than the transit time itself when speaking about transit time ($\tau$) calculations below.

a. SC Compartment:

It is assumed that regarding transit time ($\tau_{SC}$), the SC compartment differs from others in the same way as regarding amplification rate ($\alpha_{SC}$). It means that the cells of this compartment respond to TPO only when its concentration (Ci) rises above a threshold (θ). This threshold is the same as for the amplification rate ($\alpha_{SC}$). Below the threshold SC transit time is assumed to be regulated by a TPO-unrelated mechanism dependent on the current cell number ($q_{SCi}$) only. The function of this dependence changes the transit time from its minimal value ($\tau_{SCu}$) when the cell numbers ($q_{SCi}$) approach infinity, through the normal value that is greater than the minimal one by factor g, up to the highest value (($\tau_{SCmax}$) determined solely by biological reasons. This means that when the cell number in SC compartment ($q_{SCi}$) is relatively large, the cells will pass relatively rapidly to the next compartment, thus reducing the SC one; and they will remain longer in the SC compartment when their number ($q_{SCi}$) is low, thus repopulating it. This manner of regulation seems reasonable biologically.

It is suggested that similar to the amplification rate ($\alpha_{SC}$), the transit time ($\tau_{SC}$) in the range of very low cell numbers ($q_{SCi}$) (lower than a certain fraction (v) of the normal ($q_{SCnorm}$)), is very sensitive to further cell number decrease, and grows rapidly, thereby resisting compartment exhaustion. This fraction (v) is the same as for the SC amplification rate.

Following is an example of such a function:

$$\tau^*_{SC,i+1}(q_{SC,i}, C_i) = \qquad (11)$$
$$C_i \leq \theta$$

$$\begin{cases} \tau_{SCu}\cdot\left(1+(g-1)\cdot\left(\frac{q_{SCnorm}}{q_{SC,i}}\right)^{S_1}\right), & q_{SC,i} \geq v\cdot q_{SCnorm} \\ \tau_{SCmax} - (\tau_{SCmax}-\tilde{\tau}_{SC})\cdot\left(\frac{q_{SC,i}}{v\cdot q_{SCnorm}}\right)^{S_2}, & q_{SC,i} < v\cdot q_{SCnorm} \end{cases}$$

$$\tilde{\tau}_{SC} = \tau_{SCu}\cdot\left(1+(g-1)\cdot\frac{1}{v^{S_1}}\right) \quad \begin{vmatrix} S_{1,2} \geq 0 \\ \tau_{SCu} > 0 \\ g \geq 1 \\ 0 < v \leq 1 \end{vmatrix}$$

where $\tau^*_{SC,i+1}$ is the transit time calculated based on cell numbers ($q_{SC,i}$) only, i.e. when TPO concentration (Ci) remains below the threshold; $\tau_{SCu}$ is the minimal possible transit time through SC compartment in these circumstances; v is the fraction of normal cell number ($q_{SCnorm}$), below which the dependence of the transit time ($\tau^*_{SC,i+1}$) on the cell number ($q_{SC,i}$) changes; S1 and S2 are the sensitivity coefficients in the regions of $q_{SC,i}$ lower and higher than vqSCnorm, respectively.

If TPO concentration (Ci) in the model rises above the threshold, the transit time ($\tau_{SC}$) is assumed to shorten in a dose dependent manner. As for the amplification rate ($\alpha_{SC}$), its decrease is presumed to be proportional to the difference between actual TPO concentration (Ci) and the threshold. However, a shortening of the transit time down to zero by TPO is biologically illogical, so we assume that the transit time ($\tau_{SC}$) approaches some minimal value as TPO concentration (Ci) increases. In our model this minimum represents a fraction (k) of the transit time calculated on the basis of cell numbers ($\tau^*_{SC,i+1}$) as described earlier (equation (11)).

Following is an example of such an equation:

$$\tau_{SC,i+1}(q_{SC,i}, C_i) = \tau^*_{SC,i+1}(q_{SC,i}, C_i) \cdot k \cdot \left( \frac{1}{t \cdot \left(\frac{C_i - \theta}{C^* - \theta}\right)^t + \frac{k}{1-k}} + 1 \right) \quad (12)$$
$$C_i > \theta$$

$$0 < k \leq 1$$
$$t \geq 0$$

where $\tau_{SC,i+1}$ is the transit time when TPO concentration (Ci) is higher than the threshold; $\tau^*_{SC,i+1}$ is the transit time calculated on the basis of cell numbers as described in equation (11); k is the fraction of $\tau^*_{SC,i+1}$ that gives the minimum transit time approaches as TPO concentration (Ci) increases; C* determines the point of TPO concentration (Ci), around which the transit time ($\tau_{SC}$) is the most sensitive to concentration (C) change; t determines the steepness of the dependence curve (t is non-negative). Multiplication by t enables to regulate the sensitivity to Ci with t<1 in the same manner as when t>1.

b. CFU-Meg and MKB Compartments:

It is assumed that the transit time parameters of these two compartments ($\tau_{CFU}$, $\tau_{MKB}$, respectively) are dependent solely on TPO and respond to the absolute TPO concentration (Ci), rather than to its difference with a threshold (Ci−θ). As TPO level (Ci) drops, the cell passage through these compartments slows, i.e. transit time ($\tau_{comp}$) increases up to the values limited solely by biological reasons ($\tau_{comp,max}$) (it is assumed that the cells cannot stay in these compartments for an infinite period of time). On the other hand, when the TPO concentration (Ci) in the system increases, $\tau_{comp}$ does not shorten to zero, but rather asymptotically reaches $\tau_{comp,min}$, thus bounding the function from below. This also seems biologically reasonable, as the cells cannot move through the compartment in one instant. At normal TPO concentrations (Cnorm), we set $\tau_{comp}$ to equal its normal value ($\tau_{comp,norm}$). In addition, in order to enable the system to be sensitive both to the regulation by endogenously produced TPO and to the effect of the exogenously administered drug, it was assumed that the function changes relatively rapidly in the region of TPO concentrations (Ci) lower than normal ($C_{norm}$) and with a smaller rate when a TPO concentration (Ci) is higher than normal ($C_{norm}$). The following is an example of such a function:

$$\tau_{comp,i+1} = \quad (13)$$

$$\begin{cases} \tau_{comp,max} - (\tau_{comp,max} - \tau_{comp,norm}) \cdot \left(\frac{C_i}{C_{norm}}\right)^{t1}, & C_i \leq C_{norm} \\ (\tau_{comp,norm} - \tau_{comp,min}) \cdot \frac{2}{\left(\frac{C_i}{C_{norm}}\right)^{t2} + 1} + \tau_{comp,min}, & C_i > C_{norm} \end{cases}$$

$$0 < \tau_{comp,min} \leq \tau_{comp,norm} \leq \tau_{comp,max}$$
$$t_{1,2} \geq 0$$

where comp is one of the aforementioned compartments (CFU-Meg or MKB); $\tau_{comp,i+1}$ represents the transit times through these compartments; $\tau_{comp,min}$, $\tau_{comp,norm}$, and $\tau_{comp,max}$ are the minimal, normal and maximal transit times when TPO concentration is normal; t1 and t2 determine the steepness of the dependence curve in the regions of Ci lower and higher than Cnorm, respectively.

(4) TPO Effects on the Fraction of Cells that Flow from One Compartment to the Next.

The discussed parameter is the proportion of cells that passes to the next compartment at any given moment (φ). As was noted earlier, it is assumed that the fraction of the SC that commits to the megakaryocytic lineage ($\phi_{SC}$) is constant and TPO-independent. TPO in our model does not affect the two subsequent compartments, CFU-Meg and MKB.

In contrast, the fractions of MK16-, MK32-, and MK64-megakaryocytes that undergo additional endomitoses and flow to the next compartment ($\phi_{comp}$) are assumed to be in the range of 0 to 1 depending on TPO concentration (Ci). Because there is no compartment with ploidy greater than 128N, the megakaryocytes of the MK128 compartment do not flow to any other compartment.

The dependence of MK16, MK32, and MK64 φ parameters on TPO concentration assumed to be delayed with φ calculated based on TPO concentration prior to last endomitosis ($C_{i-\mu}$).

In the model, this dependence is expressed by a sigmoidal function with φ set to 0 when TPO concentration (Ci) is 0, equaling the normal value ($\phi_{norm}$) when TPO concentration is normal ($C_{norm}$), and approaching 1 asymptotically.

$$\varphi_{comp,i+1}(C_{i-\mu}) = 1 - \frac{C^t_{norm} \cdot \left(\frac{1}{\varphi_{comp,norm}} - 1\right)}{C^t_{i-\mu} + C^t_{norm} \cdot \left(\frac{1}{\varphi_{comp,norm}} - 1\right)} \quad (14)$$

$$0 \leq \varphi_{comp,norm} \leq 1$$
$$t, \mu \geq 0$$

where comp is one of the discussed compartments (MK16, MK32, or MK64); $\phi_{comp,i+1}$ is a φ parameter of these compartments; μ is the time needed for one additional endomitosis; $\phi_{comp,norm}$ is the value of $\phi_{comp}$ under normal TPO concentration ($C_{norm}$); t determines the steepness of the dependence function (t is non-negative).

The time needed for an additional endomitosis (μ) assumed to be the same in the three relevant compartments (MK16, MK32, and MK64).

IV.A.3. Complete Detailed Model

The complete model was built as an imitation of what happens in real bone marrow. Each compartment is subdivided into small sections that contain the cells of a specific age with a resolution of one hour. For example, the fifth age-section of MKB compartment 50 contains cells within MKB compartment 50 that have been within that compartment for 5 hours. Every hour, all the cells in the "bone marrow" pass to the next age-section in the same compartment.

When the cell has spent all the transit time predetermined for it in a given compartment, it passes to the next compartment to the zero age-section. Thus, every hour the cells that leave one compartment fill the zero age-section of the next one. The cells that leave MK128 compartment 90 die. The zero age-section of compartment 30 is filled by a certain fraction of the cells that leave SC compartment 30.

Figure 4:
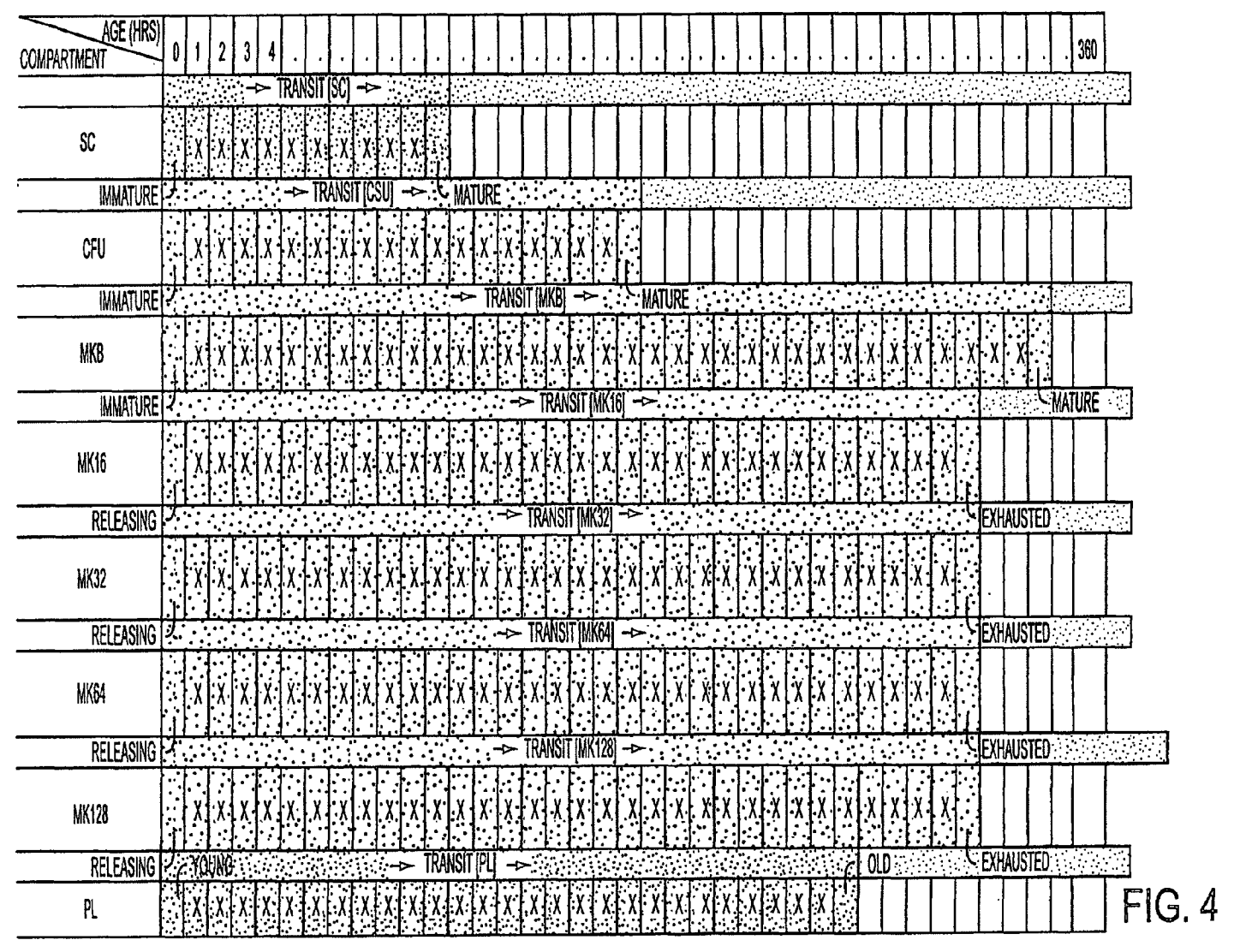

The cells that release platelets add a certain platelet number to the zero age-section of PL compartment 100 every hour. Reference is now made to FIG. 4, which is an illustration of the implementation of the model. The model is implemented as a chart of 8 rows and 360 columns. The 8 rows relate to 8 cell compartments, and the columns relate to the age sections, with the assumption that transit time does not exceed 360 hours. This chart is updated hourly according to the rules described above.

Figure 5:
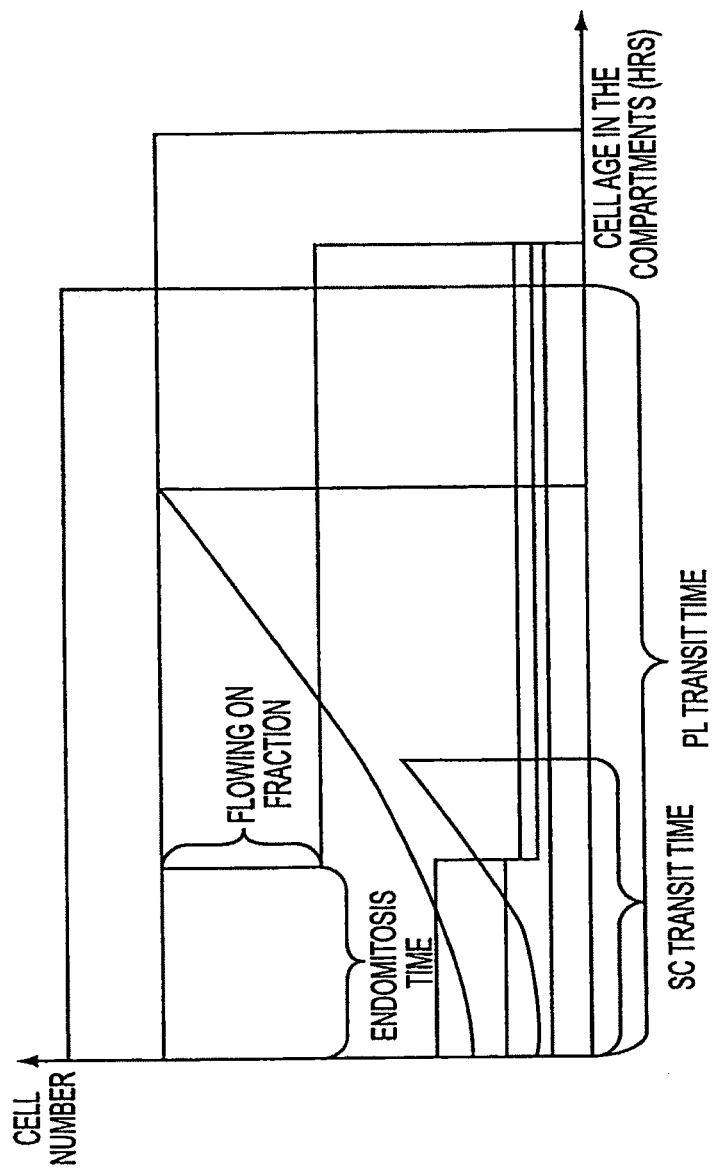
FIG. 5 is a graphical illustration of the chart of FIG. 4.

Reference is now made to FIG. 5, which shows a graphical representation of the chart of FIG. 4. Within the compartments where proliferation occurs (SC and CFU-Meg), the number of proliferating cells increases from the first to the last age-section. In contrast, the cell number in the compartments that have no proliferating ability remains constant (MKB, MK128, PL), or decreases when cells that have undergone additional endomitosis leave the compartment for the next one (MK16, MK32, MK64).

Figure 6:
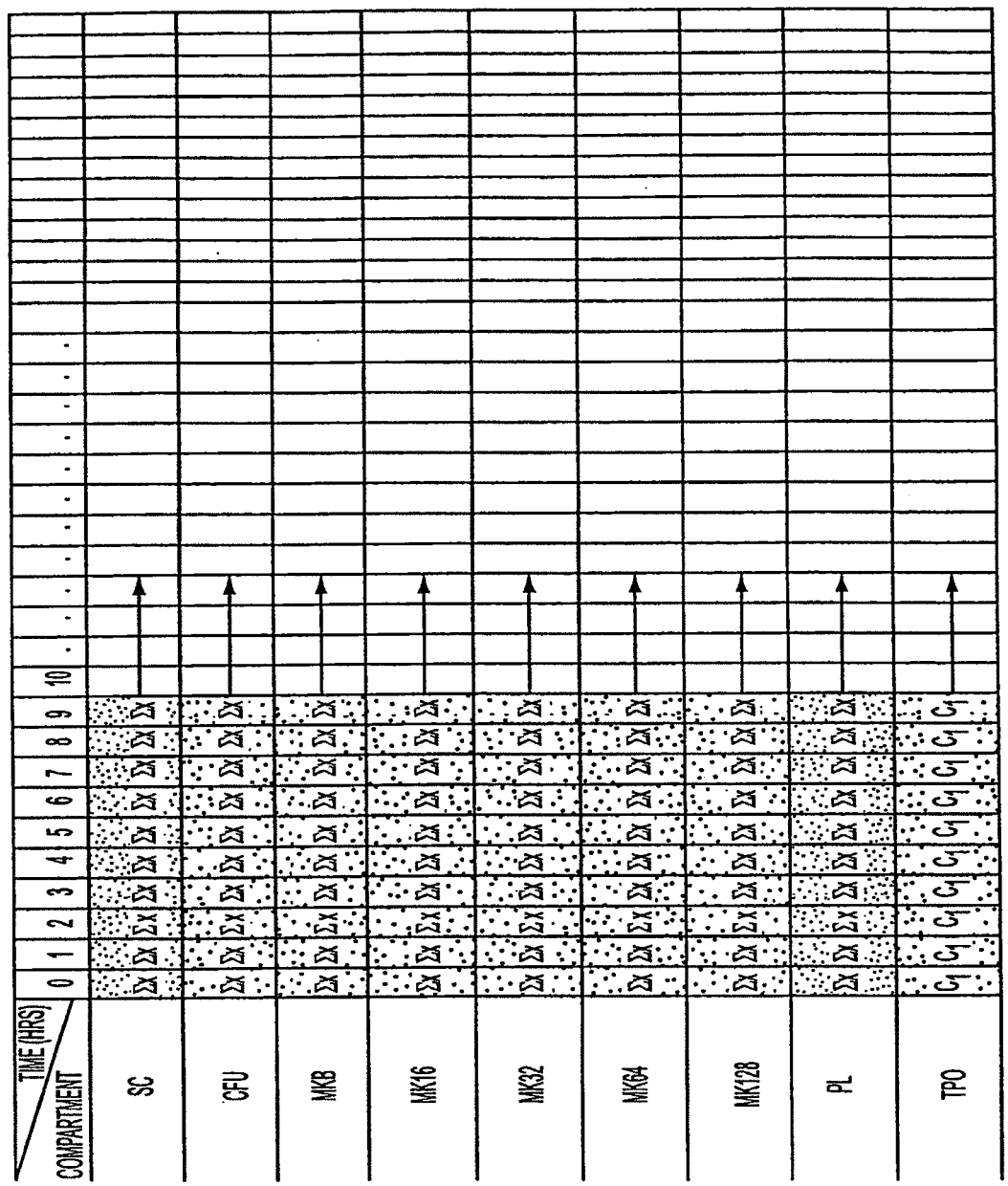
FIG. 6 is a chart illustration of the biological model of FIG. 3 in a different format.

Reference is now made to FIG. 6, which is an illustration of another representation of the model, based on the time courses of different compartments. The rows in the chart represent cell compartments and the columns represent time of simulation course. At every time-step of the simulation (one hour of "patient's life"), the number of cells in all age-sections is summarized for each compartment and the next column in time-course chart (FIG. 6) is filled. Thus, every cell in the chart represents the total number of cells in a given compartment at a given time point.

There is an additional row in the time-course chart that relates to the TPO concentration in the blood. TPO concentration is monitored and out-put every time-step concurrently with the cell numbers.

Figure 7:
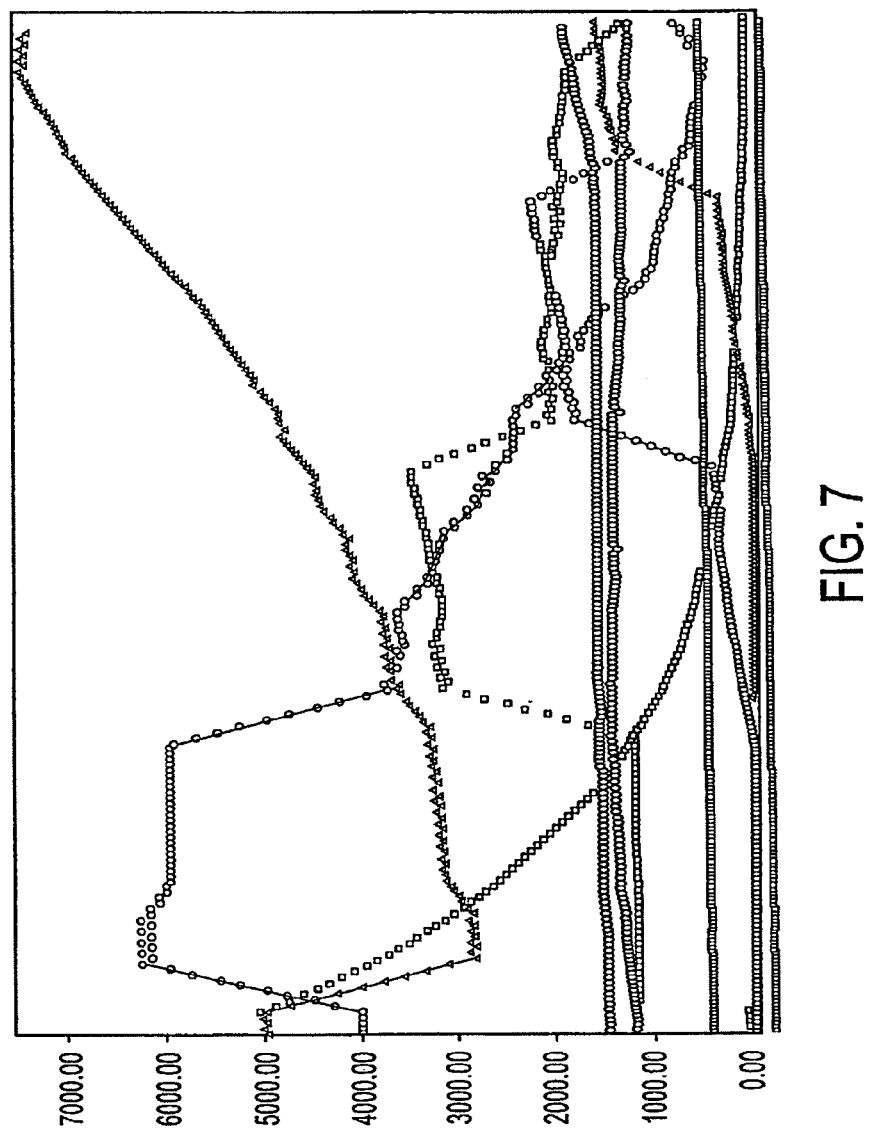
FIG. 7 is a graphical illustration of the chart of FIG. 6.
Figure 10:
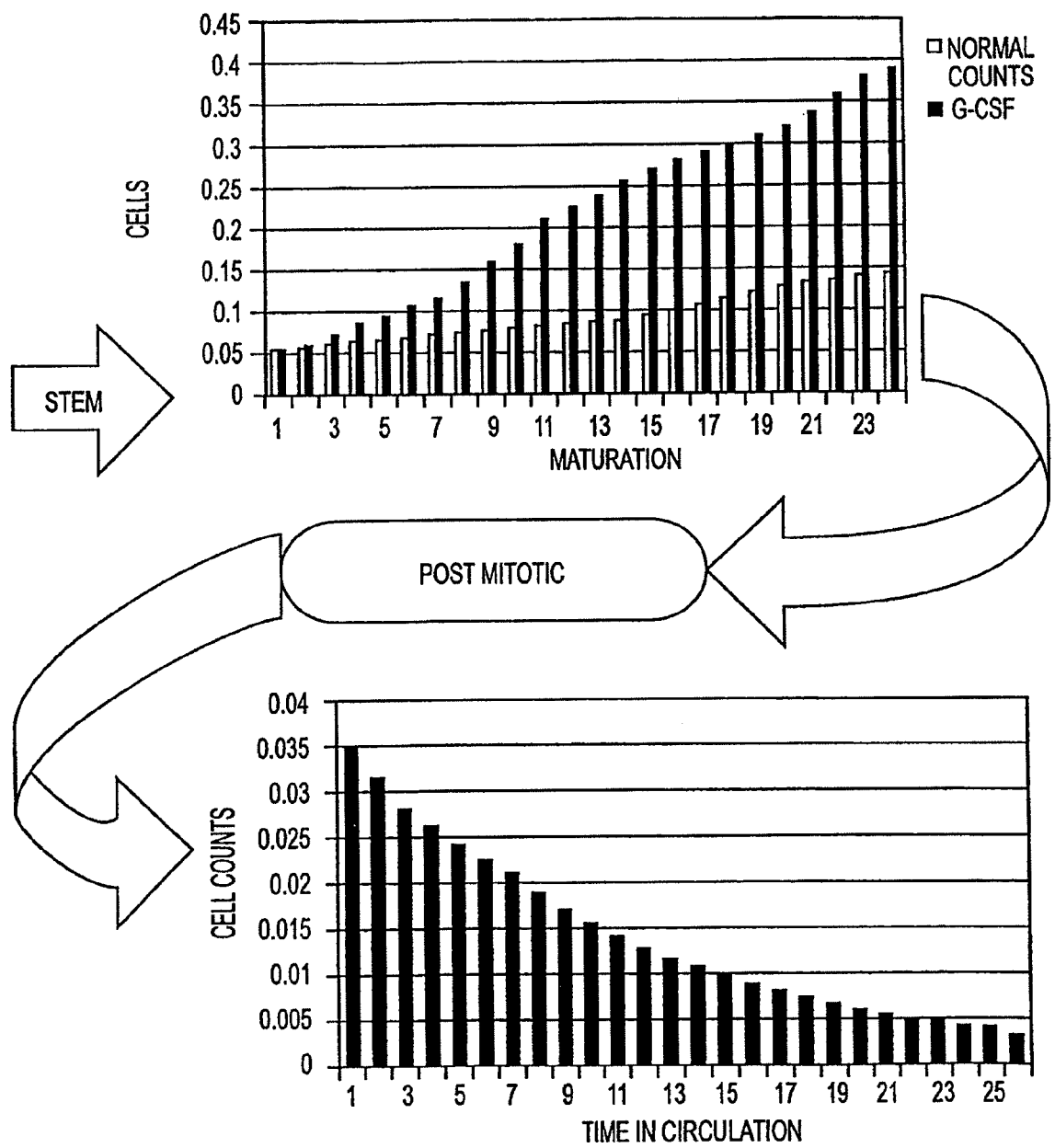
FIG. 10 is a schematic illustration of a biological model, in accordance with a further embodiment of the present invention.

Reference is now made to FIG. 7, which is a graphical representation of the chart of FIG. 6, and is the most useful model output The implementation of the described model results in a computer simulator that describes the changes that occur in the human Thrombopoietic system (platelet counts, bone marrow precursor numbers, and TPO concentration) over a time span that may last several years. The resolution of the simulator output is one hour.

Time units and periods that will mentioned hereafter relate to the simulated patient's life, rather to the running time of the program.

IV.A.4. Parameter-Specific Adaptation of Model

This model may be fit to patients with diverse blood and bone marrow parameters. People differ in their baseline platelet counts and numbers of bone marrow precursors, in the sensitivity of their stem cell "intrinsic" regulation mechanism, in their minimum and normal transit times and maximal amplification rates, rates of platelet release by megakaryocytes, fractions that each megakaryocyte ploidy class contribute for additional endocytosis, and the time needed for endomitosis ($\mu$). Furthermore, the baseline TPO level, the rate of TPO production, receptor- and non-receptor-mediated TPO clearance, the threshold of TPO effect on the SC compartment, and the sensitivity of different cell parameters to TPO also differ between patients.

To obtain an ideal fitness of the model to each patient, the patient-related parameters should be given individually for each patient. However, practically, it would be extremely difficult to predetermine many of these parameters for every patient. Therefore, certain average parameters have been calculated based on published data, and are shown in Table 1 below. These averaged parameters are used as a framework into which known individual characteristics are included. Thus, before a particular simulation is begun, relevant known information about the individual may be included, sometimes replacing certain parameters of the model.

TABLE

| COMMON PARAMETERS | | | | | | | | |
|---|---|---|---|---|---|---|---|---|
| | Compartment | | | | | | | |
| Parameter | SC | CFU-Meg | MKB | MK16 | MK32 | MK64 | MK128 | PL |
| $q_{norm}$ (×1000/kg body weight) | 480 | 650 | 5959 | 3900 | 1380 | 15 | 3 | 17,857,000 |
| $\tau_{min}$ ($\tau_\mu$ in SC) (hours) | 12 | 30 | 143 | — | — | — | — | — |
| $\tau_{norm}$ (hours) | — | 60 | 186 | 250 | 250 | 250 | 250 | 240 |
| $\tau_{max}$ (hours) | 350 | 360 | 360 | — | — | — | — | — |
| $\phi_{norm}$ (/hour) | 0.2846 | 1 | 1 | 0.2682 | 0.0128 | 0.1685 | — | — |
| c (platelets) | — | — | — | 4000 | 8000 | 16000 | 32000 | — |
| r (platelet/hr) | — | — | — | 11.19 | 22.38 | 44.76 | 89.52 | — |

| STEEPNESSES (t) OF THE TPO-SENSITIVITY CURVES | | | | | | | | | |
|---|---|---|---|---|---|---|---|---|---|
| $a_{SC}$ | $a_{CFU}$ | $\tau_{SC}$ | $\tau_{CFU}(t_1)$ | $\tau_{CFU}(t_2)$ | $\tau_{MKB}(t_1)$ | $\tau_{MKB}(t_2)$ | $\phi_{MK16}$ | $\phi_{MK32}$ | $\phi_{MK64}$ |
| 0.02 | 0.1 | 0 | $10^{-10}$ | 1 | 1 | 1 | 2 | 2 | 4 |

| SC-RELATED PARAMETERS | | | | | | | | |
|---|---|---|---|---|---|---|---|---|
| v | $S_1$ for $a_{SC}$ | $S_2$ for $a_{SC}$ | $S_1$ for $\tau_{SC}$ | $S_2$ for $\tau_{SC}$ | k | $a_{\tau v}$ | y | g |
| 0.01 | 0.5 | 0.5 | 1 | 0 | 0.5 | 1.116 | 0.25 | 5 |

TABLE-continued

| TPO-RELATED PARAMETERS | | | | | | |
|---|---|---|---|---|---|---|
| p (pg/ml) | θ (pg/ml) | f (/hr) | a (pg/ml/hr/ receptor molecule) | $C_{norm}$ (pg/ml) | ε (pg/ml) | C* (pg/ml) |
| 48 | 10,000 | 0.1 | 38 | 100 | 0.01 | θ + 50 |

| OTHER PARAMETERS | | | | | |
|---|---|---|---|---|---|
| μ (hours) | $m_{PL}$ | b | $a_{CFUmax}$ | h | d (fraction from each age-section per hour) |
| 16 | 220 | 220 | 1.204 | 0.125 | $2.59 \times 10^{-4}$ |

Usually, the known patient-related data are not parameters in the form defined by our model, but rather measurements obtained in the clinic (e.g., day and value of post-chemotherapy Thrombocytopenia nadir, day and value of platelet peak after TPO administration, change in megakaryocyte modal ploidy following some perturbation, etc.). In these cases, the available data is converted into a model-compatible format.

Sometimes, the only available patient-related data are the graphic representation of the patient's platelet course following some perturbation (e.g., cell-suppressive therapy or TPO administration). The data may also be a picture of the platelet course without any external disturbance (e.g., cyclic Thrombocytopenia). In these cases the model parameters are changed by trial-and-error until a good compliance of the model graphic output and the patient's graphs is achieved. It should be noted, however, that even in the case of trial and error, the choices of parameter sets are not random but rather are also based on some analysis.

Specifically, the following tools are available for providing maximum flexibility:
1) The user can set the baseline values and all other known patient-specific Thrombopoietic parameters before starting the simulation.
2) The user (e.g., physician) can determine how long of a time period to simulate, from a number of hours up to several years.
3) The user can determine the frequency of showing the course of a patient counts up to the moment. The frequency can change from as much as every 12 hours to once during the overall period of simulation.
4) The user can determine the resolution of the output graph, from the hourly representation of the patient's state down to any other resolution.
5) The user can choose to view the graphical representation of the age distribution through the compartments at any moment of the simulation.
6) The user can simulate a cell-suppressive therapy at any moment while running the simulation by reducing one or several of the compartments by any value.
7) The user can simulate exogenous TPO administration at any moment while running the simulation by controlling dose height, number of dosings or frequency of dosings.

The simulation tool has been carefully tested with respect to the published experimental results, and has proved to be well calibrated for average human data. Parameters may be modified relatively quickly for efficient use of the system. The following model parameters are important for individualized adjustment of the model:
  baseline number of: SC, CFU-Meg, MKB, MK16, MK32, platelets.
  amplification rate of: SC, CFU-Meg.
  transit time of: MKB, MK16, MK32, MK64.
  fraction undergoing additional endomitosis in: MK16, MK32, MK64.
  rate of platelet release of: MK16, MK32, MK64, MK128.
  Time needed for additional endomitosis.
  Rate of endogenous TPO production.
  Ratio of receptor- and non-receptor-mediated TPO clearance.
  Steepness of the sensitivity curve of: CFU-Meg amplification rate; MKB transit time; MK16, MK32, and MK64 fraction undergoing additional endomitosis.

Reference is now made to FIGS. 8A, 8B, 9A and 9B, which show a comparison between experimentally obtained data and the simulated model. Experimentally obtained in vivo platelet counts following TPO administration are shown in FIG. 8A and chemotherapy without TPO is shown in FIG. 9A. FIGS. 8B and 9B show simulations of the same. By using a TPO schedule designed by the described model, one can obtain platelet profiles that are similar to those obtained clinically (FIG. 8B) or even more effective (FIG. 9B). In this case, these results are achieved by administering a pre-calculated TPO protocol whose total dose amounts to 25% of the original total dose.

The complete model simulates cell and platelet counts in the steady state, as well as after perturbations to the haematopoietic system, e.g., cell-suppressive therapy, recombinant Thrombopoietin administration for uses such as platelets harvesting, etc. It is possible to simulate any protocol of drug administration and any haematological state of a patient, regarding his/her platelet count and number of bone marrow megakaryocytes and their precursors. The model can be adapted to many categories of patients, or healthy platelet donors. It can also be modified to fit species other than human. By providing specific parameters one can adjust the model so as to yield particular predictions about the Thrombopoietic profile of an individual patient. Other platelet disorders, such as cyclic Thrombocytopenia, may also be simulated.

IV.B. Neutrophil Production in the Bone Marrow and its Concentration in the Peripheral Blood Compartment Alone or Under the Effects of Growth-Factors and Treatment with Granulocyte Colony Stimulating Factor (G-CSF)

Another embodiment of the present invention involves the disclosed techniques for Neutrophil lineage, Granulopoietic disorders, including Neutropenia and its treatment with GCS-F. The Neutrophil lineage originates in pluripotent stem cells that proliferate and become committed to the Neutrophil lineage. These cells then undergo gradual maturation accompanied with further proliferation. The present model uses the state-of-the-art discrete compartmentalization of this continuous maturation-proliferation process, but is not restricted to it and can easily accommodate other modes of describing this continuous process using.

It is customary to divide the neutrophil maturation process in the bone to marrow into three morphologically distinguishable mitotic compartments: Myeloblasts, promyelocytes and myelocytes.

The myelocytes then mature and lose their capacity to proliferate, and thus enter the post mitotic compartment. In the post-mitotic compartment the cells continue their gradual maturation, which is not accompanied with proliferation through the three morphologically distinguishable sub-compartments: Metamyelocyte, band and segmented-Neutrophils. Cells exit the various sub-compartments in the post-mitotic compartment and enter the blood as Neutrophils. They then migrate from the blood to the tissues.

The Granulocyte-Colony Stimulating Factor (G-CSF) generates an increase in blood Neutrophil levels primarily by increasing production in the mitotic compartment and shortening the transit time of the post-mitotic compartment.

Thus, the first compartment of the mitotic pool (myeloblast) receives an inflow of cells from stem-cell precursors. Inflow for each of the other compartments is from outflow of the previous one, subject to multiplication factors due to cell replication in the mitotic stages.

Models regarding Granulopoiesis in normal humans and in humans with pathologies of the bone marrow were suggested previously in order to give a coherent description of the kinetics of Granulocytes from experimental data. For background details, see, Cartwright G E, Athens J W, Wintrobe M M. 1964. The kinetics of Granulopoiesis in normal man. Blood. 24(6): 780-803;

In recent years Schmitz et al. developed a kinetic simulation model for the effects of G-CSF on Granulopoiesis (for further details, see Schmitz, S., Franke, H., Brusis, J., Wichmann, H. E. 1993. Quantification of the Cell Kinetic Effects of G-CSF Using a Model of Human Granulopoiesis. Experimental Haematology. 21:755-760), and used it for the analysis of administration of G-CSF to patients suffering from cyclic Neutropenia (for further details, see Schmitz, S., Franke, H., Wichmann, H. E., Diehl, V. 1995. The Effect of Continuous G-CSF Application in Human Cyclic Neutropenia: A Model Analysis. British Journal of Haematology. 90:41-47). However, the data Schmitz rests upon for his model has been more accurately assessed in recent years by Price et al. and Chatta et al. For further details, see Price T H, Chatta G S, Dale D C. 1996. Effect of Recombinant Granulocyte Colony-Stimulating Factor on Neutrophil Kinetics in Normal Young and Elderly Humans. Blood. 88(1): 335-40; and Chatta G S, Price T H, Allen R C, Dale D C. 1994. Effects of in vivo Recombinant Methionyl Human Granulocyte Colony-Stimulating Factor on the Neutrophil Response and Peripheral Blood Colony-Forming Cells in Healthy Young and Elderly Adult Volunteers. Blood. 84(9): 2923-9. Actual empirical data regarding compartment sizes and their transit times was not incorporated into their model despite the importance of these data (For further details, see Dancey J T, Deubelbeiss K A, Harker L A, Finch C A. 1976. Neutrophil Kinetics in Man. J Clin Invest. 58(3): 705-15).

IV.B.1. Model of Neutrophil Lineage and Effects of G-CSF
a) G-CSF

The effects of G-CSF on the Neutrophil lineage are relayed in the model in three stages. The first is the administered amount of cytokine given at time t, which is marked: $G_{adm}^t$
The $G_{adm}$ vector serves as the control variable for optimization of G-CSF administration.

The second stage represents the pharmacokinetic behavior of G-CSF in circulation. It incorporates, for instance, the half-life of G-CSF, and could in the future be modified to express more of the effects of time on G-CSF activity. This level is marked: $G_{blood}^t$ G-CSF is eliminated from the blood in a Poissonic manner according to the following equation, as stated by Stute N, Furman W L, Schell M and Evans W E in "Pharmacokinetics of recombinant human Granulocyte-macrophage colony stimulating factor in children after intravenous and subcutaneous administration" Journal of Pharmaceutical Science, 84(7): 824-828, 1995:

$$G_{blood}^{t+1} = G_{blood}^t\left(1 - \frac{\ln 2}{\tilde{t}_{1/2}}\right) + G_{adm}^{t+1} \quad (14)$$

where $\tilde{t}_{1/2}$ is the half-life of G-CSF in the blood, and $G_{blood}^1 = G_{adm}^1$.

Recent data by Terashi K, Oka M, Ohdo S, Furudubo T, Ideda C, Fukuda M, Soda H, Higuchi S and Kohno S, in "Close association between clearance of recombinant human Granulocyte colony stimulating factor (G-CSF) and G-CSF receptor on Neutrophils in cancer patients", Antimicrobial Agents and Chemotherapy, 43(1): 21-24, 1999, points to the dependence of the half-life of G-CSF on Neutrophil counts. In the absence of exact kinetics of G-CSF effects on the Neutrophil lineage, the half-life is considered as a constant, though this could be modified should more exact information emerge.

Only exogenously produced G-CSF is considered to affect the kinetic parameters, and endogenously produced G-CSF levels and effects are set to zero. If more empirical data regarding the production of endogenous G-CSF is made available, it could be incorporated into the equation as well.

The third and final stage models the pharmacodynamic effects of G-CSF on the kinetic parameters. As will be elaborated subsequently, the dependence of the various kinetic parameters of the Neutrophil lineage on the level of G-CSF in the blood is assumed to be through either non-decreasing concave or non-increasing convex functions. This reproduces the effects of saturation that are seen in clinical studies on the effects of G-CSF, such as the study by Duhrsen U, Villeval J L, Boyd J Kannourakis G, Morstyn G and Metcalf D in "Effects of recombinant human Granulocyte colony-stimulating factor on haematopoietic progenitor cells in cancer patients", Blood, 72(6): 2074-2081, 1988. That is, addition of G-CSF carries a lesser effect when its level in circulation is already high.

b) Biological Mode
(1) Mitotic Compartment

Long-term effects of G-CSF administration take place in the mitotic compartment. Although the major contributor to heightened blood Neutrophil counts in the short term is the post mitotic compartment's shortening of transit time due to G-CSF administration, this high level cannot be maintained over the long term without increased production in the mitotic compartment.

The mitotic compartment is divided into subcompartments. The kth subcompartment contains all cells of chronological age between k−1 and k hours, relative to the time of entry into the mitotic compartment. The number of cells in subcompartment k at time t is marked as $m_k^t$.

$k \in \{1 \ldots \tau\}$ $$m_1^t = l_1^t(G_{blood}^t) \quad (15)$$

where τ is the transit time of the entire mitotic compartment, and is assumed to be the same and constant for all cells entering the mitotic compartment, and $l_1$ is a vector reflecting the flow of newly committed cells into the mitotic compartment. The biological grounds for this definition is the existence of a myeloid stem cell reservoir, which is known to supply new committed cells to the mitotic compartment. However, the reservoir's actual kinetics are not very well explored empirically. Therefore $l_1$ is fixed to levels such that the overall size of the mitotic compartment as well as the kinetics of the Neutrophils in circulation would match those obtained empirically.

Any new biological data that emerges may help define the kinetics more accurately within the framework of this model, although results of this model indicate that the assumption of a constant rate of stem cells flowing into the mitotic compartment in the absence of G-CSF is plausible. For every $n \in \{1 \ldots \tau\}$ and for every t, amplification occurs at the exit from $m_n^t$, according to Equation 15 as follows:

$$m_{n+1}^{t+1} = m_n^t \cdot \alpha_n(G_{blood}^t) \qquad (16)$$

where:
$\alpha_n$ is a non-decreasing concave function of G-CSF levels in the blood, which determines the factor of amplification in the hourly subcompartment n. If, for instance, no amplification occurs at subcompartment $n_0$ at time t then $$\alpha_{n_0} = 1$$

$$\forall n, G_{blood}^t 1 \leq \alpha_n(G_{blood}^t) \leq 2$$

(17) The size of the morphological sub-compartments in the mitotic compartment at time t is determined as: (18)

$$\sum_{n=n_0}^{n_1} m_n^t$$

Where $n_0$ is the first hourly sub-compartment of a morphological sub-compartment and $n_1$ is its last hourly sub-compartment. The division into the morphological sub-compartments is used only for fine-tuning of the kinetic parameters with the use of experimental data.

The mitotic compartment was modeled with an intention to facilitate the specific cell-cycle cytotoxic effects of chemotherapy. Therefore, cohorts of one hour are modeled as undergoing a process of maturation and amplification culminating in their entry into the post-mitotic as described below. Effects of chemotherapy may be incorporated into the model by mapping the various cell-cycle phases (G1, S, G2, M) to the hourly cohorts modeled and formulating a function of the cytotoxic effects of chemotherapy on these phases.

The experimental literature shows wide agreement regarding the steady state normal amounts of circulating Neutrohpils, size of the post-mitotic compartment and the three morphologically distinct sub-compartments of the mitotic compartment, and post-mitotic transit time and amplification rates in the mitotic sub-compartments (see, for example, Dancey J T, Deubelbeiss K A, Harker L A and Finch C A, in "Neutrophil kinetics" in Man. Journal of Clinical Investigation, 58(3): 705-715, 1976; Price T H, Chatta G S and Dale D C, "Effect of recombinant Granulocytee colony-stimulating factor on Neutrophil kinetics in normal young and elderly humans", Blood 88(1): 335-340, 1996; and Dresch Mary in "Growth fraction of myelocytes in normal human Granulopoiesis", Cell Tissue Kinetics 19: 11-22, 1986). To determine other relevant kinetic parameters, which were either not available in the literature or were given a wide range by experimentalists, steady state kinetics was assumed and an iterative process was employed. These parameters include the inflow of stem cells to the myeloblast compartment and the transit times of the mitotic sub-compartments.

The half life of blood Neutrophils and the steady state number of Neutrophils were taken as 7.6 h and $0.4 \times 10^9$ cells/kg body weight, respectively (taken from Dancey J T, Deubelbeiss K A, Harker L A, Finch C A. 1976. Neutrophil Kinetics in Man. J Clin Invest. 58(3): 705-15). Similarly, the same calculation may be made for each patient that is to be modeled. This would allow the dynamics of every patient to be described by the simulation. The average size of the post-mitotic compartment ($5.84 \times 10^9$ cells/kg body weight—Dancey J T, Deubelbeiss K A, Harker L A, Finch C A. 1976. Neutrophil Kinetics in Man. J Clin Invest 58(3): 705-15) and the transit time of the compartment (160 h—Dancey J T, Deubelbeiss K A, Harker L A, Finch C A. 1976. Neutrophil Kinetics in Man. J Clin Invest. 58(3): 705-15; Dresch, Mary. 1986. Growth Fraction of Myelocytes in Normal Human Granulopoiesis. Cell Tissue Kin. 19: 11-22; Price T H, Chatta G S, Dale D C. 1996. Effect of Recombinant Granulocyte Colony-Stimulating Factor on Neutrophil Kinetics in Normal Young and Elderly Humans. Blood. 88(1): 335-40) are compatible with the size and half-life of the circulating Neutrophil compartment reported by Dancey, thus supporting the steady state analysis.

In order to determine the amount of cells in the hourly sub-compartments in the mitotic compartment, all compartments in the lineage were modeled using a steady state assumption. The number of cells exiting the circulating Neutrophil pool equals the number of cells exiting the post mitotic compartment, which in turn equals the hourly production of cells in the mitotic compartment. Thus, the number of cells in the last hourly cohort of the mitotic compartment can be determined from the Neutrophil decay rate, which is available in the literature. However, this calculation is based on assumptions that there is no apoptosis in the post-mitotic compartment. Direct experimental data by Thiele J, Zirbes T K, Lorenzen J, Kvasnicka H M, Scholz S, Erdmann A, Flucke U, Diehl V and Fischer R, in "Haematopoietic turnover index in reactive and neoplastic bone marrow lesions: Quantification by apoptosis and PCNA labeling," Annals of Haematology 75(1-2): 33-39, 1997, suggests that apoptosis is not a significant phenomenon in normal human bone marrow. The size calculated for the mitotic compartment is close to that experimentally obtained by Dancey and Price, thus supporting the notion that apoptosis is not a significant kinetic factor in the lineage. Values for the production of cells in the mitotic compartment can later be modified in light of new evidence.

Regarding the transit time of the mitotic compartment there is little agreement in the literature, with a range of 90-160 hours given by most experimentalists (see Dresch Mary in "Growth fraction of myelocytes in normal human Granulopoiesis," Cell Tissue Kinetics 19: 11-22, 1986). In order to determine the transit times of the mitotic morphological sub-compartments, as in Equation 18, the following constraints were considered:

1. The sizes of the theoretically obtained morphological sub-compartments must fit those reported experimentally in normal human haematopoiesis (Dancey J T, Deubelbeiss K A, Harker L A, Finch C A. 1976. Neutrophil Kinetics in Man. J Clin Invest. 58(3): 705-15) and under the effects of G-CSF (Price T H, Chatta G S, Dale D C. 1996. Effect of Recombinant Granulocyte Colony-Stimulating Factor on Neutrophil Kinetics in Normal Young and Elderly Humans. Blood. 88(1): 335-40);
2. At least 24 hours, the typical cell cycle, must separate amplification points;

3. The size of the last hourly sub-compartment must equal the hourly production of the mitotic compartment (calculated with the aforementioned iterative process assuming steady state kinetics);
4. Amplification inside the compartment is set at the levels determined by Mary, J. Y. 1984. Normal Human Granulopoiesis Revisited I. Blood data, II. Bone Marrow Data. Biomedicine & Pharmacotherapy. 38: 33-43, 66-67; and
5. The total transit time of the mitotic compartment must be within the 90-160 hour range.

By using the values shown in Table x, an excellent fit was obtained within the above-mentioned constraints.

It should be noted that when other alternatives with shorter transit times were attempted, results could not be obtained that agreed with the literature regarding the size of the mitotic pool or its production. Furthermore, a fit between our simulation model's results regarding Polymorphonuclear (PMN) cell counts in peripheral blood with empirical data could not be achieved without speculating extensively on the nature of G-CSF effects on non-committed stem cells. It should be noted, that little empirical quantitative data is available regarding stem cells.

The effects of G-CSF on this compartment are modeled as an increase in the rate of cells entering the myeloblasts from the uncommitted stem cell pool, increases in the rates of mitosis, and introduction of new points of amplification as shown in Equation 15, 16. Since little data is available regarding the increases in amplification due to G-CSF, an initial assumption was made that amplification reaches full potential at points that under normal conditions undergo an amplification of below a factor of 2. Additionally, it was assumed that the transit time in all mitotic sub-compartments and the typical cell cycle duration are not affected by G-CSF, based on lack of evidence to the contrary.

Figure 14:
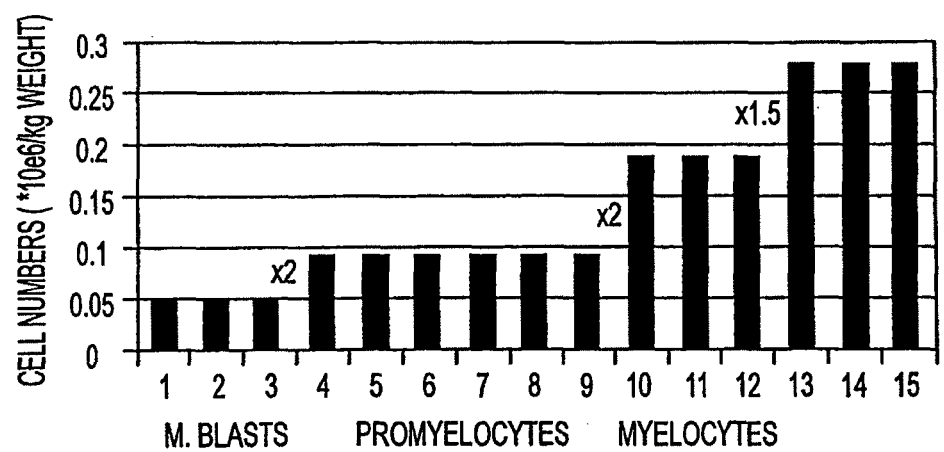
FIGS. 14 and 15 show a comparison of Neutrophil production according to the described model and experimental data in the literature.
Figure 15:
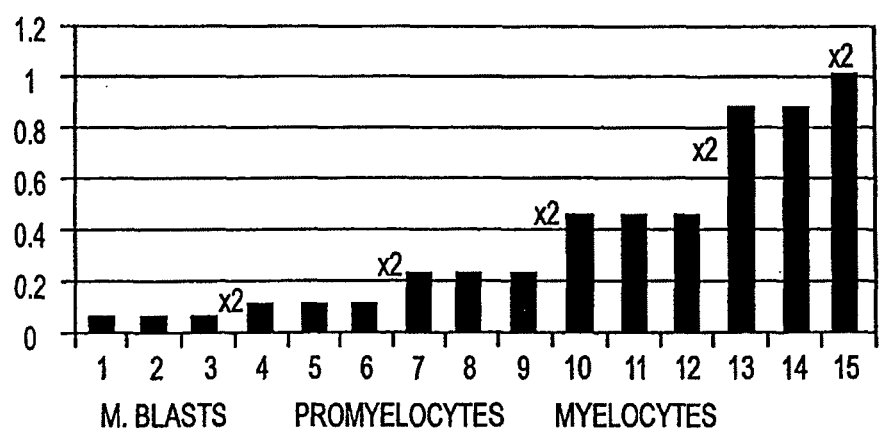

Reference is now made to FIGS. 14 and 25 which show a comparison of Neutrophil production according to the described model and experimental data in the literature. Increased Neutrophil production is in accordance with the Neutrophil counts reported by Price et al. In addition, these increases are in accordance with Price's data about Neutrophil bone marrow pool sizes.

Reproduction of the effect of G-CSF on Neutrophil counts and the mitotic compartment sizes beyond day 5 of administration was accomplished by assuming an increase (15% with the highest dose of G-CSF) in the rate of cells entering the myeloblast compartment. Alternatively, G-CSF may change the behavior of the myeloblast compartment such that some of the cells there undergo self-renewal instead of moving on to the promyelocyte compartment. However, no empirical data to support this is available. The model can be modified in light of new experimental data in the future.

(2) Post-Mitotic Compartment

The different post mitotic compartments seem indistinguishable in insensitivity to cytotoxic chemotherapy. Therefore, it is biologically acceptable and computationally sensible to model this compartment as a single pool of cells, such that the last hourly cohort of the mitotic compartment enters the compartment, and a proportion of the cells within the compartment enter the Neutrophil pool every hour.

The post mitotic compartment at time t is a single quantity of cells $p^t$, such that:

$$p^{t+1} = l_3(G_{blood}^t) \cdot p^t + m_\tau^t \quad (19)$$

where $l_3$ is a convex, non-increasing function of G-CSF levels in the blood, which takes values in the range of [0-1]. This definition entails $p^t > 0$.

We shall mark as $o^t$ of the outflow from the post mitotic compartment:

$$o^t = m_\tau^i + p^t - p^{t+1} \quad (20)$$

The number of Neutrophils in the circulating blood compartment at time t is marked nt and is modeled as a single quantity of cells, such that:

$$n^{t+1} = o^t + n^t\left(1 - \frac{\ln 2}{t_{1/2}}\right) \quad (21)$$

where $t\frac{1}{2}$ is the half-life of Neutrophils in the blood, as defined in the biological literature. $t\frac{1}{2}$ is assumed to be held constant regardless of G-CSF levels (Lord B. I, Bronchud, M. H., Owens, S., Chang, J., Howell, A., Souza, L., Dexter, T. M. 1989. The Kinetics of Human Granulopoiesis Following Treatment with Granulocyte Colony-Stimulating Factor in vivo. Proc. Natl. Sci. USA. 86: 9499-9503), though this could be easily modified. The kinetics of Neutrophils in the tissues are not modeled in this work.

This model will be incorporated into an optimization scheme that will have as its objective function both the aims of minimizing G-CSF administration and returning the Neutrophil lineage to its normal levels.

At $G_{blood}^t = 0$, $p^t = \Pi$, $m_\tau^t$ at the normal healthy level we have the following obvious relationship:

$$\frac{\Pi}{T} = m_\tau^t = o^t = \frac{n^t}{t_{1/2}} \times \ln 2 \quad (21)$$

Which reflects the stability of the steady state.

G-CSF affects the post-mitotic compartment by shortening its transit time (i.e. decreasing $l_3$). Price notes that the number of cells in the post mitotic compartment is not significantly changed following administration of G-CSF. This determination is based on counts made on day 5 after G-CSF administration. Thus, it can be safely assumed that any increased production of the mitotic compartment flowing into the post mitotic compartment is translated over the long-term to an increase in the flow of cells from the post mitotic compartment to the Neutrophil pool. This increased flow is compensated by increased production in the mitotic compartment only at a later stage. Therefore, an upper limit to the number of cells in the post mitotic compartment was set, which is at the values given as steady state counts (Π).

In brief, the effects of G-CSF on the Neutrophil lineage are modeled during the first few days primarily as a decrease in the counts of the post-mitotic compartment, which is then compensated by an increased production in the mitotic pool. This compensation sustains the increase in Neutrophil counts in peripheral blood.

Figure 11:
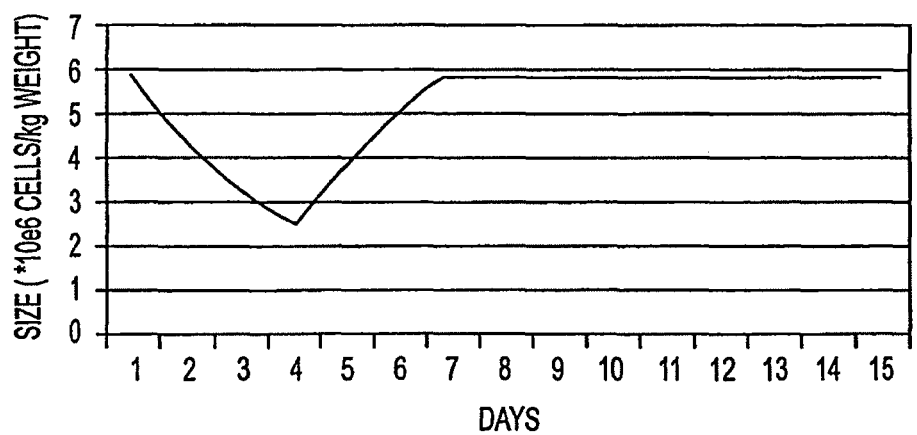
FIG. 11 is a graphical illustration of results of the simulation of the model shown in FIG. 10.

Reference is now made to FIG. 11, which is a graphical illustration of a simulation of the model. Though no empirical data is available on this point, simulations of the model predict that the number of cells in the post-mitotic compartment decreases substantially during the first two days of G-CSF administration, and then replenishes, so that on the sixth day the counts return almost to their normal levels. This replenishment lags behind that of Price et al report by a few hours. A testable hypothesis can thus be formulated, i.e., whether using the same G-CSF protocol Price et al used, there is indeed a nadir on day 3 of the treatment.

TABLE 1

Simulated kinetics after 15 days of subcutaneous administration of 300 μg G-CSF/kg weight.

| Compartment | Day 0 (no G-CSF) (×10⁹ cells/kg. Body weight) | Day 15 of G-CSF treatment (×10⁹ cells/kg. body weight) | Relative increase in compartment size due to G-CSF |
|---|---|---|---|
| Myeloblasts | 0.140 | 0.153 | 1.09 |
| Promyelocytes | 0.582 | 0.898 | 1.54 |
| Myelocytes | 1.373 | 3.564 | 2.60 |
| Mitotic Total = | 2.10 | 4.615 | 2.20 |
| Circulating Neutrophils | 0.4 | 2.35 | 5.88 |

Day 0 values are the mean values Dancey et al (1976) use.

IV.B.2. Neutrophils and G-CSF in the Circulating Blood

The elimination of Neutrophils from peripheral blood follows a Poisson distribution, and can therefore be described as an exponential function, as shown by Cartwright G E, Athens J W, Wintrobe M M. 1964. The kinetics of Granulopoiesis in normal man. Blood. 24(6): 780-803. Therefore the rate of cells leaving this compartment is based on half-life determinations available in the literature. Since no direct cytotoxic effects of chemotherapy have been described for this compartment it is also modeled as a single pool of cells.

The kinetics of G-CSF is also modeled as an exponential distribution with a half-life of 3.5 hours (Eq. 14).

The effects of G-CSF on the kinetics of the Neutrophil lineage appear not to be a linear function of G-CSF administration levels. Since data provided in the literature (Chatta G S, Price T H, Allen R C, Dale D C. 1994. Effects of in vivo Recombinant Methionyl Human Granulocyte Colony-Stimulating Factor on the Neutrophil Response and Peripheral Blood Colony-Forming Cells in Healthy Young and Elderly Adult Volunteers. Blood. 84(9): 2923-9) only refers to two doses (30 and 300 μgram/kg body weight) we can only speculate on the effects of other levels of G-CSF. After trial and error analysis, it was found that assuming that the effects of the 300-μgram dose are the maximal, at the 30-μgram its effects are about 30% of the maximum.

Figure 12:
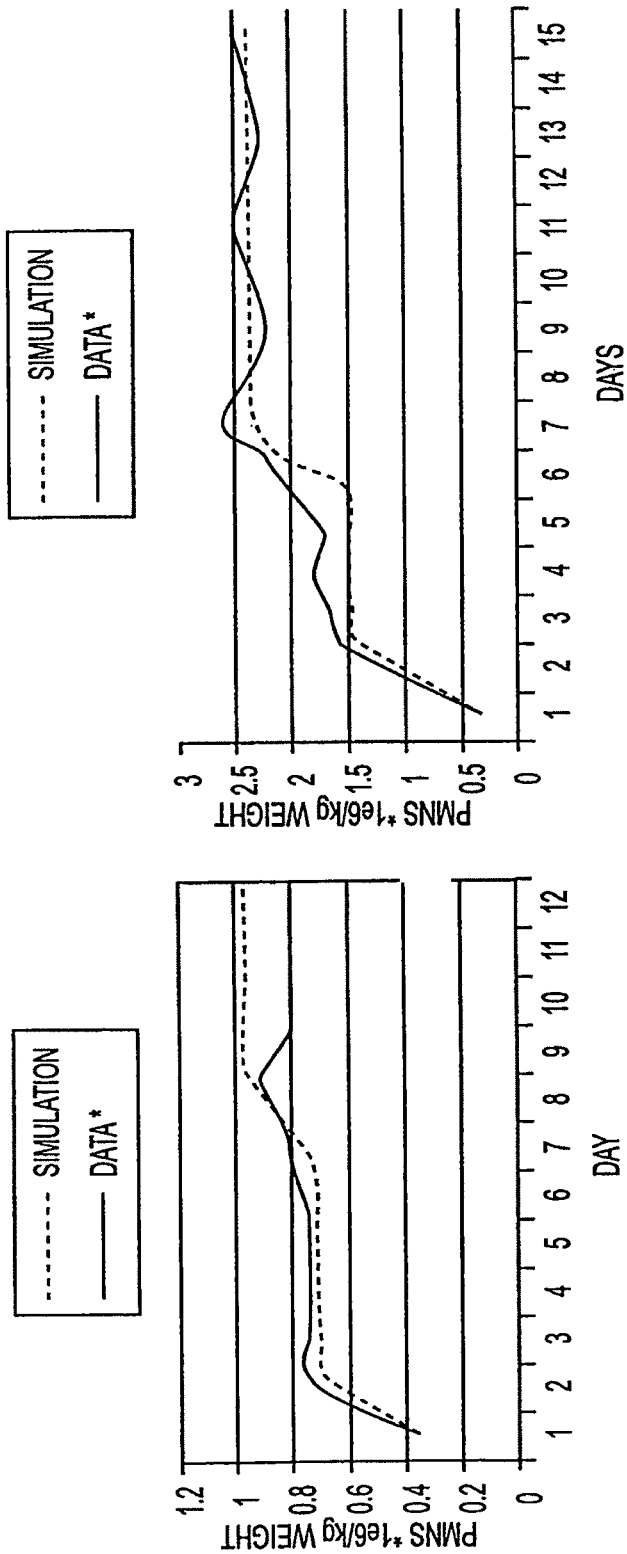
FIGS. 12A and 12B are graphical illustrations of the effects of two doses of G-CSF on the Neutrophil line, according to the model of FIG. 10.

Reference is now made to FIGS. 12A and 12B, which are graphical illustrations of the effects of G-CSF at the two doses. The effects as a function of G-CSF level are connected piece-wise linearly. This way, the Neutrophil levels observed clinically under both the 300 and the 30-μgram protocols are obtained.

IV.C. Linear Implementation of the Model

Another embodiment of the present invention is the implementation of the above model by incorporating it into an optimization scheme that has as its objective function both the aims of minimizing G-CSF administration and returning the Neutrophil lineage to its normal levels.

Although the above-outlined model may be implemented in any number of optimization methods, the disclosed embodiment using linear programming was chosen because of its inherent advantages compared with some other techniques, i.e. its ability to provide an optimal solution using partially analytical methods, and therefore being more computationally tractable (Gill 1991). On the other hand, implementation of this model in linear programming carries with it the disadvantage that certain computations must be approximated linearly since they cannot be performed directly using linear methods. Thus, we shall compare the 'closeness' of the solution obtained through linear programming with that obtained through another, non-linear method of optimization.

The significant parts of the model that must be modified due to the linear programming implementation are the sections in which multiplication of two $\{(x_{min},y_{min},x_{min}\cdot y_{min}),$ $(x_{min},y_{max},x_{min}\cdot y_{max})$, $(x_{max},y_{min},x_{max}\cdot y_{min})$, $(x_{max},y_{max}, x_{max}\cdot y_{max})\}$ variables is defined, since this operator is not itself linear. Therefore, multiplication is defined as an approximated value constrained within piecewise linear constraints that most closely bound the product within a four-faced to polyhedron in 3-dimensional space whose vertices are Where $x_{min}$, $x_{max}$, $y_{min}$, $y_{max}$ are the constant biologically defined minima and maxima of x and y.

$$M(x,y) \begin{cases} \geq y_{min}x + x_{min}y - x_{min}y_{min} \\ \geq y_{max}x + x_{max}y - x_{max}y_{max} \\ \leq y_{min}x + x_{max}y - x_{max}y_{min} \\ \leq y_{max}x + x_{min}y - x_{min}y_{max} \end{cases} \quad (22)$$

Multiplication may also be approximated with variations on the linear least squares method, by finding one plane that's closest to the four vertices defined.

The other functions that need to be defined linearly are those concerning the pharmacodynamics of G-CSF. Due to the nature of these functions (either non-increasing convex or non-decreasing concave), these effects are implemented as piece-wise linear functions whose breakpoints are the doses for which actual experimental data is available (Chatta G S, Price T H, Allen R C, Dale D C. 1994. Effects of in vivo Recombinant Methionyl Human Granulocyte Colony-Stimulating Factor on the Neutrophil Response and Peripheral Blood Colony-Forming Cells in Healthy Young and Elderly Adult Volunteers. Blood. 84(9): 2923-9). Note that the effects of G-CSF on each of the kinetic parameters have not been determined in a detailed manner by experimentalists. Rather its effects over a few dose levels on the Neutrophil blood counts and the size of the morphologically different mitotic compartments and the post mitotic compartment have been determined. From these data, the effects of G-CSF on the actual kinetic parameters (probability of mitosis, transit time and inflow of cells into the myeloblast compartment from stem cell progenitors) has been reconstructed at the dose levels available in the literature. These points are then connected linearly to obtain piecewise linear functions relating G-CSF levels to their effect on those parameters. Further experimental data in the future could be used to produce more accurate functions.

At the amplification points within the mitotic compartment, the linearly approximated multiplication operator (Eq 22) is used instead of the product defined in Eq. 16.

At points where no amplification occurs the quantity from one compartment is simply transferred to the next according to the following Equation:

$$m_{n+1}^{t+1} = m_n^t \quad (23)$$

$$m_n^0$$

Values are set according to the steady state values of the mitotic compartment, or are depleted according to the kill function of the chemotherapy.

The flow out of the post mitotic compartment (Eq. 20) is similarly defined as a linear approximation of a product.

IV.C.1. Formulation of the Model as an Optimization Problem for Linear Programming The simulation spans a finite number of discrete time steps denoted by T.

We define as the control variable the vector that represents G-CSF administration at every given hour t: $G_{adm}^t \in \{1 \ldots T\}$ The objective function is defined as maximization of the following expression:

$$\sum_{t=1}^{T} (\beta^t \cdot p^t - G_{adm}^t) \quad \text{(Eq. 24)}$$

where $p^t$ is the number of cells in the post mitotic compartment at time t, and β is a scalar weighting coefficient. The logic for formulating the objective function this way is that the ability to maintain the post mitotic compartment's steady state size for a prolonged period of time is sufficient for rehabilitation of the Neutrophil lineage as a whole. Also, our goal is to minimize the total administered quantity of G-CSF. β is introduced to allow us to factor in both these goals in one objective. Also, this would allow a different weight to be given for certain times, e.g. were it determined (by clinicians) that the later states of the post-mitotic compartment should be weighted more than the first ones. Obviously this is only one of the possible formulations of the objective function as defined in the previous section.

The pharmacokinetics and pharmacodynamics of G-CSF that were defined generally in the mathematical model are defined piecewise linearly. Some of the considerations that was put into formulating these functions were based directly on experimental evidence (elaborated in the main body of text). It is noted however, that actual experimental data regarding the direct effects of G-CSF on the kinetic parameters in which this model is interested is rather scant. Therefore, some formulations were conducted through partly analytic and partly trial-and-error methods.

The formulation of the model in piecewise linear terms will allow use of this model as a clinical tool in three ways. First, the model will determine the effectiveness of various protocols suggested by clinicians prior to their actual use on human patients. Second, the model allows computation of the optimal protocol in a given situation of Neutrophil counts, so that the e.g., Neutropenic period following chemotherapy is either shortened or completely avoided at a minimal cost and exposure to G-CSF. Third, the model serves as a constituent in a broader framework of clinical tools that will compute the most optimal treatment plan for chemotherapy and growth factors. These uses should help clinicians administer more rational treatment to their patients minimizing both suffering and medical costs.

TABLE 1

Kinetics under steady state conditions in healthy humans.

| Amplification at the exit | Mean transit time (hours) | Size ($10^6$ cells/kg weight) | Compartment |
|---|---|---|---|
| $2^+$ | $24^-$ | 0.139* | Myeloblasts |
| $2^+$ | $48^-$ | 0.558* | Promyelocytes |
| $1.5^+$ | $48^-$ | 1.4* | Myelocytes |
| 1 | 160* | 5.84* | Post mitotic |
| 0 | 10.96* | 0.4* | Neutrophils |

*Dancey, 1976.
+Dresch, 1986.
−Calculated based on the steady state assumption as elaborated in the main text.

IV.D. Cancer and Treatment with Cytotoxic Drug Delivery

IV.D.1. Introduction

Still another embodiment of the present invention deals with cancer and its treatment using chemotherapy. Cancer is the second leading cause of mortality in the US, resulting in approximately 550,000 deaths a year. There has been a significant overall rise in cancer cases in recent years, attributable to the aging of the population. Another contributing factor to the rise in the verifiable number of cases is the wider use of screening tests, such as mammography and elevated levels of prostate specific antigen (PSA) in the blood.

Neither better detection nor the natural phenomenon of aging, however, can entirely explain the increase in new cases of tumors. Meanwhile, other cancers, like brain tumors and non-Hodgkin's lymphoma, are becoming more common. Their increase could reflect changes in exposures to as yet unidentified carcinogens. Current trends suggest that cancer may overtake heart disease as the nation's no. 1 killer in the foreseeable future. As gene therapy still faces significant hurdles before it becomes an established therapeutic strategy, present control of cancer depends entirely on chemotherapeutic methods.

Chemotherapy is treatment with drugs to destroy cancer cells. There are more than 50 drugs that are now used to delay or stop the growth of cancer. More than a dozen cancers that formerly were fatal are now treatable, prolonging patients' lives with chemotherapy.

Treatment is performed using agents that are widely non-cancer-specific, killing cells that have a high proliferation rate. Therefore, in addition to the malignant cells, most chemotherapeutic agents also cause severe side-effects because of the damage inflicted on normal body cells. Many patients develop severe nausea and vomiting, become very tired, and lose their hair temporarily. Special drugs are given to alleviate some of these symptoms, particularly the nausea and vomiting. Chemotherapeutic drugs are usually given in combination with one another or in a particular sequence for a relatively short time.

Chemotherapy is a problem involving many interactive nonlinear processes which operate on different organizational levels of the biological system. It usually involves genomic dynamics, namely, point mutations, gene amplification or other changes on the genomic level, which may result in increasing virulence of the neoplasia, or in the emergence of drug resistance. Chemotherapy may affect many events on the cellular level, such as cell-cycle arrest at different checkpoints, cell transition in and out of the proliferation cycle, etc. Chemotherapy may also interfere with the function of entire organs, most notably, with bone marrow blood production. In recent years molecular biology and genetics has made an important step forward in documenting many of these processes. Yet, for assessing the contribution of specific molecular elements to the great variety of disease profiles, experimental biology must be provided with tools that allow a formal and systematic analysis of the intricate interaction between the genomic, cellular and cell populations processes in the host and in the disease agent. This system is so complex that there is no intuitive way to know how small changes in the drug protocol will affect prognosis. But in spite of this intricacy, attempts to improve chemotherapy have been carried out by "trial and error" alone, with no formal theory underlying the application of specific drug schedules. Such an approach "is apt to result in no improvement, only discouragement and little useful information for future planning" (Skipper, 1986).

The treatment of cancer by cytotoxic drug (or drug combination) delivery is addressed. In the current model, two generic types of cells are considered: the limiting (i.e. the most drug-sensitive) host cells and the target cells. Target cells are, in fact, the tumor. Both types of cells may be damaged while exposed to chemotherapy. The aim is to obtain the most suitable treatment protocol according to specified conditions and limitations. It is assumed that the cell dynamics are deterministic and known, and that both types of cells are sensitive to chemotherapeutic agents in certain known period (fraction of the cell-cycle time ranging from 0 to 1) of the cell-cycle (denoted critical phase). If a cell is exposed to chemotherapy during part of its critical phase, there is a chance that it will be eliminated, blocked or affected in any other known way. The description of the dynamics of the delivered drugs is assumed to be known as well.

In order to achieve the goal optimization process is applied to the model. The optimization module uses the model predictions in order to search for the suitable solution to posted optimization problem. Precise defining of optimization objectives as well as the relevant parameters adjustment is done according to the settings defined by user/operator for every special case. The method can be applied in general cases as well as in specific ones.

IV.D.2. Model of Biological System

The basic layer of the model incorporates a description of age distribution of cycling cells and number of resting (quiescent) cells. The term "age of the cell" here refers to chronological age starting from the conventional beginning point of mitotic cycle.

Figure 13:
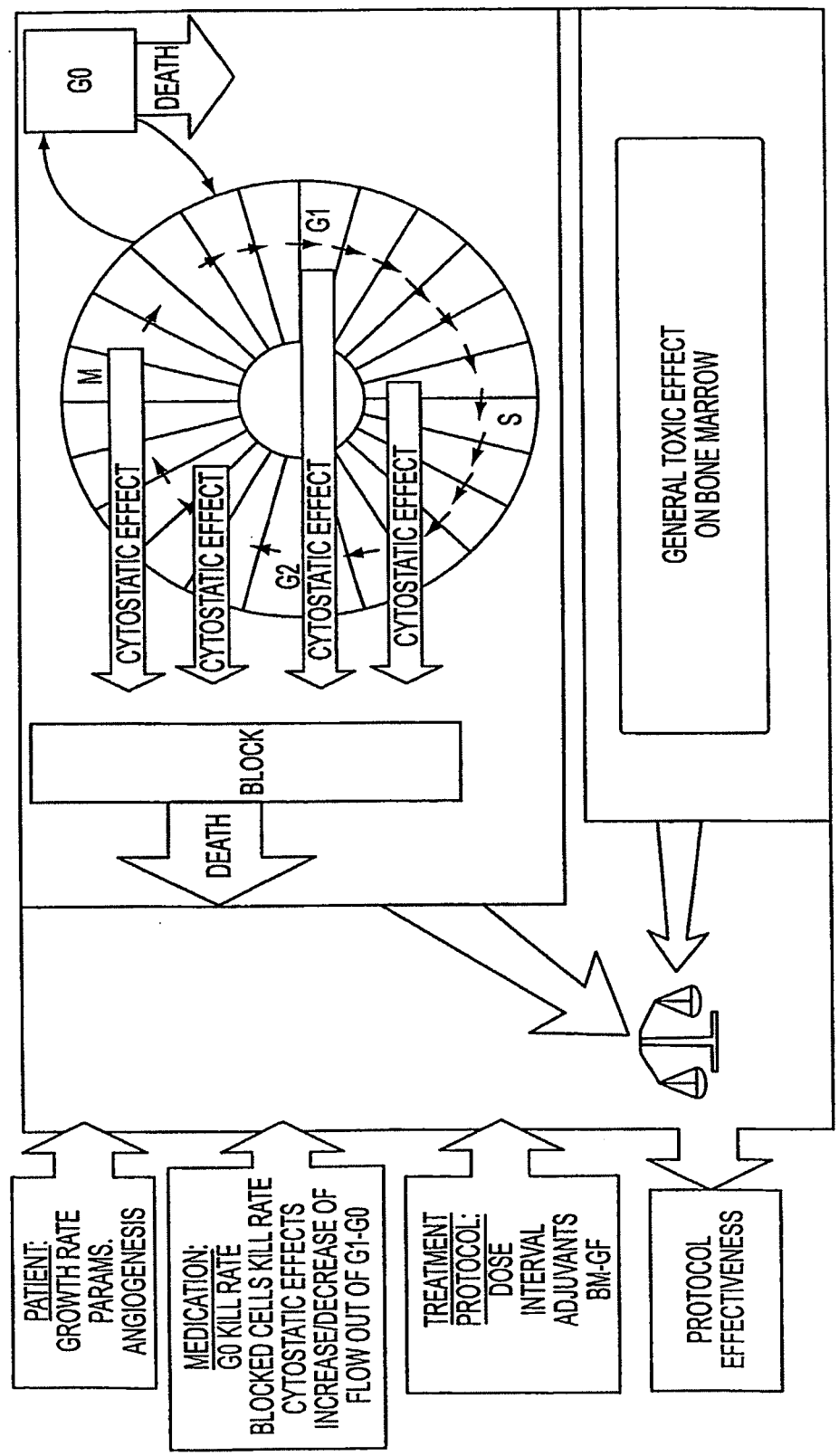
FIG. 13 is a schematic illustration of a biological model, in accordance with a further embodiment of the present invention.

Reference is now made to FIG. 13, which is a schematic illustration of the tumor cell cycle layer. The whole cycle is divided into 4 compartments, or stages ($G_1$, S, $G_2$ and M). Each compartment is divided into equal subcompartments, where $i^{th}$ subcompartment in each stage represents cells of age i in the particular stage (i.e. they have spent i time-steps in this stage). The quiescent stage is denoted $G_0$. The cell cycle follows a direction as shown by arrows (#). Thus, cells enter each stage starting with the first subcompartment, denoted $G_1$.

The model can be described mathematically as follows: Let $T_k$ denote the maximum duration of $k^{th}$ stage in the cycle. Let $\Delta t$ the symbol is showing up as a rectangle] denote the time resolution of the model in discrete time steps. $X_k^i(t)$ is a function, which represents the number of cells in stage k in the $I^{th}$ sub-compartment, at time t to $t+\Delta t$. Both time and age are measured in the same unit, in this case, hours. Let Q(t) represent the number of resting cells at time t to $t+\Delta t$. Trans(k,i,t) represents the probability that a cell of age i in the stage k will move to the next (k+1) compartment. Cells entering the new stage always start from the first subcompartment, i.e. from i=1. This probability may change with time, representing the influence of conditions on cycle length distribution.

By definition, the cell cannot remain more than $T_k$ timesteps in the $k^{th}$ compartment, as described in the following equation.

$$\forall k: \text{Trans}(k, T_k) = 1$$

The restriction point (R-point) represents a cell's commitment to complete to the mitotic cycle. Let $T_R$ denote the age at which the cell passes through the restriction point in $G_1$. Only cells in $G_1$ with $I<T_R$ can the cycle (in the absence of a drug).

The total number of proliferating cells P(t) can be calculated as follows:

$$P(t) = \sum_{k=G1,S,G2,M} \left( \sum_{i=1}^{T_k} x_k^i(t) \right)$$

In every time interval, quiescent cells may return to the proliferation pool. Alternatively, proliferating cells may change their state to become quiescent if and only if they are in the G1 stage and at age i, where $T_R \geq i > 0$. To describe this process we introduce the function $G_{1\to 0}(i,t)$ which describes the number of G1 cells in age i which become quiescent during time interval $[t, t+\Delta t]$. This function may receive negative values, accounting for cells that return from resting to proliferation.

As it is assumed that the exit to quiescence can occur only prior to the R-point (even in cancer cells), and that a resting cell that returns to proliferation enters the cycle at $T_0$, it can be stated:

$$\forall i > T_R, \forall t: G_{1\to 0}(i,t) = 0$$

It must be noted that this function is not dependent on i and t solely. Its value is determined according to current cell distribution and all the general parameters that characterize the described cells group. The same should be said about the values of Trans vector that can change during the history of given population.

The model traces the development of described group of cancer cells using given parameters, by calculating the number of cells in each and every subcompartment according to the following stepwise equations:

$$x_k^i(t) = \begin{cases} x_k^{i-1}(t-1) \cdot [1 - \text{Trans}(k, i-1, t-1)], & 1 < i \leq T_k \\ \sum_{j=1}^{T_{k-1}} [x_{k-1}^j(t-1) \cdot \text{Trans}(k-1, j, t-1)], & i = 1 \end{cases}$$

$$x_s^i(t) =$$

$$\begin{cases} x_s^{i-1}(t-1) \cdot [1 - \text{Trans}(S, i-1, t-1)], & 1 < i \leq T_{G1} \\ \sum_{j=1}^{T_{G1}} [x_{G1}^j(t-1) \cdot \text{Trans}(G1, j, t-1)] \cdot [1 - G_{1\to 0}(i-1, t-1), & i = 1 \end{cases}$$

for $k=G_2$, M, k−1 returns the previous stage (e.g. $G_2-1=S$).

These equations make it possible to calculate the number of cells in each subcompartment at every time interval $[t, \Delta t]$ starting from initial distribution (e.g. at time t=0). Since in this model cell ages are measured in absolute time units, these measurements refer to the chronological age of the cell, and not the biological age, whose units are relative to a maturation rate that differs from cell to cell. Consequently, in this model no cell can remain in the same age subcompartment after every time step. On the other hand, a fraction of the cells that leaves any subcompartment may be transferred to the first subcompartment of the next stage, according to probability vector Trans(k,i,t). This vector provides the ability to account for variability of cycle lengths while retaining a deterministic approach.

The behavior of the cell populations in this model is completely controlled by two components: Trans vector, and G1→G0 function. These two functions determine uniquely the outcome of every single time step, and, consequently the result over long periods. Thus, they are referred to as "control functions". The values of these functions may be dependent not only on time and age of cells, but also on the current population state (or, generally, on the whole history of the population) as well as on the environment associated with a given cell group. However, those parameters are similar for all the cells in the group, implying that the model presented here is suitable for describing highly homogenous group of cells. Therefore, the basic layer of the model should give a realistic description for a uniform group of cancer cells for which environmental conditions and relevant biological properties are defined, in a way that will allow the construction of the control functions for the group.

IV.D.3. The General Tumor Model

In the general approach the whole model is viewed as constructed from similar components, each of them derived from the basic structure described in the previous paragraph. Each component represents cells that are subjected to the same environmental conditions and, therefore behaves similarly (to be denoted homogenous group). The whole tumor is modeled as a union of many different homogenous groups of cells, where the development of each group can be accurately predicted (when local conditions are known).

This general model simulates progress of the tumor in discrete steps of time. At each step the number of cells in each subcompartment of each group is calculated according to the previous state, parameters of tumor, drug concentration, etc. The parameters of the tumor must include all the information that is relevant to prognosis. Some of these parameters are defined locally, e.g., those relating to the tumor's geometry. For this reason the representation of the spatial structure will be included.

The cells will be able to pass between the groups during the development of the tumor. This allows the representation of the changes in the local conditions during the tumor evolution (e.g. forming of necrotic core, improvement in "living conditions" in vascularized regions, etc.). In addition, all the parameters of the tumor may change in accordance with the dynamics of the cancer.

The calculation of the tumor development over time will be done by stepwise execution of the described simulation and can be used to predict the outcome of the treatment or in fitness function for search algorithms.

IV.D.4. From General to Individual Tumor Model

When the general theoretical description of the model is accomplished, the model is fitted to represent the actual tumors. It is rendered patient-specific by adjusting all the parameters that determine the behavior of the modeled tumor to those of the real cancer in the patient's body. In order to accomplish this task we will establish the connections between mathematical parameters (most of them will have direct biological implication) and every kind of data that is practically obtainable in the clinic. These connections may be defined through research on statistic correlation between different parameters (including genotype-phenotype correlation), or using advanced biochemical research showing the relationships between a given bio-marker and its effects on the reaction rates described by our model.

Thus defined, the model will be able to give realistic predictions for treatment outcomes either for specific patient or for a broad range profiles of patients and diseases. This tool can serve to perform the prognosis of either an untreated cancer patient, or as a basis for treatment modeling as is described below.

IV.D.5. Introducing Pharmacology

In order to simulate cancer treatment pharmacologic component is added to the above model. Pharmacokinetics as well as pharmacodynamics for specific anticancer drugs are modelled. Cell-cycle specific drugs and cell-cycle unspecific drugs are taken account of by our model.

The distribution of the drug in and around the tumor as well as in the blood (the drug kinetics) are modelled. For this purpose, a suitable model is used, defining it precisely for every certain type of the drug. The concentrations of drug in the body are calculated at every time step in accordance with the drug administration specified by the protocol, and different processes that define drug kinetics in the body.

The dynamics of the drug are represented through the direct influence of the drug on tumor cells. The effects on the proliferating cells are mostly blocking the cycle in different stages (which can be modeled as cell arrest) and cell death (immediate or some time after the block). Cell-cycle specific drugs are believed to have no direct influence on quiescent cells, but can affect them indirectly by killing proliferative cells and therefore changing local conditions. Where additional types of drugs added to the model, their effect on any kind of cells is modeled as killing certain fraction of cells (which is dose-dependent) or changing the behavior of the cells.

Additional phenomena that may prove significant in drug kinetics and dynamics (e.g. rate of absorption by the cells, development of tumor resistance to specific drug, angiogenesis etc.) can be introduced into the model to make it as realistic as needed.

The description of the drug in the model is done in terms of quantitative functions, which enable to calculate the drug amounts at certain locations and the tumor response to it at every time step. In the general case, these functions include parameters that depend on the specific data (drug type, body parameters, characteristic of the tumor, etc.) and can be determined in given situation (patient/case).

The combination of cancer model with the limiting normal tissue (see below), and the drug model described above makes it possible to predict the outcome of the treatment, given the relevant parameters for the drug, the cancer and the patient. Again, the prognosis may be made for specified cases as well as for broad profiles of patients or disease. This simulation also serves to build the fitness function used for the optimization objectives.

IV.D.6. Combining with Minimizing Host Toxicity.

Although an accurate predictive tool, the model that represents chemotherapy of tumor alone hardly suffice for optimization of drug protocols. Actually, this model implies using as much drug as possible until the final elimination of the tumor; while in the living system the toxicity of the drug is the most important constraint limiting the treatment. In most cases of anticancer chemotherapy the dose-limiting toxicity is bone marrow suppression, the two most sensitive bone marrow lineages being Granulopoiesis and Thrombopoiesis. Accordingly, those two were chosen as an example and are modeled separately and in a similar way to predict the negative effect of the chemotherapy on them. These to models reconstruct the damage caused by the chemotherapy to the bone marrow cells and the recovery of these lineages (treated by specific growth factors).

Thus, the whole system is capable of predicting the result of chemotherapy treatment for the tumor as well as for bone marrow cells, allowing the use of the protocols that combine anticancer drugs and growth factors for healthy cells.

Chemotherapy toxicity to any other normal host cell populations can be similarly taken into account, if it is defined as relevant for dose and schedule optimization.

IV.D.7. Individualization of the Models

Due to a great degree of heterogeneity between malignant tumors (even among similar tissue types) and between patients, it would be advantageous to adjust the treatment protocol to the individual case. This individualization procedure includes three aspects:

1) individual parameters of tumor dynamics.
2) individual parameters of patient-specific drug pharmacokinetics and interaction.
3) individual parameters of the dynamics of dose-limiting normal host tissues.

Relevant data concerning individual cases can be obtained by research on statistic correlation between different parameters (including genotype-phenotype correlation), or using advanced biochemical research (which may establish quantitative relations). In the general model, important dynamic parameters are estimated from experimental studies conducted in certain patient populations. Any of these parameters, when available on the per patient basis, can be individualized, while those that are unavailable can be left as a population-based figure. This approach allows continuous increase in the degree of individualization of the treatment protocols with progress in the technology of parameter evaluation (e.g., oncochips).

All different parameters may then be adjusted, which will result in an adjusted array of models to be simulated. Parameters may include many different factors, which are adjustable according to the needs of a researcher or a pharmaceutical company for general use of the treatment, or may even be individualized for use by a specific clinician for a particular individual. Examples of parameters may include, but are not limited to age, weight, gender, previous reaction to treatment, desired percentage of healthy body cells, desired length of treatment protocol, pathologic or cytologic specifics, molecular markers, genetic markers etc.

In order for the system to be user-friendly, all possible parameters are termed in ways that are easy for the user to understand.

Once all the parameters are set, an array of solutions is produced based on the input parameters. A number of possible protocols can be set (is thus generated by the computer). a fitness function is applied, which results in scores for each of the proposed solutions.

IV.D.8. Generation of Protocol Space

Referring back to FIG. 2, this model makes it possible to check any given treatment protocol and to choose a very good one according to user's criteria. The user may be a physician, a drug developer, a scientist, or anyone else who may need to determine a treatment protocol for a drug. The specific parameters may include several categories, such as individual patient characteristics and/or medical history, needs of a specific user (research, efficacy, treatment, etc.), and other particulars (such as maximum length of treatment, confidence level, etc.).

That is, an array of possible treatment protocols is created from which the optimal treatment protocol can then be chosen. It should be noted that the method does not imply the fitness estimation for all possible protocols. The use of operation research allows a much more sophisticated, yet resource saving procedure.

An example of this procedure will be described as it relates to cancer treatment by chemotherapy, as described in above-disclosed embodiment of the invention. However, it should be noted that a similar procedure may be performed in any of the embodiments.

The procedure implements cell growth and cell death procedures, as defined in the detailed model above. There are certain pre-defined parameters, including the lengths of the host and target life-cycles, the lengths of their critical phases, and a resolution factor, that determines the length of a single time unit. The user is asked to define an action (treatment or non-treatment). Simulation of cell growth and death is then performed for the single time unit. This procedure is repeated until the end of the total simulation. Alternatively, the choice of treatment or non-treatment is made by the processor, with many possible permutations considered. In that case, the protocol space would be very large, and the resolution would depend on the (selected) length of the time unit (and computer capacity)

There are two procedures: one for growth simulation during treatment and one without. The array in which the numbers of cells are kept is updated once per time unit, whether with or without treatment present at that time.

IV.D.9. Defining the Fitness Function

The fitness function is an important tool in Operation Research. In this case of protocol optimization, it allows the comparison between a number of different protocols each one of them scoring differently with respect to various objectives that can be set by the developers or by the users and identifying the protocol for which the highest weighted score is predicted. The fitness function calculates for any given protocol its relative efficacy ("score" or "fitness"), thus enabling a definite decision of the best protocol from a given set of protocols.

In different cases, different objectives can be formulated. There are several settings in which such a model can be used, including but not limited to:

One) clinical practice—where objectives can change depending on type of disease, condition of the patient, purpose of treatment, etc.

Two) pharmaceutical company—where objectives can be aimed at finding the therapeutic window and an optimal schedule.

Three) scientific setting—research oriented objectives can be aimed at.

In each case, a particular fitness function can be formulated, reflecting all given requirements. Thus, in any particular case one can compare between different protocols and obtain the most suitable to his/her special purposes and needs.

Examples for some alternative objectives are given:

1. The smallest number of drug dosings required for achieving any given aim.
2. The lowest total drug dose required for achieving any given aim.
3. The minimal total amount of drug needed for rehabilitation.
4. The smallest deviation from the baseline at normal cell populations count (e.g., platlet nadir) after chemotherapy or another cell-suppressive treatment.
5. The shortest period of disease (e.g., Thrombocytopenia).

Using the fitness function it is possible to a) estimate the efficacy of a given protocol, b) search for the solution of an optimization problem, i.e., predict which protocol will be best of many potential protocols considered for curing/relieving the patient.

IV.D.10. Solving the Optimization Problem

The optimization problem is stated using the described models: to find the protocol for drug administration (with option to growth factor administration) which maximizes the given fitness function.

As explained above, the fitness function is defined according to the user requirements. For example, the goal of the treatment may be defined as minimizing the number of cancer cells at the end of the treatment, minimizing the damage to the BM cells throughout the treatment or at its end, and curing the patient (where cure is defined precisely) as quickly as possible. Note that the fitness function may also include goals such as maximizing life expectancy, minimizing cost of treatment, minimizing treatment hazards and/or discomfort etc. Generally, the aim of optimization is to find the best protocol, i.e. the protocol that generates the best value of fitness. Customarily, this is achieved by mathematical analysis. However, mathematical analysis is restricted to over simplified models, whereas, in order to accommodate biologically realistic parameters, the described models are very complex and, therefore, cannot be solved analytically. On the other hand, the practical purpose of the treatment is not to find the best possible protocol (i.e., the global optimum) but "only" one that will suit the user's objectives, even if its fitness is not absolutely the best (i.e., the local optimum). For this reason the solution that can be shown to promise the pre-defined objectives is deemed satisfactory.

Hence, the optimization problem may be reformulated as follows: for given initial conditions, find the treatment protocol which will fulfill the user's requirements (e.g. curing a patient according to given definitions of cure) and subjected to given limitations (e.g. treatment duration, drug amounts, etc.). To this end it is not compulsory to find the global solution. It is enough, with regards to objectives and limitations, to perform search, using search algorithms, in certain regions of the protocols' space, and find the local maxima of the fitness function. After determining the locally best protocols, we can verify that they serve one's objectives and check them numerically for stability.

Such a strategy can be used for identifying patient-specific treatment, as well as in the general case, where only the profile of the disease and the drug are specified. If more patient-specific data are supplied, the solution will be tailored more specifically. On the other hand, the optimization program could propose general recommendations for the protocol types for certain kinds of disease, treated with a certain kind of medication.

It will be appreciated that the present invention is not limited by what has been described hereinabove and that numerous modifications, all of which fall within the scope of the present invention, exist. For example, while the present invention has been described with respect to certain specific cell lineages, the concept can be extended to any other lineage and treatment protocol which can be detailed mathematically (e.g., viral or bacterial diseases). Furthermore, certain assumptions were necessarily used in computing the mathematical models of the embodiments. Values and equations based on these assumptions can be changed if new information becomes available.

It will be appreciated by persons skilled in the art that the present invention is not limited by what has been particularly shown and described herein above. Rather the scope of the invention is defined by the claims which follow.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

The invention claimed is:

1. A computer system for recommending an optimal treatment protocol for treating cancer using drugs, for a general patient, said system comprising:
   a cancer system model;
   a treatment protocol generator for generating a plurality of treatment protocols for treating cancer using drugs;
   a system model modifier, wherein the said system model modifier is adapted to modify said cancer system model based on parameters specific to a population; and
   a selector adapted to select an optimal treatment protocol from said plurality of treatment protocols based on the modified system model; and
   a computer processor.

2. The system of claim 1 wherein the system model further comprises:
   a process model of cancer development; and
   a treatment model that is adapted to model the effects of treating cancer with drugs.

3. The system of claim 2 wherein said process model incorporates a distribution of cycling cells and quiescent cells.

4. The system of claim 2 where a tumor cell cycle is divided into at least four compartments G1, S, G2 and M and a quiescent stage is denoted by G0, wherein each of said four compartments is further subdivided into sub-compartments and an ith sub-compartment representing cells of age I in the corresponding compartment, wherein the system is adapted to ensure that cells entering a compartment always enter a first sub-compartment of the compartment.

5. The system of claim 4 wherein the model is adapted to trace development of cancer cells using a predetermined set of parameters by calculating a number of cells in each sub-compartment using stepwise equations.

6. The system of claim 5 wherein the system is adapted to use a probability vector to determine a fraction of cells that leaves any sub-compartment in a compartment to move to a first sub-compartment of the next compartment.

7. The system of claim 5 where the system includes a set of control functions that are adapted to uniquely determine an outcome of every single step, wherein said control functions comprise age of cells, state of a current population and associated environment.

8. The system of claim 5 wherein the system comprises a model representing a tumor, the model comprising a combination of a plurality of homogeneous groups of cells, each of said homogeneous groups of cells representing a similarly behaving group of cells distributed between all the cell-cycle compartments.

9. The system of claim 1, wherein the system is adapted to calculate in each step, a number of cells in each sub-compartment of each compartment of each group according to factors including a previous state, parameters of tumor, tumor current microenvironment and drug concentration.

10. The system of claim 9 where spatial structure of the tumor is included in the model.

11. The system of claim 10, wherein the system is adapted to incorporate pharmacokinetics and pharmacodynamics, cytostatic effects, cytotoxic effects, and other effects of anti-cancer drugs on cell disintegration.

12. The system of claim 11 wherein the system is adapted to incorporate a dose-limiting toxicity into the model.

13. The system of claim 1, wherein said parameters specific to the general patient comprise parameters related to tumor dynamics,—drug—pharmacokinetics, pharmacodynamics and dynamics of dose-limiting toxicity in host tissues.

14. A computer-implemented method for recommending an optimal treatment protocol for treating cancer using drugs for a general patient, said method comprising steps of:
creating a cancer system model;
enumerating a plurality of treatment protocols for treating cancer using drugs;
modifying the cancer system model based on parameters specific to the general population;
selecting an optimal treatment protocol from said plurality of treatment protocols based on the modified system model; and
recommending said optimal treatment;
wherein the steps are performed by a computer.

15. The method of claim 14 wherein the cancer system model further comprises:
a process model of cancer development; and
a treatment model that models the effects of treating cancer with drugs.

16. The method of claim 15 wherein said process model incorporates a distribution of cycling cells and quiescent cells.

17. The method of claim 15 where a tumor cell cycle is divided into at least four compartments G1, S, G2 and M and a quiescent stage is denoted by G0, wherein each of said four compartments is further subdivided into sub-compartments and an ith sub-compartment representing cells of age I in the corresponding compartment, wherein cells entering a compartment always enter a first sub-compartment of the compartment.

18. The method of claim 17 wherein the model traces development of cancer cells using a predetermined set of parameters by calculating a number of cells in each sub-compartment using stepwise equations.

19. The method of claim 18 wherein a probability vector is used to determine a fraction of cells that leaves any sub-compartment in a compartment to move to a first sub-compartment of the next compartment.

20. The method of claim 18 where a set of control functions uniquely determines an outcome of every single step, wherein said control functions comprise age of cells, state of a current population and associated environment.

21. The method of claim 18 wherein a tumor is modeled as a combination of a plurality of homogeneous groups of cells, each of said homogeneous groups of cells representing a similarly behaving group of cells distributed between all the cell-cycle compartments.

22. The method of claim 21, wherein in each step, a number of cells in each sub-compartment of each compartment of each group is calculated according to factors including a previous state, parameters of tumor, current tumor microenvironment and drug concentration.

23. The method of claim 21 where spatial structure of the tumor is included in the model.

24. The method of claim 23, wherein pharmacokinetics, pharmacodynamics, cytotoxic effects, cytostatic effects and other effects of anticancer drugs on cell disintegration are incorporated into the model.

25. The method of claim 24, wherein a dose-limiting toxicity is incorporated into the model.

26. The method of claim 14, wherein, said parameters specific to the general patient comprise parameters related to tumor dynamics, drug pharmacokinetics, pharmacodynamics and dynamics of dose-limiting toxicity in host tissues.

27. The method of claim 26, wherein said parameters related to tumor dynamics comprise age, weight, gender, percentage of limiting healthy cells, desired length of treatment protocol, previous reaction to treatment, molecular markers, genetic markers, pathologic markers and cytologic markers.

28. The system of claim 13, wherein said parameters related to tumor dynamics comprise age, weight, gender, percentage of limiting healthy cells, desired length of treatment protocol, previous reaction to treatment, molecular markers, genetic markers, pathologic markers and cytologic markers.

* * * * *